(12) United States Patent
Bock et al.

(10) Patent No.: US 10,899,826 B1
(45) Date of Patent: Jan. 26, 2021

(54) PHARMACEUTICAL COMPOSITIONS FOR AN ANTI-CGRP ANTAGONIST ANTIBODY

(71) Applicant: Teva Pharmaceuticals International GmbH, Jona (CH)

(72) Inventors: Jason Bock, North Potomac, MD (US); John Kim, West Chester, PA (US)

(73) Assignee: Teva Pharmaceuticals International GmbH, Jona (CH)

( * ) Notice: Subject to any disclaimer, the term of this patent is extended or adjusted under 35 U.S.C. 154(b) by 0 days.

(21) Appl. No.: 16/569,462

(22) Filed: Sep. 12, 2019

Related U.S. Application Data

(60) Provisional application No. 62/730,916, filed on Sep. 13, 2018.

(51) Int. Cl.
| | |
|---|---|
| *C07K 16/18* | (2006.01) |
| *A61K 39/395* | (2006.01) |
| *A61K 9/00* | (2006.01) |
| *A61K 47/26* | (2006.01) |
| *A61K 47/34* | (2017.01) |
| *A61K 47/18* | (2017.01) |

(52) U.S. Cl.
CPC ............ *C07K 16/18* (2013.01); *A61K 9/0019* (2013.01); *A61K 39/39591* (2013.01); *A61K 47/183* (2013.01); *A61K 47/26* (2013.01); *A61K 47/34* (2013.01); *C07K 2317/524* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,399,216 A | 8/1983 | Axel et al. | |
| 4,634,665 A | 1/1987 | Axel et al. | |
| 4,816,397 A | 3/1989 | Boss et al. | |
| 4,816,567 A | 3/1989 | Cabilly et al. | |
| 5,179,017 A | 1/1993 | Axel et al. | |
| 5,545,806 A | 8/1996 | Lonberg et al. | |
| 5,545,807 A | 8/1996 | Surani et al. | |
| 5,569,825 A | 10/1996 | Lonberg et al. | |
| 5,625,126 A | 4/1997 | Lonberg et al. | |
| 5,633,425 A | 5/1997 | Lonberg et al. | |
| 5,661,016 A | 8/1997 | Lonberg et al. | |
| 5,750,373 A | 5/1998 | Garrard et al. | |
| 5,981,568 A | 11/1999 | Kunz et al. | |
| 7,329,353 B2 | 2/2008 | Dillon et al. | |
| 7,597,889 B1 | 10/2009 | Amour et al. | |
| 7,928,205 B2 | 4/2011 | Dillon et al. | |
| 8,007,794 B2 | 8/2011 | Zeller et al. | |
| 8,293,239 B2 | 10/2012 | Poulsen et al. | |
| 8,298,536 B2 | 10/2012 | Poulsen et al. | |
| 8,586,045 B2 | 11/2013 | Zeller et al. | |
| 8,597,649 B2 | 12/2013 | Zeller et al. | |
| 8,623,366 B2 | 1/2014 | Pios et al. | |
| 8,734,802 B1 | 5/2014 | Zeller et al. | |
| 9,115,194 B2 | 8/2015 | Zeller et al. | |
| 9,266,951 B2 | 2/2016 | Zeller et al. | |
| 9,328,167 B2 | 5/2016 | Poulsen et al. | |
| 9,328,168 B2 | 5/2016 | Zeller et al. | |
| 9,340,614 B2 | 5/2016 | Zeller et al. | |
| 9,346,881 B2 | 5/2016 | Zeller et al. | |
| 9,365,648 B1 | 6/2016 | Zeller et al. | |
| 9,884,907 B2 | 2/2018 | Zeller et al. | |
| 9,884,908 B2 | 2/2018 | Zeller et al. | |
| 9,890,210 B2 | 2/2018 | Zeller et al. | |
| 9,890,211 B2 | 2/2018 | Zeller et al. | |
| 9,896,502 B2 | 2/2018 | Bigal et al. | |
| 10,323,085 B2 | 6/2019 | Poulsen et al. | |
| 10,329,343 B2 | 6/2019 | Zeller et al. | |
| 10,392,434 B2 | 8/2019 | Bigal et al. | |
| 10,519,224 B2 | 12/2019 | Bigal et al. | |
| 10,556,945 B2 | 2/2020 | Bigal et al. | |
| 10,597,448 B2 | 3/2020 | Pios et al. | |
| 2005/0161399 A1 | 7/2005 | Dillon et al. | |
| 2006/0194280 A1 | 8/2006 | Dillon et al. | |
| 2007/0136826 A1* | 6/2007 | Dunn ................ | C07K 16/2887 800/3 |
| 2012/0294797 A1* | 11/2012 | Kovacevich ....... | A61K 39/3955 424/1.11 |
| 2013/0144041 A1 | 6/2013 | Dillon et al. | |
| 2013/0295087 A1 | 11/2013 | Poulsen et al. | |
| 2013/0295088 A1 | 11/2013 | Poulsen et al. | |
| 2014/0308290 A1 | 10/2014 | Pios et al. | |
| 2014/0314767 A1 | 10/2014 | Pios et al. | |
| 2014/0371427 A1 | 12/2014 | Dillon et al. | |
| 2017/0044243 A1 | 2/2017 | Poulsen et al. | |
| 2017/0073398 A1 | 3/2017 | Poulsen et al. | |
| 2017/0081395 A1 | 3/2017 | Zeller et al. | |
| 2017/0088612 A1 | 3/2017 | Bigal | |
| 2017/0240622 A1 | 8/2017 | Zeller et al. | |
| 2017/0275352 A1 | 9/2017 | Poulsen et al. | |
| 2018/0111984 A1 | 4/2018 | Bigal et al. | |
| 2018/0305443 A1 | 10/2018 | Poulsen et al. | |
| 2019/0071490 A1 | 3/2019 | Burnstein | |
| 2019/0092841 A1 | 3/2019 | Zeller et al. | |
| 2020/0087384 A1 | 3/2020 | Poulsen et al. | |
| 2020/0102377 A1 | 4/2020 | Bigal et al. | |
| 2020/0148752 A1 | 5/2020 | Poulsen et al. | |
| 2020/0148761 A1 | 5/2020 | Bigal | |

FOREIGN PATENT DOCUMENTS

| | | |
|---|---|---|
| WO | WO 1999058572 | 11/1999 |
| WO | WO 2000053211 | 9/2000 |

(Continued)

OTHER PUBLICATIONS

Pellesi, et al., Spotlight on Anti-CGRP Monoclonal Antibodies in Migraine: The Clinical Evidence to Date, 2017, Clinical Pharmacology in Drug Development 6(6):534-547 (Year: 2017).*

(Continued)

*Primary Examiner* — John D Ulm
(74) *Attorney, Agent, or Firm* — Fish & Richardson P.C.

(57) ABSTRACT

The present disclosure provides pharmaceutical compositions including a plurality of IgG2 anti-CGRP antagonist antibodies comprising a high content of particular IgG2 disulfide isomers, and methods of using the same.

52 Claims, 23 Drawing Sheets

Specification includes a Sequence Listing.

(56) References Cited

FOREIGN PATENT DOCUMENTS

| WO | WO 2006047340 | 5/2006 |
|---|---|---|
| WO | WO 2007054809 | 5/2007 |
| WO | WO 2009036209 | 3/2009 |
| WO | WO 2009109908 | 9/2009 |
| WO | WO 2009109911 | 9/2009 |
| WO | WO 2011024113 | 3/2011 |
| WO | WO 2013086448 | 6/2013 |
| WO | WO 2015143409 | 9/2015 |
| WO | WO 2015176017 | 11/2015 |
| WO | WO 2017051385 | 3/2017 |
| WO | WO 2018055573 | 3/2018 |
| WO | WO 2018055574 | 3/2018 |

OTHER PUBLICATIONS

Alabi et al., "Human Fc receptor-like 5 distinguishes IgG2 disulfide isoforms and deamidated charge variants," Molecular Immunology, vol. 92, 161-168, 2017, 8 pages.

Boerner et al., "Production of Antigen-Specific Human Monoclonal Antibodies from in Vitro-Primed Human Splenocytes," The Journal of Immunology, vol. 147 (1):86-95, Jul. 1, 1991, 10 pages.

Chothia et al., "Canonical Structures for the Hypervariable Regions of Immunoglobulins," J. Mol. Biol. 196: 901-917, Aug. 20, 1987, 17 pages.

Cole et al., "The EBV-Hybridoma Technique and its Application to Human Lung Cancer," Monoclonal Antibodies and Cancer Therapy, Alan R. Liss, p. 77, 1985, 1 page.

Dillon et al., "Optimization of a Reversed-Phase High-Performance Liquid chromatography/mass Spectrometry Method for Characterizing Recombinant Antibody Heterogeneity and Stability," J. Chromatogr. A 1120: 112-20, Jul. 2006, 9 pages.

Dillon et al., "Structural and Functional Characterization of Disulfide Isoforms of the Human IgG2 Subclass," The Journal of Biological Chemistry, vol. 283, No. 23, pp. 16206-16215, Jun. 6, 2008, 116 pages.

Du et al., "Chromatographic Analysis of the Acidic and Basic Species of Recombinant Monoclonal Antibodies," MAbs 4(5): 578-85, Sep.-Oct. 2012, 9 pages.

GE Healthcare, "Protein Purification Handbook," 18-1132-29, 2007, 96 pages.

Grujic et al., "Impact of Antibody Subclass and Disulfide Isoform Defferences on the Biological Activity of CD200R and Bklotho Agonist Antibodies," Biochemical and Biophysical Research Communications, 486, 985-991, 2017, 7 pages.

Hoogenboom and Winter, "By-passing immunisation: Human antibodies from synthetic repertoires of germline VH gene segments rearranged in vitro," Journal of Molecular Biology, vol. 227, Issue 2, 381-388, Sep. 1992, 8 pages.

Jones, "Analysis of polypeptides and proteins," Advanced Drug Delivery Reviews, vol. 10, Issue 1, pp. 29-90, Jan.-Apr. 1993, 62 pages.

Kaufman and Sharp, "Amplification and Expression of Sequences Cotransfected With a Modular Dihydrofolate Reductase Complementary Dna Gene," Mol. Biol. 159:601-621, Aug. 1982, 21 pages.

Kohler and Milstein, "Continuous cultures of fused cells secreting antibody of predefined specificity," Nature, 256:495, 1975, 3 pages.

Krishnan et al., "Chapter 16: Development of Formulations for Therapeutic Monoclonal Antibodies and Fc Fusion Proteins," in Jameel and Hershenson, 25 eds. Formulation and Process Development Strategies for Manufacturing Biopharmaceuticals. NJ: Wiley p. 383-427, 2010, 45 pages.

Liu and May, "Disulfide bond structures of IgG molecules," mAbs, 4:1, 17-23, DOI: 10.4161/mabs.4.1.18347, 2012, 8 pages.

Liu et al., "Human IgG2 Antibody Disulfide Rearrangement in Vivo," The Journal of Biological Chemistry, vol. 283, No. 43, pp. 29266-29272, Oct. 24, 2008, 7 pages.

Liu et al., "IgG2 disulfide isoform conversion kinetics," Molecular Immunology, vol. 54, 217-226, 2013, 10 pages.

Liu et al., "Protected Hinge in the Immunoglobulin G2-A2 Disulfide Isoform," Prot. Sci. 23: 1753-64, Dec. 2014, 12 pages.

Marks et al., "By-passing Immunization Human Antibodies from V-gene Libraries Displayed on Phage," J. Mol. Biol., 222:581, 1991, 17 pages.

McCafferty et al., "Phage antibodies: filamentous phage displaying antibody variable domains," Nature, 348:552-554, 1990, 3 pages.

Moritz and Stracke, "Assessment of disulfide and hinge modifications in monoclonal antibodies," Review, Electrophoresis, 38, 769-785, 2017, 17 pages.

Resemann et al., "Rapid, automated characterization of disulfide bond scrambling and IgG2 isoform determination," MABS, vol. 10, No. 8, 1200-1213, 2018, 14 pages.

Schou et al., "Calcitonin Gene-Related Peptide and Pain: a Systemic Review," The Journal of Headache and Pain 18:34; DOI 10.1186/s10194-017-0741-2, 2017, 17 pages.

Shakla et al., Process Scale Bioseparation for the Biopharmaceutical Industry, CRC Press Taylor & Francis Group, pp. 188-196, 2007, 26 pages.

Sheets et al., "Efficient construction of a large nonimmune phage antibody library: The production of high-affinity human single-chain antibodies to protein antigens," PNAS, (USA) 95:6157-6162, May 1998, 6 pages.

Shigenori Harada et al., "Hinge region of human IgG2 protein: Conformational studies with monoclonal antibodies," Molecular Immunology, vol. 29, Issue 2, 145-149, Feb. 1992, 5 pages.

Shigenori Harada et al., "Identification of epitopes recognized by a panel of six anti-human IgG2 monoclonal antibodies," Journal of Immunological Methods, vol. 141, Issue 1, 89-96, Jul. 26, 1991, 8 pages.

Urlaub and Chasin, "Isolation of Chinese hamster cell mutants deficient in dihydrofolate reductase activity," Proc. Natl. Acad. Sci. USA 77:4216-4220, Jul. 1980, 5 pages.

Vaughan et al., "Human Antibodies with Sub-nanomolar Affinities Isolated from a Large-immunized Phage Display Library," Nature Biotechnology, 14:309-314, Mar. 1996, 6 pages.

Wang et al., "Disulfide Scrambling in IgG2 Monoclonal Antibodies: Insights from Molecular Dynamics Simulations," Pharm. Res. 28:3128-3144, 2011, 17 pages.

Wang et al., "Investigation of antibody disulfide reduction and re-oxidation and impact to biological activities," Journal of Pharmaceutical and Biomedical Analysis, vol. 102, 519-528, 2015, 10 pages.

Wang, "Instability, Stabilization, and Formulation of Liquid Protein Pharmaceuticals," Int. J. Pharm. 185: 129-188, Aug. 20, 1999, 60 pages.

Wang, "Lyophilization and Development of Solid Protein Pharmaceuticals," Int. J. Pharm. 203: 1-60, Aug. 10, 2000, 60 pages.

WHO Drug Information 30(2): 280-1, 2016, 70 pages.

Wypych et al., "Human IgG2 Antibodies Display Disulfide-mediated Structural Isoforms," The Journal of Biological Chemistry, vol. 283, No. 23, pp. 16194-16205, Jun. 6, 2008, 12 pages.

Zhang et al., "Conformational Difference in Human IgG2 Disulfide Isoforms Revealed by Hydrogen/Deuterium Exchange Mass Spectrometry," Biochemistry, vol. 54, 1956-1962, 2015, 7 pages.

Zhang et al., "Determination of Fab-Hinge Disulfide Connectivity in Structural Isoforms of a Recombinant Human Immunoglobulin G2 Antibody," Anal. Chem. vol. 82, 1090-1099, 2010, 10 pages.

Zhang et al., "Structural Changes and Aggregation Mechanisms of Two Different Dimers of an IgG2 Monoclonal Antibody," Biochemistry, vol. 57, 5466-5479, 2018, 14 pages.

Karasek et al., "Characterization of the intrinsic binding features of three anti-CGRP therapeutic antibodies effective in preventing migraine: a comparative pre-clinical case study of ALD403, LY-2951742, TEV-48125," Poster, Presented at the 58th Annual Scientific Meeting of the American Headache Society, San Diego, CA, Jun. 9, 2016, Alder Biopharmaceuticals, 1 page.

Leblanc et al., "Charge variants characterization of a monoclonal antibody by ion exchange chromatography coupled on-line to native mass spectrometry: Case study after a long-term storage at +5° C.," Journal of Chromatography B, Mar. 2017, 1048:130-139.

* cited by examiner

| Sample | λ₁ (nm) | λ₂ (nm) | λ₃ (nm) | λ₄ (nm) |
|---|---|---|---|---|
| Fraction#4 | 292.4 | 272.9 | 267.5 | 261.0 |
| Fraction#5 | 292.4 | 272.6 | 267.2 | 261.1 |
| Fraction#6 | 292.3 | 273.0 | 267.3 | 261.3 |

| Sample | λ₁ (nm) | λ₂ (nm) | λ₃ (nm) |
|---|---|---|---|
| Fraction#4 | 227.0 | 216.6 | 201.8 |
| Fraction#5 | 227.7 | 216.6 | 201.1 |
| Fraction#6 | 227.4 | 216.6 | 201.8 |

US 10,899,826 B1

PHARMACEUTICAL COMPOSITIONS FOR AN ANTI-CGRP ANTAGONIST ANTIBODY

CROSS-REFERENCE TO RELATED APPLICATION

This application claims priority to U.S. Patent Application Ser. No. 62/730,916, filed Sep. 13, 2018, which is incorporated by reference in its entirety.

REFERENCE TO SEQUENCE LISTING

The instant application contains a Sequence Listing which has been submitted in ASCII format via EFS-Web and is hereby incorporated by reference in its entirety. The sequence listing contains no new matter. Said ASCII copy, created on Oct. 30, 2019, is named 43612_0004008_Seq_List.txt and is 14.4 Kilobytes in size.

BACKGROUND

Antibodies of the IgG2 subclass exhibit structural heterogeneity attributable to distinct isoforms that are formed when alternate disulfide bond linkages form between the Fab arms and the hinge regions of the antibodies. Three major disulfide isoforms of IgG2 have been identified (see Dillon et al. (2008) *J. Biol. Chem.* 283(23): 16206-215; and Wypych et al. (2008) *J. Biol. Chem.* 283(23): 16194-205). In the IgG2-A disulfide isoform, the cysteine near (λ) or at (κ) the C-terminus of each light chain of the antibody is linked to the Fab arm of the heavy chain via a disulfide bond. In contrast, in the IgG2-B disulfide isoform, both Fab arms of the antibody are disulfide bond linked to the hinge region of the antibody. The IgG2-A/B disulfide isoform is a hybrid disulfide isoform in which only one of the Fab arms is disulfide bond linked to the hinge region of the antibody. Additional sub-isoforms of each major IgG2 disulfide isoform have been identified (see, e.g., Zhang et al. (2010) *Anal. Chem.* 82: 1090-99; and Liu et al. (2014) *Prot. Sci.* 23: 1753-64).

Differences in disulfide bond connectivity affects the overall conformation and flexibility of IgG2 disulfide isoforms (Krishnan et al. (2010) "Development of Formulations for Therapeutic Monoclonal Antibodies and Fc Fusion Proteins," in Jameel and Hershenson, eds. Formulation and Process Development Strategies for Manufacturing Biopharmaceuticals. NJ: Wiley p. 383-427)). For example, the disulfide isoform IgG2-A has greater flexibility than the disulfide isoform IgG2-B. The existence of IgG2 disulfide isoform heterogeneity may have important therapeutic implications, as each isoform may behave differently in vitro (e.g., during storage) or in vivo. Dillon et al. showed that an IgG2 that was directed against a non-membranebound target that was tested showed activity differences between IgG2-A and IgG2-B, and suggested that the structure-function relationship is likely to depend on the nature and accessibility of the epitope for a particular IgG2 antibody (e.g., solution versus cell-surface receptor, receptor density, etc.) and the role avidity plays in the overall activity of the antibody (Dillon et al. (2008)). Furthermore, at least one human IgG receptor that preferentially binds to IgG2-A disulfide isoforms was recently identified (Alabi et al. (2017) *Mol. Immunol.* 92:161-8). Given that different IgG2 disulfide isoforms of the anti-CGRP antagonist antibody fremanezumab may behave differently in vitro or in vivo, preparations including homogenous populations of the disulfide isoforms of fremanezumab are highly desirable for clinical use.

SUMMARY

This disclosure provides pharmaceutical compositions including a plurality of IgG2 anti-CGRP antagonist antibody molecules that comprise a high content of the IgG2-B disulfide isoform.

Accordingly, provided herein is a pharmaceutical composition comprising a plurality of IgG2 anti-CGRP antagonist antibody molecules, wherein at least about 70% of the antibody molecules in the composition are of the IgG2-B disulfide isoform, and wherein each of the antibody molecules comprises both a heavy chain variable domain amino acid sequence comprising the amino acid sequence of SEQ ID NO: 1 and a light chain variable domain amino acid sequence comprising the amino acid sequence of SEQ ID NO: 2.

In some embodiments, each of the antibody molecules comprise a kappa light chain constant region.

In some embodiments, each of the antibody molecules comprise a heavy chain comprising a modified CH2 domain, wherein the modified CH2 domain comprises the amino acid sequence of SEQ ID NO: 15.

In some embodiments, each of the antibody molecules comprise a heavy chain comprising the amino acid sequence of SEQ ID NO: 3 and a light chain comprising the amino acid sequence of SEQ ID NO: 4.

In some embodiments, between about 15% and about 25% of the antibody molecules in the composition are of the IgG2-A/B disulfide isoform.

In some embodiments, between about 3% and about 7% of the antibody molecules in the composition are of the IgG2-A disulfide isoform.

In some embodiments, at least about 5% of the antibody molecules in the composition are of the IgG2-A disulfide isoform.

In some embodiments, at least about 20% of the antibody molecules in the composition are of the IgG2-A/B disulfide isoform.

Also provided herein is a pharmaceutical composition comprising a plurality of IgG2 monoclonal antibody molecules,
wherein between about 70% and about 80% of the antibody molecules in the composition are of the IgG2-B disulfide isoform;
wherein between about 3% and about 7% of the antibody molecules in the composition are of the IgG2-A disulfide isoform;
wherein between about 15% and about 25% of the antibody molecules in the composition are of the IgG2-A/B disulfide isoform; and
wherein each of the antibody molecules comprises a heavy chain variable domain amino acid sequence comprising the amino acid sequence of SEQ ID NO: 1 and a light chain variable domain amino acid sequence comprising the amino acid sequence of SEQ ID NO: 2.

In some embodiments, each of the antibody molecules comprise a kappa light chain constant region.

In some embodiments, each of the antibody molecules comprise a heavy chain comprising a modified CH2 domain, wherein the modified CH2 domain comprises the amino acid sequence of SEQ ID NO: 15.

In some embodiments, each of the antibody molecules comprise both a heavy chain comprising the amino acid sequence of SEQ ID NO: 3 and a light chain comprising the amino acid sequence of SEQ ID NO: 4.

In some embodiment of any of the compositions provided herein, about 72% of the antibody molecules in the composition are of the disulfide isoform B, wherein about 22% of the antibody molecules in the composition are of the IgG2-A/B, and wherein about 6% of the antibody molecules in the composition are of the IgG2-A disulfide isoform.

In some embodiments of any of the compositions provided herein, the amount of each disulfide isoform present in the composition is as determined using reverse-phase high-performance liquid chromatography (RP-HPLC). In further embodiments, the reverse-phase high performance liquid chromatography (RP-HPLC) is performed after cleaving the anti-CGRP antagonist antibody molecules below the hinge region (with, e.g., FabRICATOR® as described in Example 1).

In some embodiments of any of the compositions provided herein, the amount of the IgG2-B disulfide isoform present in the composition is as determined using the reverse-phase high-performance liquid chromatography (RP-HPLC) method described in Example 1.

In some embodiments of any of the compositions provided herein, the composition is liquid and wherein the plurality of IgG2 antibody molecules are present in the composition at a concentration of least about 120 mg/mL.

In some embodiments of any of the compositions provided herein, the composition is liquid and wherein the plurality of IgG2 antibody molecules are present in the composition at a concentration of at least about 150 mg/mL.

In some embodiments of any of the compositions provided herein, the composition further comprises a sugar or a sugar alcohol.

In some embodiments, the sugar or sugar alcohol is selected from the group consisting of sorbitol, sucrose, trehalose, and mannitol.

In some embodiments of any of the compositions provided herein, the composition further comprises a chelating agent.

In some embodiments, the chelating agent is ethylenediaminetetraacetic acid (EDTA) or diethylenetriaminepentaacetic acid (DTPA).

In some embodiments of any of the compositions provided herein, the composition further comprises a surfactant.

In some embodiments, the surfactant is polysorbate 20, polysorbate 60, polysorbate 80, or a combination thereof.

In some embodiments of any of the compositions provided herein, the composition further comprises a buffering agent.

In some embodiments, the buffering agent comprises histidine, arginine, glycine, asparagine, or a combination thereof.

In some embodiments of any of the compositions provided herein, the composition comprises a pH of between about 5.0 and about 6.0.

In some embodiments of any of the compositions provided herein, the composition comprises a pH of about 5.5.

In some embodiments of the compositions provided herein, the plurality of IgG2 antibody molecules are present in the composition at a concentration of at least about 150 mg/mL, wherein the composition is a liquid composition, and wherein the composition comprises about 3.5 mM L-histidine, about 12.5 mM L-histidine hydrochloride monohydrate, about 193 mM sucrose, about 0.37 mM EDTA, and about 0.15 mM polysorbate 80, at about pH 5.5.

In some embodiments of any of the compositions provided herein, the composition comprises a conductivity of from about 1.3 mS/cm to about 1.5 mS/cm.

In some embodiments of any of the compositions provided herein, wherein 95% of the antibody molecules in the composition are monomeric as determined by size exclusion high-performance liquid chromatography (SE-HPLC).

In some embodiments of any of the compositions provided herein, 5% of the antibody molecules in the composition are dimeric as determined by SE-HPLC.

In some embodiments of any of the compositions provided herein, 3.5% of the antibody molecules in the composition are dimeric as determined by SE-HPLC.

In some embodiments of any of the compositions provided herein, the composition is stable after storage at from about 2 to about 8° C. for at least 3 months.

In some embodiments of any of the compositions provided herein, the composition is stable after storage at from about 2 to about 8° C. for at least 6 months.

In further embodiments, the antibody molecules in the composition retain at least about 80% of their antigen-binding activity after storage, as compared to the antigen-binding activity of the antibody molecules in the composition prior to storage.

In some embodiments of any of the compositions provided herein, the composition is stored in a container selected from the group consisting of a vial, a cartridge, a syringe, and an autoinjector device.

In some embodiments of any of the compositions provided herein, the composition is suitable for subcutaneous or intravenous administration to a subject.

In some embodiments, the container comprises less than about 2 mL of the pharmaceutical composition.

In some embodiments, the container comprises 1.5 mL of the pharmaceutical composition.

Also provided herein is a liquid pharmaceutical composition comprising about 225 mg fremanezumab, about 0.204 mg disodium ethylenediaminetetraacetic acid dihydrate (EDTA), about 0.815 mg L-histidine, about 3.93 mg L-histidine hydrochloride monohydrate, about 0.3 mg polysorbate-80, about 99 mg sucrose, and water for injection, at a pH of about 5.5, wherein at least about 70% of the fremanezumab in the liquid pharmaceutical composition is of the IgG2-B disulfide isoform; and wherein the liquid pharmaceutical composition has a volume of about 1.5 mL.

Also provided herein is a pre-filled syringe comprising about 1.5 mL of a liquid pharmaceutical composition, wherein the liquid pharmaceutical composition comprises about 225 mg fremanezumab, about 0.204 mg disodium ethylenediaminetetraacetic acid dihydrate (EDTA), about 0.815 mg L-histidine, about 3.93 mg L-histidine hydrochloride monohydrate, about 0.3 mg polysorbate-80, about 99 mg sucrose, and water for injection, at a pH of about 5.5, wherein at least about 70% of the fremanezumab in the liquid pharmaceutical composition is of the IgG2-B disulfide isoform.

Also provided herein is an autoinjector comprising about 1.5 mL of a liquid pharmaceutical composition, wherein the liquid pharmaceutical composition comprises about 225 mg fremanezumab, about 0.204 mg disodium ethylenediaminetetraacetic acid dihydrate (EDTA), about 0.815 mg L-histidine, about 3.93 mg L-histidine hydrochloride monohydrate, about 0.3 mg polysorbate-80, about 99 mg sucrose, and water for injection, at a pH of about 5.5, wherein at least about 70% of the fremanezumab in the liquid pharmaceutical composition is of the IgG2-B disulfide isoform.

Also provided herein is a method of treating headache in a subject in need thereof, comprising administering a therapeutically effective amount of a pharmaceutical composition comprising a plurality of IgG2 anti-CGRP antagonist antibody molecules, wherein at least about 70% of the antibody molecules in the composition are of the IgG2-B disulfide isoform, and wherein each of the antibody molecules comprises both a heavy chain variable domain amino acid sequence comprising the amino acid sequence of SEQ ID NO: 1 and a light chain variable domain amino acid sequence comprising the amino acid sequence of SEQ ID NO: 2.

In some embodiments, the headache is migraine headache. In further embodiments, the migraine headache is chronic migraine headache or episodic migraine headache.

In some embodiments, the headache is cluster headache. In further embodiments, the cluster headache is chronic cluster headache or episodic cluster headache.

In some embodiments, the headache is post-traumatic headache, post-ictal headache, or medication overuse headache.

Also provided herein is a method of treating pain in a subject in need thereof, comprising administering a therapeutically effective amount of a pharmaceutical composition comprising a plurality of IgG2 anti-CGRP antagonist antibody molecules, wherein at least about 70% of the antibody molecules in the composition are of the IgG2-B disulfide isoform, and wherein each of the antibody molecules comprises both a heavy chain variable domain amino acid sequence comprising the amino acid sequence of SEQ ID NO: 1 and a light chain variable domain amino acid sequence comprising the amino acid sequence of SEQ ID NO: 2.

In some embodiments, the pain is chronic pain. In further embodiments, the chronic pain is associated with fibromyalgia.

In some embodiments, the pain is visceral pain. In further embodiments, the visceral pain is (a) associated with or results from interstitial cystitis, or (b) is associated with or results from bladder pain syndrome.

BRIEF DESCRIPTION OF THE DRAWINGS

FIG. 7A shows peptide mapping results for the fremanezumab DS. FIG. 7B shows peptide mapping results for the isoform control. FIG. 7C shows peptide mapping results for the isoform-A enriched material.

FIG. 8A shows the percentage of monomers. FIG. 8B shows the percentage of dimers. FIG. 8C shows the percentage of higher order aggregates (HOA).

FIG. 9A shows molar mass of the size variants in the fremanezumab DS. FIG. 9B shows molar mass of the size variants in the isoform control. FIG. 9C shows molar mass of the size variants in the isoform-A enriched material.

FIG. 11A shows the hydrodynamic radius of the fremanezumab DS, isoform control and isoform-A enriched materials over increasing protein concentration. FIG. 11B shows the diffusion coefficient values of the fremanezumab DS, isoform control and isoform-A enriched materials over increasing protein concentration.

FIG. 12A shows particle counts for particles ≥2 μm. FIG. 12B shows particle counts for particles ≥5 μm. FIG. 12C shows particle counts for particles ≥10 μm. FIG. 12D shows particle counts for particles ≥25 μm.

FIG. 16A shows the melting temperature of each sample. FIG. 16B shows the enthalpy as measured for each sample.

FIGS. 17A and 17B show differential scanning calorimetry (DSC) thermograms of the native fractions and fraction mixtures. FIG. 17C shows main peak melting temperature of the native fractions and fraction mixtures. FIG. 17D shows the enthalpy of native fraction and fraction mixtures.

FIG. 18A shows the $\Delta\Delta G$ trend for the first unfolding transition. FIG. 18B shows the $\Delta\Delta G$ trend for the second unfolding transition. FIG. 18C shows the $\Delta\Delta G$ trend for the third unfolding transition.

FIG. 19A shows the percentage of fraction denatured in the fremanezumab DS as compared to isoform-A enriched materials. FIG. 19B shows the percentage of fraction aggregated in the fremanezumab DS as compared to isoform-A enriched materials. FIG. 19C shows the percentage of the fraction of the denatured population that is aggregated in the fremanezumab DS as compared to isoform-A enriched materials.

DETAILED DESCRIPTION

Definitions

Figure 1:
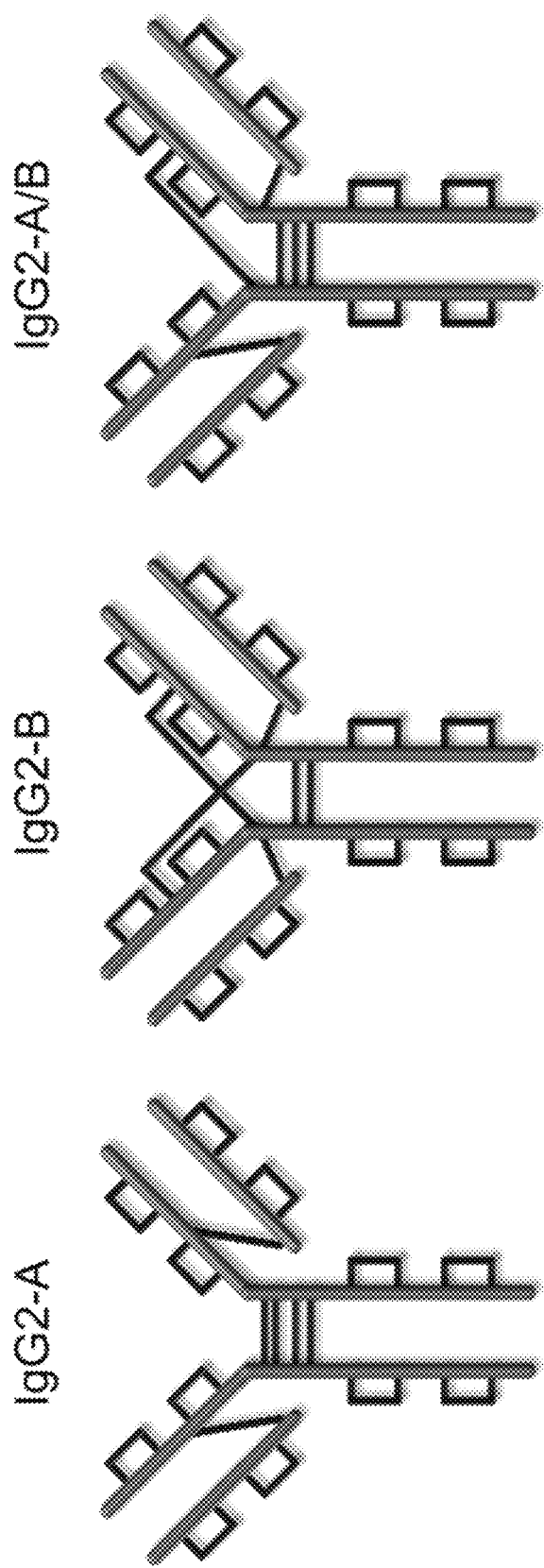
FIG. 1 is a schematic representation of the IgG2-A, IgG2-B, and IgG2-A/B, and disulfide isoforms of the anti-CGRP antagonist antibody fremanezumab.

As used herein, "about" when used in reference to numerical ranges, cutoffs, or specific values is used to indicate that the recited values may vary by up to as much as 10% from the listed value. Thus, the term "about" is used to encompass variations of ±10% or less, variations of ±5% or less, variations of ±1% or less, variations of ±0.5% or less, or variations of ±0.1% or less from the specified value.

An "antibody" or an "antibody molecule" is an immunoglobulin molecule having two full-length heavy chains and two full-length light chains capable of specific binding to a target, such as a carbohydrate, polynucleotide, lipid, polypeptide, etc., through at least one antigen recognition site, located in the variable region of the immunoglobulin molecule. Each light chain and each heavy chain of the antibody has one variable region domain (VL and VH). The variable domains provide antigen specificity, and thus are responsible for antigen recognition. Each variable region contains three complementarity-determining regions (CDRs), named CDR1, CDR2, and CDR3. The three CDRs are non-contiguous along the linear amino acid sequence, but are proximate in the folded protein. As described herein, one of skill in the art knows and can identify the CDRs based on Kabat or Chothia numbering (see, e.g., Kabat et al. (1991) Sequences of Proteins of Immunological Interest, Fifth Edition, U.S. Department of Health and Human Services, NIH Publication No. 91-3242, and Chothia et al. (1987) *J. Mol. Biol.* 196: 901-917).

As used herein, "monoclonal antibody" or "mAb" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

As used herein, the term "buffering agent" refers to those agents which maintain the pH of a solution in a desirable range. Buffering agents include weak acids and their conjugate bases or weak bases and their conjugate acids.

As used herein, the term "calcitonin gene-related peptide" and "CGRP" refers to any form of calcitonin gene-related peptide and variants thereof that retain at least part of the activity of CGRP. For example, CGRP may be α-CGRP or β-CGRP. As used herein, CGRP includes all mammalian species of native sequence CGRP, e.g., human, canine, feline, equine, and bovine.

As used herein, an "anti-CGRP antagonist antibody" or "anti-CGRP antagonist antibody molecule" refers to an antibody that is able to bind to CGRP and inhibit CGRP biological activity and/or downstream pathway(s) mediated by CGRP signaling. An anti-CGRP antagonist antibody encompasses antibodies that modulate, block, antagonize, suppress or reduce (including significantly) CGRP biological activity, or otherwise antagonize the CGRP pathway, including downstream pathways mediated by CGRP signaling, such as receptor binding and/or elicitation of a cellular response to CGRP. For purpose of the present invention, it will be explicitly understood that the term "anti-CGRP antagonist antibody" encompasses all the previously identified terms, titles, and functional states and characteristics whereby CGRP itself, CGRP biological activity (including but not limited to its ability to mediate any aspect of headache), or the consequences of the biological activity, are substantially nullified, decreased, or neutralized in any meaningful degree.

As used herein, the terms "G1," "antibody G1," "TEV-48125" and "fremanezumab" are used interchangeably to refer to an anti-CGRP antagonist antibody produced by expression vectors having deposit numbers of ATCC PTA-6867 and ATCC PTA-6866. The amino acid sequence of the heavy chain and light chain variable regions are shown in SEQ ID NOs: 1 and 2, respectively. The CDR amino acid sequences of the G1 heavy chain variable region are shown in SEQ ID NOs: 7-9 (Kabat and Chothia CDRs are indicated). The CDR amino acid sequences of the G1 light chain variable region are shown in SEQ ID NOs: 10-12. Exemplary polynucleotides encoding the G1 heavy and light chain variable regions are shown in SEQ ID NO: 5 and SEQ ID NO: 6, respectively. The G1 heavy chain full length amino acid sequence is shown in SEQ ID NO: 3. The G1 light chain full length amino acid sequence is shown in SEQ ID NO: 4. Exemplary polynucleotides encoding the G1 full length heavy chain and light chains are shown in SEQ ID NO: 3 and SEQ ID NO: 4, respectively. The characterization of G1 is described in PCT Publication No. WO 2007/054809 and *WHO Drug Information* 30(2): 280-1 (2016), which are hereby incorporated by reference in its entirety.

The term "$k_{on}$," as used herein, refers to the on rate constant for association of an antibody to an antigen to form an antibody/antigen complex.

The term "$k_{off}$," as used herein, refers to the off rate constant for dissociation of an antibody from an antibody/antigen complex.

The term "$K_D$" or "binding affinity," as used herein, refers to the equilibrium constant of an antibody-antigen interaction, and refers to the value obtained in a titration measurement at equilibrium, or by dividing the $k_{off}$ by the $k_{on}$.

The terms "polypeptide," "oligopeptide," "peptide," and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, an "effective dosage" or "effective amount" of drug, compound, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, and/or delaying the progression of the disease of patients. An effective dosage can be administered in one or more administrations. For purposes of this disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably a human. Mammals also include, but are not limited to, farm animals, sport animals, pets, primates, horses, dogs, cats, mice and rats.

General Techniques

The practice of the various aspects of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

A. Pharmaceutical Compositions

In one aspect, the present disclosure provides pharmaceutical compositions including a plurality of IgG2 anti-CGRP antagonist antibody molecules (e.g., fremanezumab) that comprise a high content of the disulfide isoform, IgG2-B. In some embodiments, at least about 70% (e.g., about 71%, about 72%, about 73%, about 74%, about 75%, about 76%, about 77%, about 78%, about 79%, about 80%, about 81%, about 82%, about 83%, about 84%, about 85%, about 90%, about 95%, or more) of the antibody molecules in the pharmaceutical compositions described herein are of the IgG2-B disulfide isoform. In some embodiments, about 72% (±3%) of the antibody molecules in the compositions are of the IgG2-B disulfide isoform. In some embodiments, about 75% (±3%) of the antibody molecules in the compositions are of the IgG2-B disulfide isoform. In some embodiments, about 78% (±3%) of the antibody molecules in the compositions are of the IgG2-B disulfide isoform. The amount of the IgG2-B disulfide isoform in compositions described herein may be determined using the reverse-phase high-performance liquid chromatography (RP-HPLC) method described in Example 1, i.e., a FabRICATOR® RP-HPLC method.

In some embodiments, between about 15% and about 25% (e.g., about 15%, about 16%, about 17%, about 18%, about 19%, about 20%, about 21%, about 22%, about 23%, about 24%, or about 25%) of the antibody molecules in the pharmaceutical compositions described herein are of the IgG2-A/B disulfide isoform. In some embodiments, between about 15% and about 20% of the antibody molecules in the compositions are of the IgG2-A/B disulfide isoform. In some embodiments, between about 20% and about 25% of the antibody molecules in the compositions are of the IgG2-A/B disulfide isoform. In some embodiments, about 20% (±3%) of the antibody molecules in the compositions are of the IgG2-A/B disulfide isoform. In some embodiments, about 22% (±3%) of the antibody molecules in the compositions are of the IgG2-A/B disulfide isoform. In some embodiments, about 24% (±3%) of the antibody molecules in the compositions are of the IgG2-A/B disulfide isoform. In some embodiments, about 26% (±3%) of the antibody molecules in the compositions are of the IgG2-A/B disulfide isoform. In some embodiments, about 28% (±3%) of the antibody molecules in the compositions are of the IgG2-A/B disulfide isoform. In some embodiments, about 30% (±3%) of the antibody molecules in the compositions are of the IgG2-A/B disulfide isoform. In some embodiments, at least about 20% (±3%) of the antibody molecules in the compositions are of the IgG2-A/B disulfide isoform. In some embodiments, at least about 22% (±3%) of the antibody molecules in the compositions are of the IgG2-A/B disulfide isoform. In some embodiments, at least about 24% (±3%) of the antibody molecules in the compositions are of the IgG2-A/B disulfide isoform. In some embodiments, at least about 26% (±3%) of the antibody molecules in the compositions are of the IgG2-A/B disulfide isoform. In some embodiments, at least about 28% (±3%) of the antibody molecules in the compositions are of the IgG2-A/B disulfide isoform. In some embodiments, at least about 30% (±3%) of the antibody molecules in the compositions are of the IgG2-A/B disulfide isoform.

In some embodiments, between about 3% and about 7% of the antibody molecules in the pharmaceutical compositions described herein are of the IgG2-A disulfide isoform. In some embodiments, between about 4% and about 6% of the antibody molecules in the compositions are of the IgG2-A disulfide isoform. In some embodiments, about 3% (±3%) of the antibody molecules in the compositions are of the IgG2-A disulfide isoform. In some embodiments, about 4% (±3%) of the antibody molecules in the compositions are of the IgG2-A disulfide isoform. In some embodiments, about 5% (±3%) of the antibody molecules in the compositions are of the IgG2-A disulfide isoform. In some embodiments, about 6% (±3%) of the antibody molecules in the compositions are of the IgG2-A disulfide isoform. In some embodiments, about 7% (±3%) of the antibody molecules in the compositions are of the IgG2-A disulfide isoform. In some embodiments, at least about 3% (±3%) of the antibody molecules in the compositions are of the IgG2-A disulfide isoform. In some embodiments, at least about 4% (±3%) of the antibody molecules in the compositions are of the IgG2-A disulfide isoform. In some embodiments, at least about 5% (±3%) of the antibody molecules in the compositions are of the IgG2-A disulfide isoform. In some embodiments, at least about 6% (±3%) of the antibody molecules in the compositions are of the IgG2-A disulfide isoform. In some embodiments, at least about 7% (±3%) of the antibody molecules in the compositions are of the IgG2-A disulfide isoform.

In some embodiments, the pharmaceutical compositions described herein include a plurality of IgG2 monoclonal antibody molecules, wherein between about 70% and about 80% of the antibody molecules in the composition are of the IgG-2B disulfide isoform; wherein between about 3% and about 7% of the antibody molecules in the composition are of the IgG2-A disulfide isoform; and wherein between about 15% and about 25% of the antibody molecules in the composition are of the disulfide isoform A/B. In some embodiments, about 72% (±3%) of the antibody molecules in the composition are of the IgG2-B disulfide isoform, about 22% (±3%) of the antibody molecules in the composition are of the IgG2-A/B disulfide isoform, and about 6% (±3%) of the antibody molecules in the composition are of the IgG2-A disulfide isoform.

Without wishing to be bound by theory, it is believed that pharmaceutical compositions comprising a high content of the IgG2-B disulfide isoform are particularly advantageous since this disulfide isoform is more stable than the IgG2-A/B and IgG2-A disulfide isoforms.

Without wishing to be bound by theory, fremanezumab preparations comprising a high content of the IgG2-B disulfide isoform are particularly advantageous for meeting the product quality attributes as a commercial drug product, including but not limited to: size heterogeneity, sub-visible particle count, and syringe functionality.

In some embodiments, the antibody molecules in the pharmaceutical compositions described herein comprise a heavy chain comprising CDR H3 amino acid sequence as set forth in SEQ ID NO: 9. In some embodiments, the antibody molecules comprise a heavy chain comprising CDR H2 amino acid sequence as set forth in SEQ ID NO: 8. In some embodiments, the antibody molecules comprise a heavy chain comprising CDR H1 amino acid sequence as set forth in SEQ ID NO: 7. In some embodiments, the antibody molecules in the pharmaceutical compositions described herein comprise a heavy chain, wherein the heavy chain comprises a CDR H3 amino acid sequence as set forth in SEQ ID NO: 9, a CDR H2 amino acid sequence as set forth in SEQ ID NO: 8, and a CDR H1 amino acid sequence as set forth in SEQ ID NO: 7.

In some embodiments, the antibody molecules in the pharmaceutical compositions described herein comprise a light chain comprising CDR L3 amino acid sequence as set forth in SEQ ID NO: 12. In some embodiments, the antibody molecules comprise a light chain comprising CDR L2 amino acid sequence as set forth in SEQ ID NO: 11. In some embodiments, the antibody molecules comprise a light chain comprising CDR L1 amino acid sequence as set forth in SEQ ID NO: 10. In some embodiments, the antibody molecules in the pharmaceutical compositions described herein comprise a light chain, wherein the light chain comprises a CDR L3 amino acid sequence as set forth in SEQ ID NO: 12, a CDR L2 amino acid sequence as set forth in SEQ ID NO: 11, and a CDR L1 amino acid sequence as set forth in SEQ ID NO: 10.

In some embodiments, the antibody molecules in the pharmaceutical compositions described herein comprise a heavy chain and a light chain, wherein the heavy chain comprises a CDR H3 amino acid sequence as set forth in SEQ ID NO: 9, a CDR H2 amino acid sequence as set forth in SEQ ID NO: 8, and a CDR H1 amino acid sequence as set forth in SEQ ID NO: 7, and wherein the light chain comprises a CDR L3 amino acid sequence as set forth in SEQ ID NO: 12, a CDR L2 amino acid sequence as set forth in SEQ ID NO: 11, and a CDR L1 amino acid sequence as set forth in SEQ ID NO: 10.

In some embodiments, the antibody molecules in the pharmaceutical compositions described herein comprise a heavy chain variable region amino acid sequence having at least 85%, 86%, 87%, 88%, 89%, 90%, 91%, 92%, 93%, 94%, 95%, 96%, 97%, 98%, 99%, or 100% identity to the heavy chain variable region amino acid sequence as set forth in SEQ ID NO: 1. In some embodiments, the antibody molecules in the compositions comprise a heavy chain variable region comprising or consisting of the amino acid sequence as set forth in SEQ ID NO: 1.

In some embodiments, the antibody molecules in the pharmaceutical compositions described herein comprise a light chain variable region amino acid sequence having at least 85%, 86%, 87%, 88%, 89%, 90%, 91%, 92%, 93%, 94%, 95%, 96%, 97%, 98%, 99%, or 100% identity to the light chain variable region amino acid sequence as set forth in SEQ ID NO: 2. In some embodiments, the antibody molecules in the compositions comprise a light chain variable region comprising or consisting of the amino acid sequence as set forth in SEQ ID NO: 2.

In some embodiments, the antibody molecules in the pharmaceutical compositions described herein comprise a heavy chain and a light chain, wherein the heavy chain comprises a variable region amino acid sequence having at least 85%, 86%, 87%, 88%, 89%, 90%, 91%, 92%, 93%, 94%, 95%, 96%, 97%, 98%, 99%, or 100% identity to the heavy chain variable region amino acid sequence as set forth in SEQ ID NO: 1, and wherein the light chain comprises a variable region amino acid sequence having at least 85%, 86%, 87%, 88%, 89%, 90%, 91%, 92%, 93%, 94%, 95%, 96%, 97%, 98%, 99%, or 100% identity to the light chain variable region amino acid sequence as set forth in SEQ ID NO: 2.

In some embodiments, the antibody molecules in the pharmaceutical compositions described herein include a heavy chain having a modified CH2 domain, wherein the modified CH2 domain is IgG2Δa (SEQ ID NO: 15) (see, e.g., U.S. Pat. No. 7,597,889 B1, incorporated herein by reference). In some embodiments, the antibody molecules in the pharmaceutical compositions described herein include a heavy chain comprising or consisting of an amino acid sequence having at least 85%, 86%, 87%, 88%, 89%, 90%, 91%, 92%, 93%, 94%, 95%, 96%, 97%, 98%, 99%, or 100% identity to the heavy chain amino acid sequence as set forth in SEQ ID NO: 3. In some embodiments, the antibody molecules include a heavy chain comprising or consisting of the amino acid sequence of SEQ ID NO: 3.

In some embodiments, the antibody molecules in the pharmaceutical compositions described herein include a light chain comprising or consisting of an amino acid sequence having at least 85%, 86%, 87%, 88%, 89%, 90%, 91%, 92%, 93%, 94%, 95%, 96%, 97%, 98%, 99%, or 100% identity to the light chain amino acid sequence as set forth in SEQ ID NO: 4. In some embodiments, the antibody molecules include a light chain comprising or consisting of the amino acid sequence of SEQ ID NO: 4.

In some embodiments, the antibody molecules in the pharmaceutical compositions described herein comprise both a heavy chain and a light chain, wherein the heavy chain comprises or consists of an amino acid sequence having at least 85%, 86%, 87%, 88%, 89%, 90%, 91%, 92%, 93%, 94%, 95%, 96%, 97%, 98%, 99%, or 100% identity to the heavy chain amino acid sequence as set forth in SEQ ID NO: 3, and wherein the light chain comprises or consists of an amino acid sequence having at least 85%, 86%, 87%, 88%, 89%, 90%, 91%, 92%, 93%, 94%, 95%, 96%, 97%, 98%, 99%, or 100% identity to the light chain amino acid sequence as set forth in SEQ ID NO: 4.

Methods for detecting the amount and/or distribution of specific IgG2 disulfide isoforms present in a preparation are known in the art, and include reverse-phase high-performance liquid chromatography (RP-HPLC) (see, e.g., U.S. Publication No. 2005/0161399 A1; Dillon et al. (2008) *J. Biol. Chem.* 283(23): 16206-215; and Wypych et al. (2008) *J. Biol. Chem.* 283(23): 16194-205, each of which is incorporated herein by reference).

In some embodiments, the pharmaceutical compositions described herein are liquid compositions (e.g., an aqueous liquid composition) and the antibody (e.g., fremanezumab) concentration in the compositions is from about 0.1 mg/mL to about 500 mg/mL, from about 0.1 to about 375 mg/mL, from about 0.1 to about 250 mg/mL, from about 0.1 to about 175 mg/mL, from about 0.1 to about 100 mg/mL, from about 1 mg/mL to about 500 mg/mL, from about 1 mg/mL to about 375 mg/mL, from about 1 mg/mL to about 300 mg/mL, from about 1 mg/mL to about 250 mg/mL, from about 1 mg/mL to about 200 mg/mL, from about 1 mg/mL to about 150 mg/mL, from about 1 mg/mL to about 100 mg/mL, from about 10 mg/mL to about 500 mg/mL, from about 10 mg/mL to about 375 mg/mL, from about 10 mg/mL to about 250 mg/mL, from about 10 mg/mL to about 150 mg/mL, from about 10 mg/mL to about 100 mg/mL, from about 100 mg/mL to about 500 mg/mL, from about 100 mg/mL to about 450 mg/mL, from about 100 mg/mL to about 400 mg/mL, from about 100 mg/mL to about 350 mg/mL, from about 100 mg/mL to about 300 mg/mL, from about 100 mg/mL to about 250 mg/mL, from about 100 mg/mL to about 200 mg/mL, from about 100 mg/mL to about 150 mg/mL. In some embodiments, the pharmaceutical compositions include an antibody concentration of about 100 mg/mL (±15 mg/mL). In some embodiments, the pharmaceutical compositions include an antibody concentration of about 150 mg/mL (±15 mg/mL). In some embodiments, the pharmaceutical compositions include an antibody concentration of about to 200 mg/mL (±15 mg/mL). In some embodiments, the pharmaceutical compositions include an antibody concentration of about to 220 mg/mL (±15 mg/mL). In some embodiments, the pharmaceutical compositions described herein are liquid compositions and the antibody (e.g., fremanezumab) concentration in the compositions is from about 0.1 mM to about 1.5 mM, from about 0.1 mM to about 1 mM, from about 0.5 mM to about 1.5 mM, from about 0.9 mM to about 1.1 mM. In some the pharmaceutical compositions described herein are liquid compositions and the antibody (e.g., fremanezumab) concentration in the compositions is about 0.1 mM, about 0.15 mM, about 0.2 mM, about 0.25 mM, about 0.3 mM, about 0.35 mM, about 0.4 mM, about 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, about 1.0 mM, about 1.1 mM, about 1.15 mM, about 1.2 mM, about 1.25 mM, about 1.3 mM, about 1.35 mM, about 1.4 mM, about 1.45 mM, or about 1.5 mM. In some embodiments, the pharmaceutical compositions are liquid compositions and include about 1.0 mM fremanezumab. In some embodiments, the pharmaceutical compositions described herein are liquid compositions and the antibody (e.g., fremanezumab) concentration in the composition is from about 0.1% (w/v) to about 50% (w/v), from about 0.1% (w/v) to about 37.5% (w/v), from about 0.1% (w/v) to about 25% (w/v), from about 0.1% (w/v) to about 17.5% (w/v), from about 0.1% (w/v) to about 10% (w/v), from about 1.0% (w/v) to about 30% (w/v), from about 1.0% (w/v) to about 25.0% (w/v), from about 1.0% (w/v) to about 20% (w/v), from about 1.0% (w/v) to about 15.0% (w/v), from about 1.0% (w/v) to about 10% (w/v). In some embodiments, the pharmaceutical compositions described herein are liquid compositions and antibody (e.g., fremanezumab) concentration in the composition (e.g., polysorbate 80) is about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), or about 20% (w/v). In some embodiments, the pharmaceutical compositions described herein are liquid compositions and include 15% (w/v) fremanezumab.

In some embodiments, 90% of the antibody molecules present in the pharmaceutical compositions described herein are monomeric. In some embodiments, ≥95% of the antibody molecules present in the pharmaceutical compositions described herein are monomeric. For example, in some embodiments, at least about 95%, 96%, 97%, 98%, 99%, or 100% of the antibody molecules present in the pharmaceutical composition are monomeric. In some embodiments, ≤5.0% (e.g., ≤4.5%, ≤4.0%, ≤3.5%, ≤3.0%, ≤2.5%, ≤2.0%, ≤1.5%, ≤1.0%, ≤0.5%, or less) of the antibody molecules present in the pharmaceutical composition are dimeric. In some embodiments, ≤3.5% of the antibody molecules present in the pharmaceutical composition are dimeric. In some embodiments ≤1.0% (e.g., 1.0%, 0.9%, 0.8%, 0.7%, 0.6%, 0.5%, 0.4%, 0.3%, 0.2%, 0.1%, or less) of the antibody molecules present in the pharmaceutical composition are in the form of higher order aggregates. The monomer and aggregate content (e.g., dimers, trimers, tetramers, pentamers, oligomers, or higher order aggregates) in a pharmaceutical composition can be measured using any method known in the art including, for example, high performance size exclusion chromatography (HP-SEC), analytical ultracentrifugation, dynamic light scattering, multi-angle laser light scattering (MALLs).

In some embodiments, from about 45% to about 85% of the antibody molecules (e.g., fremanezumab) in the pharmaceutical compositions described herein are of major charge isoform (also known as the major charge variant or main peak). For example, in some embodiments, from about 50% to about 80%, from about 55% to about 75%, from about 60% to about 75%, or from about 65% to about 75% of the antibody molecules in the pharmaceutical composition are of the major charge isoform. In some embodiments, about 65%, 66%, 67%, 68%, 69%, 70%, 71%, 72%, 73%, 74%, 75%, 76%, 77%, 78%, 79%, 80%, 81%, 82%, 83%, 84%, or 85% of the antibody molecules in the pharmaceutical composition are of the major charge isoform. In some embodiments, from about 10% to about 35% of the antibody molecules (e.g., fremanezumab) in the pharmaceutical composition are of the acidic charge isoform. For example, in some embodiments, from about 15% to about 30%, from about 20% to about 25%, from about 20% to about 30%, or from about 20% to about 35% of the antibody molecules in the pharmaceutical composition are of the acidic charge isoform. In some embodiments, about 15%, 16%, 17%, 18%, 19%, 20%, 21%, 22%, 23%, 24%, 25%, 26%, 27%, 28%, 29%, or 30% of the antibody molecules in the pharmaceutical composition are of the acidic charge isoforms. In some embodiments, from about 0% to about 35% of the antibody molecules (e.g., fremanezumab) in the pharmaceutical composition are of the basic charge isoform. For example, in some embodiments, from about 5% to about 30%, from about 10% to about 25%, from about 15% to about 20%, from about 15% to about 25%, from about 10% to about 20% or from about 5% to about 10% of the antibody molecules in the pharmaceutical composition are of the basic charge isoform. In some embodiments, about 1%, 2%, 3%, 4%, 5%, 6%, 7%, 8%, 9%, 10%, 15%, 20%, 25%, or 30% of the antibody molecules in the pharmaceutical composition are of the basic charge isoform. In some embodiments, about 72%±3% of the antibody molecules in the pharmaceutical composition are of the major charge isoform, about 22%±3% of the antibody molecules in the pharmaceutical composition are of the acidic charged isoform, and about 5%±3% of the antibody molecules in the pharmaceutical composition are of the basic charge isoform. The amount or distribution of major, acidic, or basic charge isoforms of antibody molecules in a pharmaceutical composition can be measured using any charge based-separation technique known in the art including, for example, isoelectric focusing (IEF) gel electrophoresis, capillary isoelectric focusing (cIEF) gel electrophoresis, cation exchange chromatography (CEX), anion exchange chromatography (AEX), preparative ion exchange chromatography coupled with reverse-phase liquid chromatography with mass spectrometry analysis, and mixed mode ion exchange chromatography using volatile salts and coupled with on-line to native mass spectrometry (see, e.g., Du et al. (2012) MAbs 4(5): 578-85; and Leblanc et al. (2017) *J. Chromatogr. B Analyt. Technol. Biomed. Life Sci.* 1048: 130-9.

The pharmaceutical compositions described herein can include one or more pharmaceutically acceptable excipients. Suitable pharmaceutically acceptable excipients for liquid and solid pharmaceutical compositions are known in the art (see, e.g., Remington: The Science and Practice of Pharmacy 20th Ed. (2000) Lippincott Williams and Wilkins, Ed. K. E. Hoover; Remington's Pharmaceutical Sciences and U.S. Pharmacopeia: National Formulary, Mack Publishing Company, Easton, Pa. (1984); Hardman et al. (2001) Goodman and Gilman's The Pharmacological Basis of Therapeutics, McGraw-Hill, New York, N.Y.; Avis et al. (eds.) (1993) Pharmaceutical Dosage Forms: Parenteral Medications, Marcel Dekker, NY; Lieberman et al. (eds.) (1990) Pharmaceutical Dosage Forms: Tablets, Marcel Dekker, NY; Lieberman et al. (eds.) (1990) Pharmaceutical Dosage Forms: Disperse Systems, Marcel Dekker, NY; Weiner, Wang (1999) *Int. J. Pharm.* 185: 129-188; Wang (2000) *Int. J. Pharm.* 203: 1-60; Kotkoskie (2000) Excipient Toxicity and Safety, Marcel Dekker, Inc., New York, N.Y.;). For example, acceptable excipients are preferably non-toxic to recipient subjects at the dosages and concentrations employed.

Pharmaceutical compositions described herein may include one or more pharmaceutically acceptable excipients, such as, but not limited to, buffers such as phosphate, citrate, and other organic acids; salts such as sodium chloride; antioxidants including ascorbic acid and methionine; preservatives (such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol); low molecular weight (less than about 10 residues) polypeptides; proteins, such as serum albumin and gelatin; hydrophilic polymers such as polyvinylpyrrolidone; amino acids such as glycine, glutamine, methionine, asparagine, histidine, arginine, lysine, and combinations thereof; monosaccharides, disaccharides, and other carbohydrates including glucose, mannose, dextrins, and combinations thereof; chelating agents, such as ethylenediaminetetraacetic acid (EDTA) and diethylenetriaminepentaacetic acid (DTPA), or salts thereof (e.g., disodium EDTA dihydrate); sugars or sugar alcohols such as sucrose, mannitol, trehalose, sorbitol, and combinations thereof; salt-forming counter-ions such as sodium; metal complexes (e.g., Zn-protein complexes); and/or non-ionic surfactants such as Tween™, polysorbate (e.g., polysorbate 20, polysorbate 40, polysorbate 60, polysorbate 80), Pluronics™, polyethylene glycol (PEG), and combinations thereof.

In some embodiments, the pharmaceutical compositions described herein include a sugar (e.g., a non-reducing sugar) or a sugar alcohol. Exemplary sugars and sugar alcohols include sorbitol, sucrose, trehalose (e.g., trehalose dihydrate), and mannitol. In some embodiments, the pharmaceutical composition is liquid, and the sugar or sugar alcohol is present in the pharmaceutical composition at a concentration of from about 1 mg/mL to about 500 mg/mL, from about 10 mg/mL to about 200 mg/mL, from about 10 mg/mL to about 100 mg/mL, or from about 50 mg/mL to about 150 mg/mL. In some embodiments, the sugar (e.g., sucrose) or sugar alcohol is present in the pharmaceutical composition at a concentration of from about 65 mg/mL to about 90 mg/mL. For example, in some embodiments, the pharmaceutical composition is liquid, and the sugar or sugar alcohol (e.g., sucrose or trehalose) is present in the pharmaceutical composition at a concentration of about 65 mg/mL, 66 mg/mL, 67 mg/mL, 68 mg/mL, 69 mg/mL, 70 mg/mL, 71 mg/mL, 72 mg/mL, 73 mg/mL, 74 mg/mL, 75 mg/mL, 76 mg/mL, 77 mg/mL, 78 mg/mL, 79 mg/mL, 80 mg/mL, 81 mg/mL, 82 mg/mL, 83 mg/mL, 84 mg/mL, 85 mg/mL, 86 mg/mL, 87 mg/mL, 88 mg/mL, 89 mg/mL, or 90 mg/mL. In some embodiments, the pharmaceutical composition is liquid and includes about 66 mg/mL sucrose. In some embodiments, the pharmaceutical composition is liquid and includes a concentration of sugar (e.g., sucrose) or sugar alcohol of from about 0.5% (w/v) to about 10% (w/v), from about 1.0% (w/v) to about 10% (w/v), from about 5.0% (w/v) to about 10.0% (w/v), or from about 5.0% (w/v) to about 7.0% (w/v). In some embodiments, the pharmaceutical composition is liquid and includes a concentration of sugar (e.g., sucrose) or sugar alcohol of about 1.0% (w/v), about 2.0% (w/v), about 3.0% (w/v), about 4.0% (w/v), about 5.0% (w/v), about 6.0% (w/v), about 7.0% (w/v), about 8.0% (w/v), about 9.0% (w/v), about 10.0% (w/v). In some embodiments, the pharmaceutical composition is liquid and includes a concentration of sugar (e.g., sucrose) or sugar alcohol of about 6.1% (w/v), about 6.2% (w/v), about 6.3% (w/v), about 6.4% (w/v), about 6.5% (w/v), about 6.6% (w/v), about 6.7% (w/v), about 6.8% (w/v), about 6.9% (w/v), or about 7.0% (w/v). In some embodiments, the pharmaceutical composition is liquid and includes about 6.6% (w/v) sucrose.

In some embodiments, the pharmaceutical composition is a liquid and includes a concentration of sugar (e.g., sucrose) or sugar alcohol of from about 10 mM to about 1.0 M, from about 50 mM to about 1.0 M, from about 100 mM to about 0.5 M, or from about 150 mM to about 200 mM. In some embodiments, the pharmaceutical composition is a liquid and includes a concentration of sugar (e.g., sucrose) or sugar alcohol of about 100 mM, about 150 mM, about 200 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, or about 1.0 M. In some embodiments the pharmaceutical composition is a liquid and includes about 190 mM, about 191 mM, about 192 mM, about 193 mM, about 194 mM, about 195 mM, about 196 mM, about 198 mM, about 199 mM, or about 200 mM sucrose. In some embodiments, the pharmaceutical composition is liquid and includes about 193 mM sucrose.

In some embodiments, the pharmaceutical compositions described herein include a chelating agent. Exemplary chelating agents include EDTA and diethylenetriaminepentaacetic acid (DTPA). In some embodiments, the pharmaceutical composition is liquid and includes a concentration of chelating agent (e.g., EDTA) of from about 0.001 mg/mL to about 1 mg/mL, from about 0.001 mg/mL to about 0.1 mg/mL, or from about 0.001 mg/mL to about 0.01 mg/mL. In some embodiments, the pharmaceutical composition is liquid and includes a concentration of chelating agent (e.g., EDTA disodium dihydrate) of about 0.01 mg/mL, about 0.02 mg/mL, about 0.03 mg/mL, about 0.04 mg/mL, about 0.05 mg/mL, about 0.06 mg/mL, about 0.07 mg/mL, about 0.08 mg/mL, about 0.09 mg/mL, about 0.10 mg/mL, about 0.11 mg/mL, about 0.12 mg/mL, about 0.13 mg/mL, about 0.14 mg/mL, about 0.15 mg/mL, about 0.16 mg/mL, about 0.17 mg/mL, about 0.18 mg/mL, about 0.19 mg/mL, or about 0.20 mg/mL. In some embodiments, the pharmaceutical composition is liquid and includes a concentration of chelating agent (e.g., EDTA disodium dihydrate) of from about 0.001% (w/v) to about 1% (w/v), from about 0.001% (w/v) to about 1% (w/v), from about 0.001% (w/v) to about 0.1%

(w/v), or from about 0.001% (w/v) to about 0.01% (w/v). In some embodiments, the pharmaceutical composition is liquid and includes a concentration of chelating agent (e.g., EDTA disodium dihydrate) of about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.10% (w/v), about 0.11% (w/v), about 0.12% (w/v), about 0.13% (w/v), about 0.14% (w/v), about 0.15% (w/v), about 0.16% (w/v), about 0.17% (w/v), about 0.18% (w/v), about 0.19% (w/v), or about 0.20% (w/v). In some embodiments, the pharmaceutical composition is a liquid and includes a concentration of chelating agent (e.g., EDTA disodium dihydrate) of about 0.010% (w/v) about 0.011% (w/v), about 0.012% (w/v), about 0.013% (w/v), about 0.014% (w/v), about 0.015% (w/v), about 0.016% (w/v), about 0.017% (w/v), about 0.018% (w/v), about 0.019% (w/v), or about 0.020% (w/v). In some embodiments, the pharmaceutical composition is a liquid and includes a concentration of chelating agent (e.g., EDTA disodium dihydrate) of from about 0.01 mM to about 1.0 mM, from about 0.1 mM to about 1.0 mM, from about 0.1 mM to about 0.5 mM, or from about 0.1 mM to about 0.4 mM. In some embodiments, the pharmaceutical composition is a liquid and includes a concentration of chelating agent (e.g., EDTA disodium dihydrate) of about 0.1 mM, about 0.15 mM, about 0.2 mM, about 0.25 mM, about 0.3 mM, about 0.35 mM, about 0.4 mM, about 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, or about 1.0 mM. In some embodiments the pharmaceutical composition is a liquid and includes about 0.37 mM EDTA disodium dihydrate.

In some embodiments, the pharmaceutical compositions described herein include a surfactant. Exemplary surfactants include non-ionic surfactants such as Tween™, polysorbate (e.g., polysorbate 20, polysorbate 40, polysorbate 60, polysorbate 80), Pluronics™, and polyethylene glycol (PEG). In some embodiments, the surfactant is a polysorbate. In some embodiments, the surfactant is polysorbate 80. In some embodiments, the pharmaceutical composition is liquid and includes a concentration of surfactant (e.g., polysorbate 80) of from about 0.01 mg/mL to about 10 mg/mL, from about 0.01 mg/mL to about 1 mg/mL, from about 0.1 mg/mL to about 1 mg/mL, or from about 0.01 mg/mL to about 0.5 mg/mL. In some embodiments, the pharmaceutical composition includes a surfactant (e.g., polysorbate 80) at a concentration of about 0.10 mg/mL, about 0.15 mg/mL, about 0.2 mg/mL, about 0.25 mg/mL, about 0.3 mg/mL, about 0.35 mg/mL, about 0.4 mg/mL, about 0.45 mg/mL, or about 0.5 mg/mL. In some embodiments, the pharmaceutical composition includes a surfactant (e.g., polysorbate 80) at a concentration of about 0.1 mg/mL. In some embodiments, the pharmaceutical composition includes a surfactant (e.g., polysorbate 80) at a concentration of about 0.15 mg/mL. In some embodiments, the pharmaceutical composition includes a surfactant (e.g., polysorbate 80) at a concentration of about 0.2 mg/mL. In some embodiments, the pharmaceutical composition includes a surfactant (e.g., polysorbate 80) at a concentration of about 0.25 mg/mL. In some embodiments, the pharmaceutical composition includes a surfactant (e.g., polysorbate 80) at a concentration of about 0.3 mg/mL. In some embodiments, the pharmaceutical composition is a liquid and includes a surfactant (e.g., polysorbate 80) at a concentration of from about 0.001% (w/v) to about 1% (w/v), from about 0.01% (w/v) to about 0.5% (w/v), from about 0.01% (w/v) to about 0.1% (w/v), or from about 0.1% (w/v) to about 0.5% (w/v). In some embodiments, the pharmaceutical composition is liquid and includes a concentration of a surfactant (e.g., polysorbate 80) of about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v), about 0.10% (w/v), about 0.11% (w/v), about 0.12% (w/v), about 0.13% (w/v), about 0.14% (w/v), about 0.15% (w/v), about 0.16% (w/v), about 0.17% (w/v), about 0.18% (w/v), about 0.19% (w/v), or about 0.20% (w/v). In some embodiments, the pharmaceutical composition is a liquid and includes 0.02% (w/v) polysorbate 80. In some embodiments, the pharmaceutical composition is a liquid and includes a concentration of a surfactant (e.g., polysorbate 80) of from about 0.01 mM to about 1.0 mM, from about 0.1 mM to about 1.0 mM, from about 0.1 mM to about 0.5 mM, or from about 0.1 mM to about 0.4 mM. In some embodiments, the pharmaceutical composition is a liquid and includes a concentration of a surfactant (e.g., polysorbate 80) of about 0.1 mM, about 0.15 mM, about 0.2 mM, about 0.25 mM, about 0.3 mM, about 0.35 mM, about 0.4 mM, about 0.45 mM, about 0.5 mM, about 0.55 mM, about 0.6 mM, about 0.65 mM, about 0.7 mM, about 0.75 mM, about 0.8 mM, about 0.85 mM, about 0.9 mM, about 0.95 mM, or about 1.0 mM. In some embodiments the pharmaceutical composition is a liquid and includes about 0.15 mM polysorbate 80.

In some embodiments, the pharmaceutical compositions describe herein include a buffering agent. A buffering agent generally includes an acid and its conjugate base to achieve a desired pH. The overall pH of the pharmaceutical composition comprising a buffering agent is generally a reflection of the equilibrium concentration of each of the relevant buffering agents in the composition. Various buffering agents can be employed depending, for example, on the desired pH of the pharmaceutical composition. In some embodiments, the buffering agent includes an amino acid such as histidine, arginine, glycine, or asparagine. In some embodiments, the buffering agent includes histidine. For example, in some embodiments, the buffering agent includes or consists of a combination of L-histidine and L-histidine hydrochloride monohydrate. In some embodiments, the pharmaceutical composition is a liquid and includes a buffering agent (e.g., consisting of an acid and its conjugate base) at a concentration of from about 0.1 mM to about 100 mM, from about 0.1 mM to about 1 mM, from about 0.01 mM to about 50 mM, from about 1 mM to about 50 mM, from about 1 mM to about 30 mM, from about 1 mM to about 20 mM, or from about 10 mM to about 25 mM. In some embodiments, the pharmaceutical composition is a liquid, and includes a buffering agent (e.g., consisting of an acid and its conjugate base (e.g., L-histidine and L-histidine hydrochloride monohydrate)), at a concentration of about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, or about 25 mM. In some embodiments, the pharmaceutical composition is a liquid and includes 3.5 mM L-histidine and 12.5 mM L-histidine hydrochloride monohydrate. In some embodiments, the pharmaceutical composition is a liquid and includes a concentration of a buffering agent (e.g., including both an acid and its conjugate base (e.g., L-histidine and L-histidine hydrochloride monohydrate)) of from about 0.001% (w/v) to about 1% (w/v), from about 0.01% (w/v) to about 0.5% (w/v), from about 0.01% (w/v) to about 0.1% (w/v), or from about 0.1% (w/v) to about 0.5% (w/v). In some embodiments, the pharmaceutical composition is liquid and includes a concentration of a buffering agent (e.g., including both an acid and its conjugate base (e.g., L-histidine and L-histidine hydrochloride monohydrate)) of about 0.1% (w/v), about 0.2% (w/v), about 0.3% (w/v), about 0.4% (w/v), about 0.5% (w/v), about 0.6% (w/v), about 0.7% (w/v), about 0.8% (w/v), about 0.9% (w/v), about 1.0% (w/v). In some embodiments, the pharmaceutical composition is liquid and includes a concentration of a buffering agent (e.g., including both an acid and its conjugate base (e.g., L-histidine and L-histidine hydrochloride monohydrate)) of from about 0.1 mg/mL to about 10 mg/mL, from about 1.0 mg/mL to about 10.0 mg/mL, from about 1.0 mg/mL to about 5.0 mg/mL, or from about 2.5 mg/mL to about 5.0 mg/mL. In some embodiments, the pharmaceutical composition is a liquid and includes a buffering agent (e.g., including both an acid and its conjugate base (e.g., L-histidine and L-histidine hydrochloride monohydrate)) at a concentration of about 1.0 mg/mL, about 1.5 mg/mL, about 2.0 mg/mL, about 2.5 mg/mL, about 3.0 mg/mL, about 3.5 mg/mL, about 4.0 mg/mL, about 4.5 mg/mL, or about 5.0 mg/mL.

In some embodiments, the pharmaceutical compositions described herein may have any suitable pH for therapeutic efficacy, safety and/or storage. For example, the pH of a liquid pharmaceutical composition may be from about 4 to about 9, from about 5 to about 8, from about 5 to about 6, from about 5 to about 7, or from about 6 to about 8. In some embodiments, a pharmaceutical composition described herein has a pH of about 3.0, about 3.5, about 4.0, about 4.5, about 5.0, about 5.5, about 6.0, about 6.5, about 7.0, about 7.5, about 8.0, about 8.5, about 9.0, about 9.5 or about 10 (or the pH of the pharmaceutical composition may be higher or lower). In some embodiments, a pharmaceutical composition described herein has a pH of from about 5 to about 6 (e.g., 5.0, 5.1, 5.2, 5.3, 5.4, 5.5, 5.6, 5.7, 5.8, 5.9, or 6.0). In some embodiments, a pharmaceutical composition described herein has a pH of about 5.0±0.3. In some embodiments, a pharmaceutical composition described herein has a pH of about 5.5±0.3. In some embodiments, a pharmaceutical composition described herein has a pH of about 6.0±0.3. In some embodiments, a pharmaceutical composition described herein has a pH of about 6.5±0.3.

In some embodiments, a liquid pharmaceutical composition comprises about 150 mg/mL (±15 mg/mL) of fremanezumab, about 16 mM histidine, about 66 mg/mL sucrose, about 0.136 mg/mL EDTA disodium dihydrate, and about 0.2 mg/ml polysorbate 80, at a pH of about 5.5±0.3, wherein at least about 70% of the fremanezumab in the composition is of the IgG2-B disulfide isoform. In some embodiments, a liquid pharmaceutical composition comprises about 150 mg/mL (±15 mg/mL) of fremanezumab, about 0.54 mg/mL L-histidine, about 2.62 mg/mL L-histidine hydrochloride monohydrate, about 66 mg/mL sucrose, about 0.136 mg/mL EDTA disodium dihydrate, and about 0.2 mg/ml polysorbate 80, at a pH of about 5.5±0.3, wherein at least about 70% of the fremanezumab in the composition is of the IgG2-B disulfide isoform. In some embodiments, a liquid pharmaceutical composition comprises about 225 mg of fremanezumab, about 0.82 mg of L-histidine, about 3.93 mg of L-histidine hydrochloride monohydrate, about 99 mg of sucrose, about 0.20 mg of EDTA disodium dehydrate, and about 0.3 mg of polysorbate 80, at a pH of about 5.5±0.3, wherein at least about 70% of the fremanezumab in the composition is of the IgG2-B disulfide isoform. In a further embodiment, the volume of the liquid pharmaceutical composition is about 1.5 mL.

In some embodiments, the liquid pharmaceutical composition is a solution, e.g., supplied in a single-dose 225 mg/1.5 mL prefilled syringe. Each prefilled syringe can deliver 1.5 mL of solution containing 225 mg fremanezumab, 0.204 mg disodium ethylenediaminetetraacetic acid dihydrate (EDTA), 0.815 mg L-histidine, 3.93 mg L-histidine hydrochloride monohydrate, 0.3 mg polysorbate-80, 99 mg sucrose, and water for injection, at a pH of 5.5. In some embodiments, at least about 70% of the fremanezumab in the liquid pharmaceutical composition is of the IgG2-B disulfide isoform. In these and other embodiments described herein, the liquid pharmaceutical composition can be delivered via a syringe, e.g., a syringe pre-filled with the liquid pharmaceutical composition. In some embodiments, the injection is a sterile, preservative-free, clear to opalescent, colorless to slightly yellow solution (i.e., liquid pharmaceutical composition) for subcutaneous injection, supplied in a single-dose 225 mg/1.5 mL prefilled syringe.

In some embodiments, a pharmaceutical composition described herein may have any suitable viscosity for therapeutic efficacy, delivery, safety and/or storage. For example, the viscosity of a liquid pharmaceutical composition described herein may be from about 0.5 centipoise (cP) to about 100 cP, from about 1 cP to about 50 cP, from about 1 cP to about 20 cP, from about 1 cP to about 15 cP, or from about 5 cP to about 15 cP, at 25° C. In some embodiments, a liquid pharmaceutical composition described herein may have a viscosity of about 0.5 cP, about 1 cP, about 1.2 cP, about 1.4 cP, about 1.6 cP, about 1.8 cP, about 2.0 cP, about 2.2 cP, about 2.4 cP, about 2.6 cP, about 2.8 cP, about 3.0 cP, about 3.2 cP, about 3.4 cP, about 3.6 cP, about 3.8 cP, about 4.0 cP, about 4.2 cP, about 4.4 cP, about 4.6 cP, about 4.8 cP, about 5.0 cP, about 5.2 cP, about 5.4 cP, about 5.6 cP, about 5.8 cP, about 6.0 cP, about 6.2 cP, about 6.4 cP, about 6.6 cP, about 6.8 cP, about 7.0 cP, about 7.2 cP, about 7.4 cP, about 7.6 cP, about 7.8 cP, about 8.0 cP, about 8.2 cP, about 8.4 cP, about 8.6 cP, about 8.8 cP, about 9.0 cP, about 9.2 cP, about 9.4 cP, about 9.6 cP, about 9.8 cP, about 10.0 cP, about 10.2 cP, about 10.4 cP, about 10.6 cP, about 10.8 cP, about 11.0 cP, about 11.2 cP, about 11.4 cP, about 11.6 cP, about 11.8 cP, about 12.0 cP, about 12.2 cP, about 12.4 cP, about 12.6 cP, about 12.8 cP, about 13.0 cP, about 13.2 cP, about 13.4 cP, about 13.6 cP, about 13.8 cP, about 14.0 cP, about 14.2 cP, about 14.4 cP, about 14.6 cP, about 14.8 cP, or about 15.0 cP, at 25° C. In some embodiments, a liquid pharmaceutical composition described herein may have a viscosity of about 0.5 cP, about 1 cP, about 1.2 cP, about 1.4 cP, about 1.6 cP, about 1.8 cP, about 2.0 cP, about 2.2 cP, about 2.4 cP, about 2.6 cP, about 2.8 cP, about 3.0 cP, about 3.2 cP, about 3.4 cP, about 3.6 cP, about 3.8 cP, about 4.0 cP, about 4.2 cP, about 4.4 cP, about 4.6 cP, about 4.8 cP, about 5.0 cP, about 5.2 cP, about 5.4 cP, about 5.6 cP, about 5.8 cP, about 6.0 cP, about 6.2 cP, about 6.4 cP, about 6.6 cP, about 6.8 cP, about 7.0 cP, about 7.2 cP, about 7.4 cP, about 7.6 cP, about 7.8 cP, about 8.0 cP, about 8.2 cP, about 8.4 cP, about 8.6 cP, about 8.8 cP, about 9.0 cP, about 9.2 cP, about 9.4 cP, about 9.6 cP, about 9.8 cP, about 10.0 cP, about 10.2 cP, about 10.4 cP, about 10.6 cP, about 10.8 cP, about 11.0 cP, about 11.2 cP, about 11.4 cP, about 11.6 cP, about 11.8 cP, about 12.0 cP, about 12.2 cP, about 12.4 cP, about 12.6 cP, about 12.8 cP, about 13.0 cP, about 13.2 cP, about 13.4 cP, about 13.6 cP, about 13.8 cP, about 14.0 cP, about 14.2 cP, about 14.4 cP, about 14.6 cP, about 14.8 cP, or about 15.0 cP, at 22° C. In some embodiments, a liquid pharmaceutical composition described herein may have a viscosity of less than about 20.0 cP at 25° C. In some embodiments, the pharmaceutical compositions described herein have a viscosity of about 7.7 cP, at 25° C. In some embodiments, the pharmaceutical compositions described herein have a viscosity of about 8.8 cP, at 22° C.

In some embodiments, a pharmaceutical composition described herein may have any suitable conductivity for therapeutic efficacy, deliver, safety, and/or storage. For example, the conductivity of a liquid pharmaceutical composition described herein may be from about 0.1 millisiemens per centimeter (mS/cm) to about 15 mS/cm, from about 0.1 mS/cm to about 10 mS/cm, from about 0.1 mS/cm to about 5 mS/cm, from about 0.1 mS/cm to about 2 mS/cm, from about 0.1 mS/cm to about 1.5 mS/cm, or from about 1.3 mS/cm to about 1.5 mS/cm. In some embodiments, a liquid pharmaceutical composition described herein has a conductivity of about 0.19 mS/cm, about 0.59 mS/cm, about 1.09 mS/cm, about 1.19 mS/cm, about 1.29 mS/cm, about 1.36 mS/cm, about 1.39 mS/cm, about 1.49 mS/cm, about 1.59 mS/cm, about 1.69 mS/cm, about 1.79 mS/cm, about 1.89 mS/cm, about 1.99 mS/cm, about 2.09 mS/cm, about 2.19 mS/cm, about 2.29 mS/cm, about 2.39 mS/cm, about 2.49 mS/cm, about 2.59 mS/cm, about 2.69 mS/cm, about 2.79 mS/cm, about 2.89 mS/cm, about 2.99 mS/cm, about 3.09 mS/cm, about 3.19 mS/cm, about 3.29 mS/cm, about 3.39 mS/cm, about 3.49 mS/cm, about 3.59 mS/cm, about 3.69 mS/cm, about 3.79 mS/cm, about 3.89 mS/cm, about 3.99 mS/cm, about 4.09 mS/cm, about 4.19 mS/cm, about 4.29 mS/cm, about 4.39 mS/cm, about 4.49 mS/cm, about 4.59 mS/cm, about 4.69 mS/cm, about 4.79 mS/cm, about 4.89 mS/cm, about 4.99 mS/cm, about 5.09 mS/cm, about 6.09 mS/cm, about 6.59 mS/cm, about 7.09 mS/cm, about 7.59 mS/cm, about 8.09 mS/cm, about 8.59 mS/cm, about 9.09 mS/cm, about 9.59 mS/cm, about 10.09 mS/cm, about 10.59 mS/cm, about 11.09 mS/cm, about 11.59 mS/cm, about 12.09 mS/cm, about 12.59 mS/cm, about 13.09 mS/cm, about 13.59 mS/cm, about 14.09 mS/cm, about 14.59 mS/cm, or about 15.09 mS/cm. In some embodiments, a liquid pharmaceutical composition described herein has a conductivity of about 1.36 mS/cm.

In some embodiments, a liquid pharmaceutical composition described herein may have any suitable osmolality for therapeutic efficacy, delivery, safety, and/or storage. For example, the osmolality of a liquid pharmaceutical composition described herein may be from about 50 milliosmole per kilogram (mOsm/kg) to about 1000 mOsm/kg, from about 100 mOsm/kg to about 600 mOsm/kg, from about 400 mOsm/kg to about 600 mOsm/kg, or from about 450 mOsm/kg to about 550 mOsm/kg. In some embodiments, the osmolality of a liquid pharmaceutical composition described herein may be from about 300 mOsm/kg to about 500 mOsm/kg. In some embodiments, the osmolality of a liquid pharmaceutical composition described herein may be from about 300 mOsm/kg to about 450 mOsm/kg. In some embodiments, a liquid pharmaceutical composition described herein may have an osmolality of about 50 mOsm/kg, about 60 mOsm/kg, about 70 mOsm/kg, about 80 mOsm/kg, about 90 mOsm/kg, about 100 mOsm/kg, about 120 mOsm/kg, about 140 mOsm/kg, about 160 mOsm/kg, about 180 mOsm/kg, about 200 mOsm/kg, about 220 mOsm/kg, about 240 mOsm/kg, about 260 mOsm/kg, about 280 mOsm/kg, about 300 mOsm/kg, about 320 mOsm/kg, about 340 mOsm/kg, about 360 mOsm/kg, about 380 mOsm/kg, about 400 mOsm/kg, about 420 mOsm/kg, about 440 mOsm/kg, about 460 mOsm/kg, about 480 mOsm/kg, about 500 mOsm/kg, about 520 mOsm/kg, about 540 mOsm/kg, about 560 mOsm/kg, about 580 mOsm/kg, about 600 mOsm/kg, about 620 mOsm/kg, about 640 mOsm/kg, about 660 mOsm/kg, about 680 mOsm/kg, about 700 mOsm/kg, about 720 mOsm/kg, about 740 mOsm/kg, about 760 mOsm/kg, about 780 mOsm/kg, about 800 mOsm/kg, about 820 mOsm/kg, about 840 mOsm/kg, about 860 mOsm/kg, about 880 mOsm/kg, about 900 mOsm/kg, about 920 mOsm/kg, about 940 mOsm/kg, about 960 mOsm/kg, about 980 mOsm/kg, about 1000 mOsm/kg, about 1050 mOsm/kg, about 1100 mOsm/kg, about 1150 mOsm/kg, about 1200 mOsm/kg, about 1250 mOsm/kg, about 1300 mOsm/kg, about 1350 mOsm/kg, about 1400 mOsm/kg, about 1450 mOsm/kg, or about 1500 mOsm/kg. In some embodiments, a liquid pharmaceutical composition described herein has an osmolality of about 365 mOsm/kg. The osmolality of a pharmaceutical composition may be measured, for example, using a freezing point depression type osmometer.

In some embodiments, the pharmaceutical compositions are stable. Stable pharmaceutical compositions are compositions in which the antibody molecules present in the composition retain their physical stability and/or chemical stability and/or biological activity during the manufacturing process and/or upon storage. Analytical techniques for measuring the protein stability are known the art (see, e.g., Pearlman, R., and Nguyen, T. H., 1991, Analysis of protein drugs, in: Peptide and Protein Drug Delivery (V. H. Lee, ed.), Dekker, New York, pp. 247-301; and Jones (1993) Adv. Drug Delivery Rev. 10: 29-90). An antibody retains physical stability in a pharmaceutical composition if it exhibits substantially no significant increase in aggregation (e.g., the formation of dimers, trimers, tetramers, oligomers or higher order aggregates), precipitation, and/or denaturation, as measured, for example using ultraviolet light scattering, size exclusion chromatography, or changes in turbidity and/or color of the composition. Physical stability of the antibody in the pharmaceutical composition may be assessed, for example, by measuring the apparent attenuation of light (e.g., absorbance and/or optical density) of the composition as an indicator of turbidity or measuring the amount of sub-visible particles in the pharmaceutical composition (e.g., using micro flow imaging (MFI)). Chemical stability can be assessed by, e.g., detecting and quantifying chemically altered forms of the antibody in the composition, including size modification (e.g., clipping) which may be examined using size exclusion chromatography, SDS-PAGE (e.g., non-reducing capillary SDS-PAGE) and/or matrix-assisted laser desorption ionization/time-of-flight mass spectrometry (MALDI/TOF MS). Other chemical stability indicators include changes in the pH, osmolality, oxidized methionine content, and charge alterations (e.g., as a result of deamidation or oxidation, and can be evaluated using ion-exchange chromatography or imaged capillary iso-electric focusing (icIEF)). Biological activity of the antibody in the compositions may be analyzed, for example, by analyzing the antigen-binding activity of the antibody in the pharmaceutical composition as compared to the antigen-binding activity that the antibody molecules exhibited at the time that the pharmaceutical composition was prepared. Assays for determining antigen-binding activity (e.g., CGRP-binding activity) include ELISA and surface plasmon resonance (e.g., as described in U.S. Pat. No. 8,007,794, incorporated herein by reference).

The stability of a pharmaceutical composition may be analyzed after storage at room temperature, at about 25-30° C. (e.g., 25° C.±2° C.), at about 40° C. (e.g., 40° C.±2° C.), or at about 2-8° C., for at least 1 week, at least 2 weeks, at least 1 month, at least 2 months, at least 3 months, at least 6 months, at least 9 months, at least 1 year, at least 18 months, at least 2 years, at least 30 months, or at least 3 years. For example, the stability of a pharmaceutical composition may be analyzed after storage 25° C.±2° C., 60%±5% relative humidity (RH) for at least 1 week, at least 2 weeks, at least 1 month, at least 2 months, at least 3 months, at least 6 months, at least 9 months, at least 1 year, at least 18 months, at least 2 years, at least 30 months, or at least 3 years. For example, the stability of a pharmaceutical composition may be analyzed after storage 40° C.±2° C., 75%±5% RH for at least 1 week, at least 2 weeks, at least 1 month, at least 2 months, at least 3 months, at least 6 months, at least 9 months, at least 1 year, at least 18 months, at least 2 years, at least 30 months, or at least 3 years.

In some embodiments, the pharmaceutical compositions described herein are stable after storage at 2-8° C. for at least 1 week, at least 2 weeks, at least 1 month, at least 3 months, at least 6 months, at least 1 year, at least 18 months, at least 2 years, at least 30 months, or at least 3 years. In some embodiments, the pharmaceutical compositions described herein are stable after storage at 25° C.±2° C., 60%±5% relative humidity (RH) for at least 1 week, at least 2 weeks, at least 1 month, at least 3 months, at least 6 months, at least 1 year, at least 18 months, at least 2 years, at least 30 months, or at least 3 years. In some embodiments, the pharmaceutical compositions described herein are stable after storage at about 40° C.±2° C., 75%±5% RH for at least 1 week, at least 2 weeks, at least 1 month, at least 3 months, at least 6 months, at least 1 year, at least 18 months, at least 2 years, at least 30 months, or at least 3 years. In some embodiments, the antibody molecules in the composition retain at least about 80% of their antigen-binding activity (e.g., as determined by ELISA) after storage, as compared to the antigen-binding activity of the antibody molecules in the composition prior to storage.

In some embodiments, the pharmaceutical compositions described herein are suitable for administration to a subject using any therapeutic dose via a desired route (e.g., subcutaneously or intravenously). The pharmaceutical compositions described herein can also be administered to a subject by subcutaneous, intramuscular, intraperitoneal, intracerebrospinal, intra-articular, sublingually, intra-arterial, intra-synovial, via insufflation, intrathecal, oral, inhalation, intra-nasal (e.g., with or without inhalation), buccal, rectal, transdermal, intracardiac, intraosseous, intradermal, transmucosal, vaginal, intravitreal, peri-articular, local, epicutaneous, or topical routes. Administration can be systemic, e.g., intravenous administration, or localized. In some embodiments, an antibody described herein can be administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568, which are hereby incorporated by reference in their entireties.

The volume of a liquid pharmaceutical composition described herein may vary, for example, in order to provide or deliver an effective dose of anti-CGRP antagonist antibody to a subject. For example, the volume of a liquid pharmaceutical composition may be from about 0.001 mL to about 10.0 mL, from about 0.01 mL to about 5.0 mL, from about 0.1 mL to about 5 mL, from about 0.1 mL to about 3 mL, from about 0.5 mL to about 2.5 mL, or from about 1 mL to about 2.5 mL. For example, the volume of a liquid pharmaceutical composition can be about 0.001 mL, 0.005 mL, 0.01 mL, 0.02 mL, 0.03 mL, 0.04 mL, 0.05 mL, 0.06 mL, 0.07 mL, 0.08 mL, 0.09 mL, 0.10 mL, 0.2 mL, 0.3 mL, 0.4 mL, 0.5 mL, 0.6 mL, 0.7 mL, 0.8 mL, 0.9 mL, 1.0 mL, 1.1 mL, 1.2 mL, 1.3 mL, 1.4 mL, 1.5 mL, 1.6 mL, 1.7 mL, 1.8 mL, 1.9 mL, 2.0 mL, 2.1 mL, 2.2 mL, 2.3 mL, 2.4 mL, 2.5 mL, 2.6 mL, 2.7 mL, 2.8 mL, 2.9 mL, 3.0 mL, 3.1 mL, 3.2 mL, 3.3 mL, 3.4 mL, 3.5 mL, 3.6 mL, 3.7 mL, 3.8 mL, 3.9 mL, 4.0 mL, 4.1 mL, 4.2 mL, 4.3 mL, 4.4 mL, 4.5 mL, 4.6 mL, 4.7 mL, 4.8 mL, 4.9 mL, 5.0 mL, 5.5 mL, 6.0 mL, 6.5 mL, 7.0 mL, 7.5 mL, 8.0 mL, 8.5 mL, 9.0 mL, 9.5 mL, or 10.0 mL. In some embodiments, the volume of a liquid pharmaceutical composition described herein is about 1.5 mL.

B. Anti-CGRP Antagonist Antibodies

The pharmaceutical composition and methods described herein include IgG2 anti-CGRP antagonist antibodies. In some embodiments, the pharmaceutical compositions described herein include the anti-CGRP antagonist antibody G1 (also known as fremanezumab), IgG2 antibodies having six CDRs corresponding to those of the light and heavy chain of antibody G1, or IgG2 antibodies having the heavy chain and light chain variable regions of antibody G1 (or variants thereof). In some embodiments, the anti-CGRP antagonist antibody is an isolated antibody. In some embodiments, the IgG2 anti-CGRP antagonist antibodies include a kappa light chain constant region. In some embodiments, the IgG2 anti-CGRP antagonist antibodies include a lambda light chain constant region.

In some embodiments, the binding affinity ($K_D$) of anti-CGRP antagonist antibody to CGRP can be about 0.06 to about 200 nM. For example, the binding affinity can be any of about 200 nM, 100 nM, about 50 nM, about 10 nM, about 1 nM, about 500 pM, about 100 pM, about 60 pM, about 50 pM, about 20 pM, about 15 pM, about 10 pM, about 5 pM, or about 2 pM. In other examples, the binding affinity is less than any of about 250 nM, about 200 nM, about 100 nM, about 50 nM, about 10 nM, about 1 nM, about 500 pM, about 100 pM, or about 50 pM.

An antibody used in the pharmaceutical compositions and methods described herein, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds.), Molecular Cloning; A Laboratory Manual, Second Edition, Cold Spring Harbor, N.Y., (1989); Ausubel, F. M. et al. (eds.) Current Protocols in Molecular Biology, Greene Publishing Associates, (1989); and in U.S. Pat. No. 4,816,397.

To express an anti-CGRP antagonist antibody, e.g., antibody G1, polynucleotides encoding the light and heavy chain variable regions of the protein are obtained. For instance, exemplary polynucleotides encoding the G1 heavy and light chain variable regions are shown in SEQ ID NO: 5 and SEQ ID NO: 6, respectively, and exemplary polynucleotides encoding the G1 full length heavy chain and light chains are shown in SEQ ID NO: 3 and SEQ ID NO: 4, respectively. For example, polynucleotides encoding heavy chain and light chain variable regions can be further manipulated by standard recombinant DNA techniques, for example to convert the variable region genes to full-length antibody chain genes. In these manipulations, a VL- or VH-encoding DNA fragment is operatively linked to another DNA fragment encoding e.g., an antibody constant region. The term "operatively linked," as used in this context, is intended to mean that the two DNA fragments are joined such that the amino acid sequences encoded by the two DNA fragments remain in-frame. The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region is preferably an IgG2 constant region. The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. In one embodiment, the light chain constant region is a kappa constant region.

To express the antibodies DNAs encoding full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The recombinant expression vector can encode a signal peptide that facilitates secretion of the antibody chain from a host cell. The signal peptide can be an immunoglobulin signal peptide or a heterologous signal peptide.

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Exemplary regulatory sequences for mammalian host cell expression include viral elements that direct high levels of protein expression in mammalian cells, such as promoters and/or enhancers derived from cytomegalovirus (CMV) Simian Virus 40 (SV40), adenovirus, (e.g., the adenovirus major late promoter (AdMLP)) and polyoma.

In addition to the antibody chain genes and regulatory sequences, the recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634, 665 and 5,179,017), including, for example, selectable marker genes that confer resistance to drugs, such as G418, hygromycin or methotrexate, on a host cell into which the vector has been introduced, or the selectable marker gene dihydrofolate reductase (DHFR) (for use in dhfr-host cells with methotrexate selection/amplification) and the neo gene (for G418 selection). For expression of the light and heavy chains, the expression vector(s) encoding the heavy and light chains is transfected into a host cell by standard techniques.

Exemplary host cells for expressing the recombinant antibodies of the invention include Chinese hamster ovary (CHO cells) (including dhfr-CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more, in one embodiment, secretion of the antibody into the culture medium in which the host cells are grown. Antibodies can be recovered from the culture medium using standard protein purification methods.

Methods of Separating IgG2 Disulfide Isoforms

Heterogeneous preparations having distinct IgG2 disulfide isoforms can be separated using methods known in the art. For example, IgG2 disulfide isoforms may be enriched using redox treatment as described, for example, in U.S. Pat. No. 7,928,205, Dillon et al. (2008) *J. Biol. Chem.* 283(23): 16206-215, Dillon et al. (2006) *J. Chromatogr. A* 1120: 112-20, each of which are incorporated herein by reference. Alternatively, weak cation exchange chromatography can be used to separate IgG2 isoforms, as described, for example, in Wypych et al. (2008) *J. Biol. Chem.* 283(23): 16194-205, incorporated herein by reference.

Combinatorial chromatography methods can be used to isolate and/or enrich for desired IgG2 disulfide isoforms, as described, for example in U.S. Publication No. 2014/0371427, incorporated herein by reference. For instance, a combination of one or more of strong cation exchange chromatography, protein L affinity chromatography, and IgG2 affinity matrix chromatography can be used to enrich for distinct IgG2 disulfide isoforms. Each of these chromatography methods are briefly described below.

Strong Cation Exchange Chromatography (SCX)

Cation exchange chromatography resolves small differences in the overall surface charge of proteins. Since each IgG2 disulfide isoform exhibits a unique surface charge, strong cation exchange chromatography can be used to resolve the different IgG2 disulfide isoforms. Exemplary SCX media include SP-Sepharose® FF, SP-Sepharose® BB, SP-Sepharose® XL, SP-Sepharose® HP, Mini S, Mono S, Source 15S, Source 30S, Capto S, MacroCap SP, Streamline SP-XL, Streamline CST-1 (all by GE Healthcare Life Sciences, Marlborough, Mass., USA; Toyopearl® Mega Cap TI SP-550 EC, Toyopearl® Giga Cap S-650M, Toyopearl® 650S, Toyopearl® SP650S, Toyopearl® SP550C (all by Tosoh Bioscience GmbH, Greisheim, Germany); Carboxy-Sulphon-5, 15 and 40 um, Sulfonic-5, 15, and 40 um (J.T.Baker™ Resins); and Poros™ HS 20 and 50 um, Poros™ S 10 and 20 um (ThermoFisher Scientific, Waltham, Mass. USA). Methods of performing cation exchange chromatography are described in U.S. Publication No. 2014/0371427; Protein Purification Methods, A Practical Approach, Ed. Harris ELV, Angal S, IRL Press Oxford, England (1989); Protein Purification, Ed. Janson J C, Ryden L, VCH-Verlag, Weinheim, Germany (1989); Process Scale Bioseparations for the Biopharmaceutical Industry, Ed. Shukla A. A., Etzel M. R., Gadam S, CRC Press Taylor & Francis Group (2007), pages 188-196; Protein Purification Handbook, GE Healthcare 2007 (18-1132-29); and Protein Purification, Principles, High Resolution Methods and Applications (2.sup.nd Edition 1998), Ed. Janson J-C and Ryden L; the disclosures of which are incorporated herein by reference.

Protein L Chromatography

Protein L is a bacterial cell wall protein that binds IgG with high specificity. Protein L exhibits higher affinity for IgG2-A disulfide isoforms than for IgG2-B or IgG2-A/B isoforms. Protein L affinity resins are commercially available (see, e.g., Pierce Protein L affinity resin; Thermo Scientific Pierce, Rockford, Ill., U.S.A.). Methods of separating IgG2 disulfide isoforms using Protein L chromatography are described in U.S. Publication No. 2014/0371427, incorporated herein by reference.

IgG2 Affinity Matrix Chromatography

The antibody HP-6014 strongly binds to IgG2-A disulfide isoforms. Thus, affinity chromatography columns coupled with HP-6014 can be used to separate IgG2-A from heterogeneous preparations, as described in U.S. Publication No. 2014/0371427 (HP-6014 is described in Harada et al. (1991) *J. Immunol. Methods* 141: 89-96; and Harada et al. (1992) *Mol. Immunol.* 29: 145-149).

Oxidative Refolding Using Reduction/Oxidation Coupling Reagents and/or Chaotropic Agents Preparations including heterogeneous mixtures of IgG2 disulfide isoforms can be subjected to oxidative refolded in the presence of a reduction/oxidation reagent (and optionally a chaotropic agent) in order to refold the proteins in the preparation to enrich for a desired disulfide isoform, as described in U.S. Publication No. 2006/0194280, incorporated herein by reference.

For example, preparations (e.g., culture media) may be contacted with a reduction/oxidation coupling reagent for a time sufficient to increase the relative proportion of the desired disulfide isoform. The contacting step may be performed while the preparation having the IgG2 antibody molecules is present (e.g., attached to) a solid support or are present in a culture media containing cells expressing the IgG2 antibody molecules. The contacting step is preferably performed while the IgG2 antibody molecules are present in a buffered solution so as to optimize disulfide exchange (e.g., from about pH 5 to about pH 10 (e.g., pH 6, pH 7, pH 8, or pH 9)).

Exemplary reduction/oxidation coupling reagents include reduced and oxidized glutathione, dithiothreitol (DTT), 2-mercaptoethanol, dithionitrobenzoate, cysteine and cystine/cystamine. The concentration of reduction/oxidation coupling reagent to induce protein folding will depend on the concentration of IgG2 antibody molecules present in a preparation and on the number and accessibility of unpaired cysteines in the IgG2 antibody molecules. Exemplary concentrations of reduction/oxidation reagents are from about 0.05 mM to about 50 mM, from about 0.1 mM to about 25 mM, or from about 0.2 mM to about 20 mM. Reduction/oxidation coupling reagents can contain oxidized thiols and reduced thiols. The ratio of reduced thiols to oxidized thiols can be from about 1:10 to about 1000:1, from about 1:1 to about 500:1, from about 5:1 to about 100:1, or about 10:1. Preparations can be contacted with the reduction/oxidation coupling reagent for about 1 hour, 4 hours, 8 hours, 12 hours, 16 hours, about 18 hours, or more, at a wide range of temperatures (e.g., from about 4° C. to about 37° C.). Disulfide exchange can be quenched, for example by diluting the reduction/oxidation coupling reagent, removing it from the IgG2 antibody molecules (e.g., using a purification step), or by chemical inactivation (e.g., by acidification/alkylation). Following refolding, the preparation can be subjected to one or more purification steps.

Optionally, the preparation including the IgG2 antibody molecules can be contacted with a chaotropic reagent to perturb the tertiary and/or quaternary structure of the IgG2 antibody molecules. Preferably, the amount of chaotropic reagent is titred such that complete unfolding of the protein does not occur when contacted with the chaotropic agent (e.g., equilibrium denaturation can be performed to determine the conditions at which the IgG2 antibody molecules start to unfold). Exemplary chaotropic reagents include, for example, sodium dodecyl sulfate (SDS), urea, and guanidium hydrochloride (GuHCl).

C. Articles of Manufacture

In another aspect, the disclosure provides articles of manufacture that contain a pharmaceutical composition described herein. In some embodiments, the articles of manufacture include containers and medical devices. The containers and medical devices may be formed from a variety of materials including glass, metal and/or plastic. Suitable containers, include, for example, vials (e.g., dual chamber vials or single chamber vials), cartridges, syringes (e.g., pre-filled syringes) and autoinjectors, such as injector pens and needleless devices. In some embodiments, the article of manufacture is a pre-filled syringe. In some embodiments, the article of manufacture is an autoinjector (e.g., a pre-filled autoinjector such as an injector pen or a needleless device).

In some embodiments, the article of manufacture is a pre-filled syringe (e.g., a pre-filled glass or plastic syringe) including a liquid pharmaceutical composition that comprises from about 135 mg/mL to about 165 mg/mL of fremanezumab, from about 5 to about 30 mM histidine, from about 55 mg/mL to about 75 mg/mL sucrose, from about 0.02 mg/mL to about 0.2 mg/mL EDTA disodium dihydrate, from about 0.05 to about 0.5 mg/ml polysorbate 80, at a pH of about 5.5±0.3, wherein at least about 70% of the fremanezumab in the composition is of the IgG2-B disulfide isoform. In some embodiments, the article of manufacture is a pre-filled syringe (e.g., a pre-filled glass or plastic syringe) including a liquid pharmaceutical composition that comprises from about 135 mg/mL to about 165 mg/mL of fremanezumab, from about 10 to about 20 mM histidine, from about 60 mg/mL to about 70 mg/mL sucrose, from about 0.1 mg/mL to about 0.2 mg/mL EDTA disodium dihydrate, from about 0.1 to about 0.3 mg/ml polysorbate 80, at a pH of about 5.5±0.3, wherein at least about 70% of the fremanezumab in the composition is of the IgG2-B disulfide isoform. In some embodiments, the article of manufacture is a pre-filled syringe (e.g., a pre-filled glass or plastic syringe) including a liquid pharmaceutical composition that comprises about 150 mg/mL (±15 mg/mL) of fremanezumab, about 16 mM histidine, about 66 mg/mL sucrose, about 0.136 mg/mL EDTA disodium dihydrate, and about 0.2 mg/mL polysorbate 80, at a pH of about 5.5±0.3, wherein at least about 70% of the fremanezumab in the composition is of the IgG2-B disulfide isoform. In some embodiments, the article of manufacture is a pre-filled syringe including a liquid pharmaceutical composition that comprises about 150 mg/mL of fremanezumab, about 0.54 mg/mL L-histidine, about 2.62 mg/mL L-histidine hydrochloride monohydrate, about 66 mg/mL sucrose, about 0.14 mg/mL EDTA disodium dihydrate, and about 0.2 mg/mL polysorbate 80, at a pH of about 5.5±0.3, wherein at least about 70% of the fremanezumab in the composition is of the IgG2-B disulfide isoform.

In some embodiments, the article of manufacture is a pre-filled autoinjector including a liquid pharmaceutical composition that comprises from about 135 mg/mL to about 165 mg/mL of fremanezumab, from about 5 to about 30 mM histidine, from about 55 mg/mL to about 75 mg/mL sucrose, from about 0.02 mg/mL to about 0.2 mg/mL EDTA disodium dihydrate, from about 0.05 to about 0.5 mg/ml polysorbate 80, at a pH of about 5.5±0.3, wherein at least about 70% of the fremanezumab in the composition is of the IgG2-B disulfide isoform. In some embodiments, the article of manufacture is a pre-filled autoinjector including a liquid pharmaceutical composition that comprises from about 135 mg/mL to about 165 mg/mL of fremanezumab, from about 10 to about 20 mM histidine, from about 60 mg/mL to about 70 mg/mL sucrose, from about 0.1 mg/mL to about 0.2 mg/mL EDTA disodium dihydrate, from about 0.1 to about 0.3 mg/ml polysorbate 80, at a pH of about 5.5±0.3, wherein at least about 70% of the fremanezumab in the composition is of the IgG2-B disulfide isoform. In some embodiments, the article of manufacture is a pre-filled autoinjector including a liquid pharmaceutical composition that comprises about 150 mg/mL (±15 mg/mL) of fremanezumab, about 16 mM histidine, about 66 mg/mL sucrose, about 0.136 mg/mL EDTA disodium dihydrate, and about 0.2 mg/mL polysorbate 80, at a pH of about 5.5±0.3, wherein at least about 70% of the fremanezumab in the composition is of the IgG2-B disulfide isoform. In some embodiments, the article of manufacture is a pre-filled autoinjector including a liquid pharmaceutical composition that comprises about 150 mg/mL of fremanezumab, about 0.54 mg/mL L-histidine, about 2.62 mg/mL L-histidine hydrochloride monohydrate, about 66 mg/mL sucrose, about 0.14 mg/mL EDTA disodium dihydrate, and about 0.2 mg/mL polysorbate 80, at a pH of about 5.5±0.3, wherein at least about 70% of the fremanezumab in the composition is of the IgG2-B disulfide isoform.

In some embodiments, the article of manufacture includes less than about 2.0 mL (e.g., 1.9 mL, 1.8 mL, 1.7 mL, 1.6 mL, 1.5 mL, 1.4 mL, 1.3 mL, 1.2 mL, 1.1 mL, 1.0 mL, 0.9 mL, 0.8 mL, 0.7 mL, 0.6 mL, 0.5 mL, 0.4 mL, 0.3 mL, 0.2 mL, or 0.1 mL) of a liquid pharmaceutical composition described herein. In some embodiments, the article of manufacture (e.g., a glass or plastic syringe) includes about 1.5 mL of a liquid pharmaceutical composition described herein. For example, in some embodiments, the article of manufacture (e.g., a glass or plastic syringe or autoinjector) includes about 1.5 mL of a liquid pharmaceutical composition comprising about 150 mg/mL of fremanezumab, about 0.54 mg/mL L-histidine, about 2.62 mg/mL L-histidine hydrochloride monohydrate, about 66 mg/mL sucrose, about 0.14 mg/mL EDTA disodium dihydrate, and about 0.2 mg/mL polysorbate 80, at a pH of about 5.5±0.3, wherein at least about 70% of the fremanezumab in the composition is of the IgG2-B disulfide isoform. In these embodiments, the article of manufacturer includes about 1.5 mL of a liquid pharmaceutical composition comprising about 225 mg of fremanezumab, about 0.82 mg of L-histidine, about 3.93 mg of L-histidine hydrochloride monohydrate, about 99 mg of sucrose, about 0.20 mg of EDTA disodium dehydrate, about 0.3 mg of polysorbate 80, at a pH of about 5.5±0.3, wherein at least about 70% of the fremanezumab in the composition is of the IgG2-B disulfide isoform.

In some embodiments, the article of manufacture is a pre-filled syringe comprising about 1.5 mL of a liquid pharmaceutical composition. Each prefilled syringe can deliver 1.5 mL of solution containing 225 mg fremanezumab, 0.204 mg disodium ethylenediaminetetraacetic acid dihydrate (EDTA), 0.815 mg L-histidine, 3.93 mg L-histidine hydrochloride monohydrate, 0.3 mg polysorbate-80, 99 mg sucrose, and water for injection, at a pH of 5.5. In some embodiments, at least about 70% of the fremanezumab in the liquid pharmaceutical composition is of the IgG2-B disulfide isoform. In some embodiments, the pre-filled syringe comprises a sterile, preservative-free, clear to opalescent, colorless to slightly yellow solution (i.e., liquid pharmaceutical composition) for subcutaneous injection, supplied in a single-dose 225 mg/1.5 mL (i.e., 225 mg/1.5 mL of fremanezumab).

Kits including the articles of manufacture and instructions for their use are also provided.

D. Methods of Treatment

The pharmaceutical compositions described herein can be used for the treatment and/or prevention of any disease or disorder associated with CGRP activity or CGRP upregulation. Diseases associated with CGRP activity or upregulation are described in the literature (See, e.g., Schou et al. The Journal of Headache and Pain (2017) 18:34; DOI 10.1186/s10194-017-0741-2).

In some embodiments, the disease or disorder associated with CGRP is headache.

In further embodiments, the headache is migraine headache or cluster headache.

In some embodiments, the migraine headache is chronic migraine headache or episodic migraine headache.

In some embodiments, the cluster headache is chronic cluster headache or episodic cluster headache.

In some embodiments, the headache is post-traumatic headache.

In some embodiments, the headache is post-ictal headache.

In some embodiments, the headache is medication overuse headache.

In other embodiments, the disease or disorder associated with CGRP is pain.

In some embodiments, the pain is chronic pain.

In some embodiments, the chronic pain is associated with or results from fibromyalgia.

In some embodiments, the pain is visceral pain.

In further embodiments, the visceral pain is associated with or results from interstitial cystitis. In other embodiments, the visceral pain is associated with or results from bladder pain syndrome.

Administration and Dosing

In some embodiments of the methods described herein, a therapeutically effective amount of a pharmaceutical composition provided herein is administered to a subject. In some embodiments of the methods described herein, a subject administers the pharmaceutical composition to himself/herself (self-administration).

In some embodiments of the methods provided herein, the pharmaceutical composition is administered or self-administered to a subject to provide or deliver a dose of the anti-CGRP antagonist antibody (e.g., fremanezumab) in an amount ranging from 0.1 µg to 3000 mg, 1 mg to 1000 mg, 100 to 1000 mg, 100 to 500 mg, 0.1 mg to 5000 mg, 1 mg to 4000 mg, 250 mg to 1000 mg, 500 mg to 1000 mg, 100 mg to 900 mg, 400 mg to 900 mg, 10 mg to 3000 mg, 10 mg to 2000 mg, 100 mg to 2000 mg, 150 mg to 2000 mg, 200 mg to 2000 mg, 250 mg to 2000 mg, 300 mg to 2000 mg, 350 mg to 2000 mg, 400 mg to 2000 mg, 450 mg to 2000 mg, 500 mg to 2000 mg, 550 mg to 2000 mg, 600 mg to 2000 mg, 650 mg to 2000 mg, 700 mg to 2000 mg, 750 mg to 2000 mg, 800 mg to 2000 mg, 850 mg to 2000 mg, 900 mg to 2000 mg, 950 mg to 2000 mg, or 1000 mg to 2000 mg. In some embodiments, the dose or amount of the antibody administered to a subject may be about 0.1 µg, about 1 µg, about 100 µg, about 1 mg, about 10 mg, about 25 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, or about 3000 mg. In some embodiments, the amount of the anti-CGRP antagonist antibody is between 100 to 2000 mg.

In some embodiments of the methods provided herein, the pharmaceutical composition is administered or self-administered in an amount to deliver or provide a dose of about 100 mg to about 1000 mg of the anti-CGRP antagonist antibody.

In some embodiments of the methods provided herein, the pharmaceutical composition is administered or self-administered in an amount to deliver a dose of about 225 mg of the anti-CGRP antagonist antibody.

In some embodiments of the methods provided herein, the pharmaceutical composition is administered or self-administered in an amount to deliver a dose of about 225 mg of the anti-CGRP antagonist antibody at monthly or quarterly intervals.

In some embodiments of the methods provided herein, the pharmaceutical composition is administered or self-administered in an amount to deliver a dose of about 675 mg of the anti-CGRP antagonist antibody.

In some embodiments of the methods provided herein, the pharmaceutical composition is administered or self-administered in an amount to deliver a dose of about 675 mg of the antagonist antibody at monthly or quarterly intervals.

In some embodiments of the methods provided herein, the pharmaceutical composition is administered or self-administered to a subject to deliver an initial dose (e.g., a loading dose) of the anti-CGRP antagonist antibody, followed by administration of the pharmaceutical composition to deliver additional doses at desired intervals. In some embodiments, the initial dose and one or more of the additional doses of the anti-CGRP antagonist antibody are the same. In some embodiments, the one or more additional doses are a different dose than the initial dose. In some embodiments, the frequency at which the one or more additional doses are administered or self-administered is constant (e.g., every month). In some embodiments, the frequency at which the one or more additional doses are administered or self-administered is variable (e.g., one additional dose administered or self-administered at one month following the initial dose, followed by another additional dose at three months following the initial dose). Any desirable and/or therapeutic regimen of initial loading dose, additional doses, and frequency (e.g., including those described herein) of additional doses may be used. An exemplary regimen includes an initial loading dose of 675 mg of anti-CGRP antagonist antibody, followed by subsequent maintenance doses of 225 mg of the anti-CGRP antagonist antibody administered or self-administered at one month intervals.

In some embodiments of the methods provided herein, the pharmaceutical composition is administered or self-administered to deliver an initial dose of the anti-CGRP antagonist antibody and is followed by administration or self-administration of the pharmaceutical composition to provide or deliver a subsequent dose of about 225 mg of the antibody once per month in each of the months subsequent to the month in which the initial dose is administered or self-administered to the subject (e.g., an initial dose of the antagonist antibody of 675 mg or 900 mg, following by subsequent doses of 225 mg of the antagonist antibody monthly).

In some embodiments of the methods provided herein, the pharmaceutical composition including the anti-CGRP antagonist antibody is administered or self-administered intravenously or subcutaneously.

In some embodiments of the methods provided herein, the pharmaceutical composition includes the anti-CGRP antagonist antibody at a concentration of at least about 150 mg/mL (±15 mg/mL).

In some embodiments of the methods provided herein, the pharmaceutical composition comprising the anti-CGRP antagonist antibody is administered or self-administered in a volume of less than about 2 mL.

In some embodiments of the methods provided herein, the pharmaceutical composition comprising the anti-CGRP antagonist antibody is administered or self-administered in a volume of about 1.5 mL.

Combination Therapy

The methods provided herein may further include administering or self-administering to a subject a pharmaceutical composition comprising an anti-CGRP antagonist antibody as disclosed herein alone or in association (e.g., combination) with another active agent, i.e., a second agent.

In some embodiments, the second agent is selected from the group consisting of: 5-HT1 agonists, triptans, opiates, β-adrenergic antagonist, ergot alkaloids, and non-steroidal anti-inflammatory drugs.

In some embodiments, the second agent is administered simultaneously or sequentially with the pharmaceutical composition comprising the anti-CGRP antagonist antibody.

The following Examples are provided to illustrate but not limit the invention. It is understood that the examples and embodiments described herein are for illustrative purposes only and that various modifications or changes in light thereof will be suggested to persons skilled in the art and are to be included within the spirit and purview of this application. All publications, patents, and patent applications cited herein are hereby incorporated by reference in their entirety for all purposes to the same extent as if each individual publication, patent or patent application were specifically and individually indicated to be so incorporated by reference.

EXAMPLES

Example 1: Disulfide Isoform Profile Characterization of a Pharmaceutical Composition Including Fremanezumab The following example describes the analysis and characterization of IgG2-B, IgG2-A/B, and IgG2-A disulfide isoforms of fremanezumab present in an exemplary pharmaceutical composition.

To determine the disulfide isoform profile of the pharmaceutical composition, a FabRICATOR® reverse-phase high-performance liquid chromatography (RP-HPLC) method was performed. Briefly, fremanezumab was digested with FabRICATOR®, which cleaves the antibody below the hinge region. The digestion product, including F(ab')$_2$ and Fc, were separated by RP-HPLC. The relative abundancy of the disulfide isoforms of F(ab')$_2$ were quantified by relative peak area percent of the first three peaks. Details regarding the procedure are provided below.

Sample Preparation: The fremanezumab reference standard/samples were diluted to 2 mg/mL using digestion buffer (50 mM sodium phosphate, 150 mM sodium chloride, pH 6.6) in 1.5 ml micro centrifuge tube. 50 µL of 2 mg/mL diluted reference standard/sample was transferred to a new 1.5 ml micro centrifuge tube and 7.5 µL of FabRICATOR® (Genovis, Prouct No. A0-FR1-050) was added. An enzyme blank was prepared by mixing 50 µL of digestion buffer with 7.5 µL of FabRICATOR® as enzyme blank. The samples were mixed by vortex and then incubated at 37° C. for 3 hours. The samples were allowed to cool at room temperature for 2-3 minutes. The vials were centrifuged at 10,000 rpm for 3 minutes and the entire content from the 1.5 ml tube was transferred to a HPLC vial.

An Agilent 1200 System with DAD detector or Waters Acquit UPLC system and Zorbax RRHD 300SB-C3 (Agilent Part No. 858750-909 (2.1×100 mm, 1.8 micron)) were used.

HPLC Gradient Conditions:

| Minutes | Flow rate (mL/min) | % Mobile phase A (0.1 % TFA in water) | % Mobile phase B (70% 2-propanol, 20% acetonitrile, 9.9% HPLC water, and 0.1% TFA) |
|---|---|---|---|
| 5 | 0.4 | 70 | 30 |
| 44 | 0.4 | 57 | 43 |
| 50 | 0.4 | 5 | 95 |
| 56 | 0.4 | 70 | 30 |
| 70 | 0.4 | 70 | 30 |

(Injection volume: 12 µL; Column Temperature: 80° C.; Run Time: 70 minutes; Sample compartment temperature: 4° C.; Detection wavelength: 214 nm)

This analysis revealed that the pharmaceutical compositions included 72.0% IgG2-B disulfide isoform, 22.4% IgG2-A/B disulfide isoform, and 5.6% IgG2-A disulfide isoform.

Figure 2:
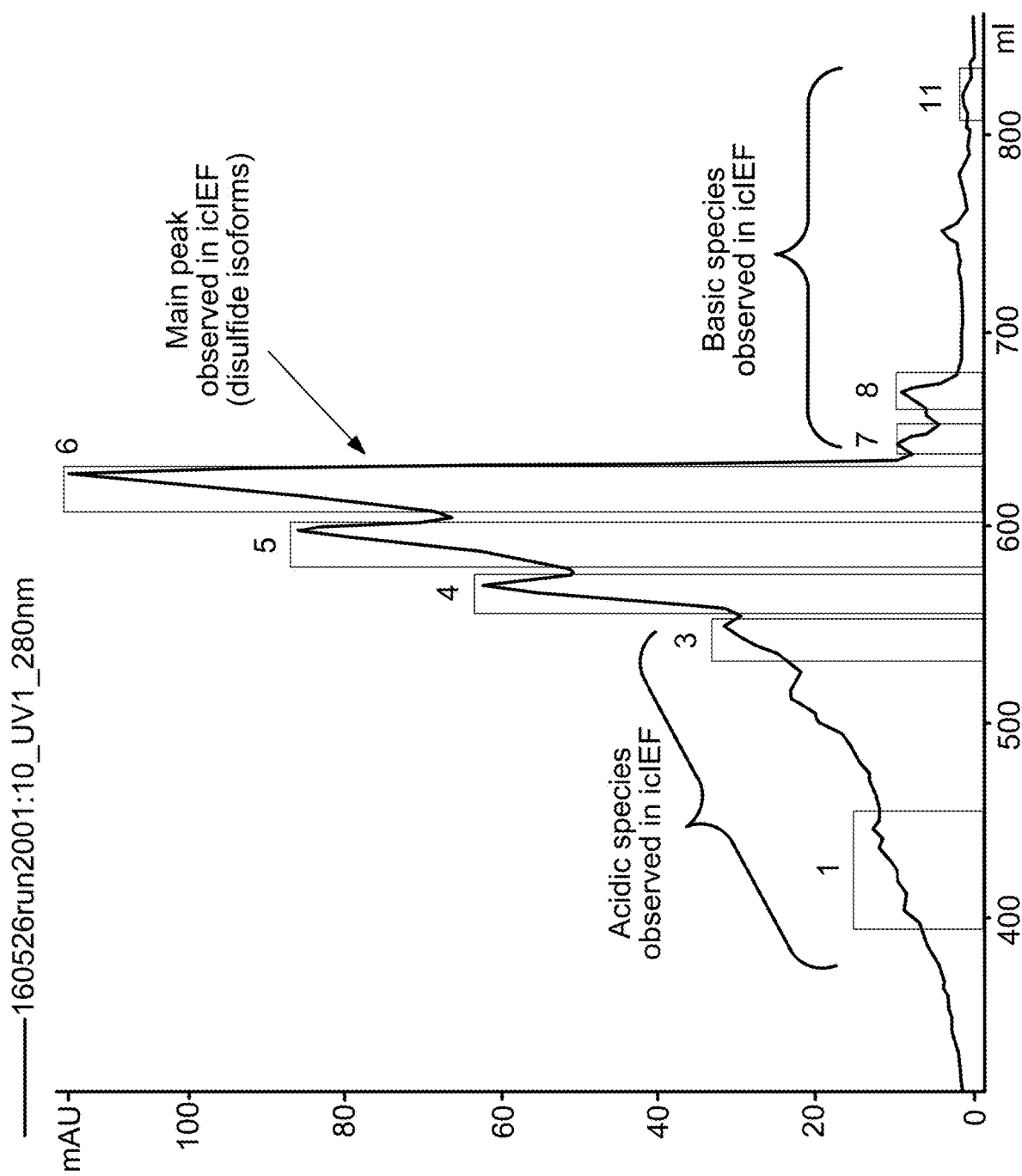
FIG. 2 is a graph depicting a preparative weak cation exchange (WCX) chromatography fractionation analysis of the charge variants and disulfide isoforms of fremanezumab present in an exemplary pharmaceutical composition. Fractions 1 and 3 correspond to acidic charge isoforms of fremanezumab; Fraction 4 corresponds to the IgG2-A disulfide isoform of fremanezumab; Fraction 5 corresponds to the IgG2-A/B disulfide isoform of fremanezumab; Fraction 6 corresponds to the IgG2-B disulfide isoform of fremanezumab; Fractions 7, 8, and 11 correspond to basic charge isoforms of fremanezumab.

Each of the fremanezumab disulfide isoforms were further characterized after fractionation using Ion Exchange Chromatography (IEC), or more specifically preparative weak cation exchange (WCX) chromatography. Briefly, fractionation of fremanezumab was performed by using ProPac WCX-10 Prep (22×250 mm) ion-exchange column and AKTA explorer chromatography system at room temperature. A stock buffer solution containing 40 mM of piperazine, 40 mM imidazole, and 40 mM Tris was first prepared without adjusting the pH value and stored at room temperature. Prior to chromatographic experiments, the mobile phase buffers containing equimolar concentration of piperazine, imidazole and Tris at 4 mM were made by diluting the buffer stock solution with deionized water. The pH value of the Mobile Phase A was then adjusted using hydrochloric acid to 5.0. The pH value of Mobile Phase B was 10.8. The gradient was from 55% B to 90% B per 12.7 column volumes. The mobile phase flow rate was 10 mL/min. Fremanezumab was diluted to 15 or 45 mg/mL with water and 1 mL of the prepared sample was injected. Fractions of 5 mL were collected and fremanezumab variants were concentrated by using Amicon Ultra 30K centrifugal filter devices. Protein concentration in the prepared fractions was determined by absorbance at 280 nm. The WCX column resolved both charge isoforms (i.e., acidic and basic isoforms) and disulfide isoforms of fremanezumab. The partially resolved charge and disulfide isoforms of fremanezumab were fractionated for further characterization. As shown in FIG. 2, acidic isoforms of fremanezumab eluted in fractions 1 and 3, basic isoforms of fremanezumab eluted in fractions 7, 8, and 11, and IgG2-A, IgG2-AB, and IgG2-B disulfide isoform eluted in fractions 4, 5, and 6, respectively.

Figure 3:
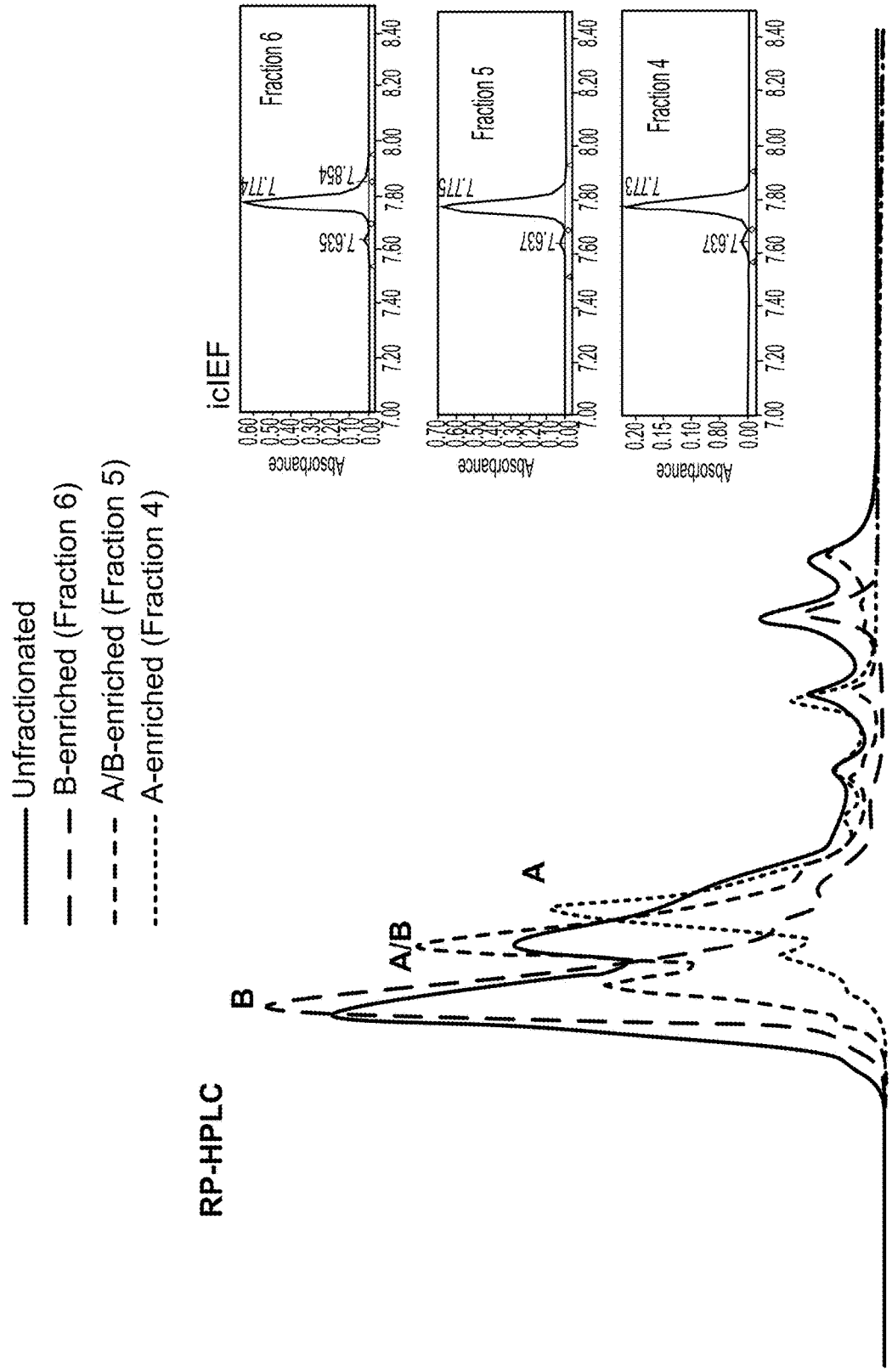
FIG. 3 is a graph depicting a reverse-phase high-performance liquid chromatography (RP-HPLC) analysis of an unfractionated pharmaceutical composition including fremanezumab, and of disulfide isoform-enriched fractions. Unfractionated composition, IgG2-A disulfide isoform-enriched fraction (Fraction 4), IgG2-A/B disulfide isoform-enriched fraction (Fraction 5), and IgG2-B disulfide isoform-enriched fraction (Fraction 6) are depicted. Inset graphs depict an imaged capillary isoelectric focusing (icIEF) analysis of IgG2-A disulfide isoform-enriched fraction (Fraction 4); IgG2-A/B disulfide isoform-enriched fraction (Fraction 5); and IgG2-B disulfide isoform-enriched fraction (Fraction 6).

IgG2-A, IgG2-AB, and IgG2-B disulfide isoform fractions were re-run on reverse-phase high-performance liquid chromatography. Briefly, isolated IEC fractions were injected into Agilent AdvancedBio RP-mAb Diphenyl column (P.N. 793775-944) that was kept at 80° C. The separation was achieved by a shallow gradient (36%-40%) of mobile phase B (0.1% TFA/Acetonitrile) in 27 minutes. Mobile phase A was 0.1% TFA/Water. RP-HPLC chromatograms were analyzed with Empower software 2. As shown in FIG. 3, the content of each disulfide isoform of fremanezumab were further increased in fraction 4, 5 and 6, respectively (81.3% for the IgG2-A disulfide isoform fraction, 88.0% for the IgG2-B disulfide isoform fraction, and 66.0% for the IgG2-A/B disulfide isoform fraction). Disulfide isoform identity was further confirmed by liquid chromatography-mass spectrometry (LC-MS) to detect diagnostic peptides as each isoform has a specific tryptic peptide characteristic of a particular isoform.

To characterize the isoelectric point (pI) of each of the fremanezumab disulfide isoforms, imaged capillary isoelectric focusing (icIEF) analysis was performed. Briefly, the charge profile of fremanuzumab IEC fractions was determined according to the paramaters listed below:

iCE280 Parameters
Focus Period 1, Time (min)●01.00
Focus Period 1, Volt (V): 1500
Focus Period 2, Time (min): 6.00
Focus Period 2, Volt (V): 3000
AutoSampler Parameters
Temperature Control: Yes, 8
Buffer Injection Duration (sec): 225
Buffer Injection Pressure (mbar): 2000
Sample Injection Duration (sec): 150
Sample Injection Pressure (mbar): 2000
Sample Conditions
Carrier Ampholytes: 4% Pharmalyte pH 3-10
Additives: 2 M Urea
Low pI Marker: 6.14
High pI Marker: 9.22

Data from icIEF was analyzed with Empower software 3. As shown in the inset of FIG. 3, the icIEF analysis demonstrated that each of the three disulfide isoforms had the same isoelectric point (pI) which was expected since differences in disulfide bonding should not result in significant charge variation.

Figures 4A, 4B:
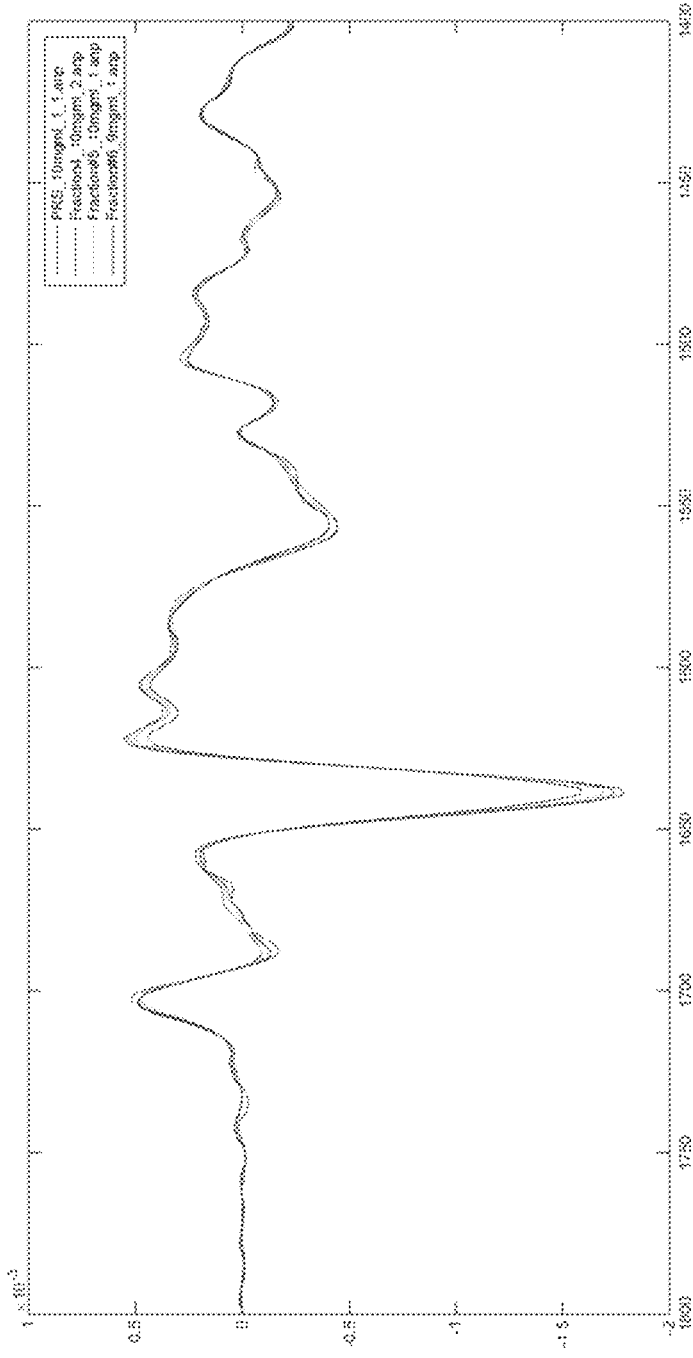
FIG. 4A is a graph depicting the Fourier-transform infrared (FTIR) spectroscopy analysis of a primary reference standard (PRS) and of disulfide-isoform enriched fractions from a pharmaceutical composition including fremanezumab. The spectral profile for IgG2-A disulfide isoform-enriched fraction (Fraction 4), the IgG2-A/B disulfide isoform-enriched fraction (Fraction 5), and the IgG2-B disulfide isoform-enriched fraction (Fraction 6) are depicted.
FIG. 4B is a table showing the secondary structure distribution for IgG2-A ("Fraction #4"), IgG2-A/B ("Fraction #5") and IgG2-B ("Fraction #6") disulfide isoform-enriched fractions isolated from a pharmaceutical composition including fremanezumab.

The secondary and tertiary (i.e., higher order) structure of each of the fremanezumab disulfide isoforms was analyzed using Fourier-transform infrared (FTIR) spectroscopy analysis. As shown in FIGS. 4A and 4B each of the disulfide isoforms had similar spectral profiles and secondary structure distribution.

Figure 5B:
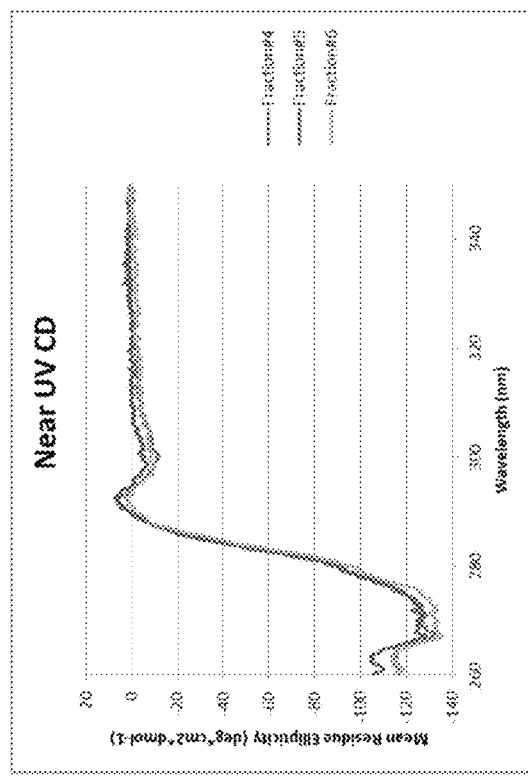
FIG. 5B is a graph depicting the near ultraviolet circular dichroism spectral profiles of IgG2-A ("Fraction #4"), IgG2-A/B ("Fraction #5") and IgG2-B ("Fraction #6") disulfide isoform-enriched fractions isolated from a pharmaceutical composition including fremanezumab.
Figure 5A:
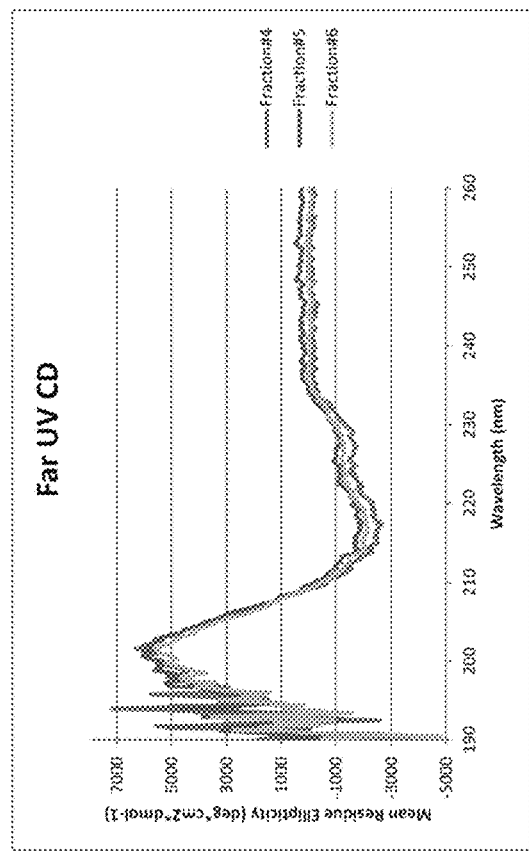
FIG. 5A is a graph depicting the far ultraviolet circular dichroism spectral profiles of IgG2-A ("Fraction #4"), IgG2-A/B ("Fraction #5") and IgG2-B ("Fraction #6") disulfide isoform-enriched fractions isolated from a pharmaceutical composition including fremanezumab.

To further evaluate the secondary and tertiary structure of the fremanezumab disulfide isoforms, circular dichroism (CD) analysis was performed. As shown in FIGS. 5A and 5B, each of the fremanezumab disulfide isoforms exhibited similar spectral profiles and wavelength transitions, even in the disulfide bond region (approximately 300 nm-320 nm) of the near ultraviolet CD spectra.

Example 2: Evaluation of the Quality Attributes of Disulfide Isoforms of Fremanezumab The following example describes the analysis of the disulfide isoform heterogeneity in fremanezumab drug substance (DS) with respect to the quality attributes relevant to the commercial PFS drug product (DP).

Materials and Methods
Test Materials

Fremanezumab drug substance (DS) was used to generate the isoform-A enriched material and the isoform control. All the reagents used were of pharmaceutical grade at minimum and the instruments used were all in calibrated state at the time of usage.

Reverse Phase High Performance Liquid Chromatography (RP HPLC)

Agilent 1260 Infinity HPLC system was used to perform RP-HPLC. Poroshell 300SB-C8 2.1×75 mm, 5 µm column was set up at 73° C. The mobile phase A consisted of 0.1% TFA and 99.9% HPLC water and the mobile phase B consisted of 70% 2-Propanol, 20% Acetonitrile, 0.1% TFA and 9.9% HPLC water. Flow rate was set to 0.5 mL/min. The test samples were diluted with Millipore water to 0.6 mg/mL and placed in autosampler maintained at 4° C. Injection volume was 10 µL. Gradient elution was performed with a total run time of 18.5 minutes. Detection was by UV at 214 nm. Samples were analyzed in single replicates. The chromatograms generated were used for qualitative comparison to confirm their targeted isoform distribution, and then peaks were integrated for quantitative assessment of their isoform distribution.

Peptide Mapping

The fremanezumab DS, isoform control and isoform-A enriched material were each incubated at 1 mg/mL protein concentration with 4M GuHCl, 0.1 M Tris-HCl at pH 7.5 and 10 mM Iodoacetamide for 30 minutes at 25° C. to alkylate unpaired cysteines. Then, the buffer was exchanged to 4 M Urea, 0.05 M Tris-HCl pH 7.5 by using Zeba Spin Desalting Columns (7K MWCO) and Trypsin was added to the mixture (Trypsin:Protein ratio 1:20). The resulting mixture was incubated at 37° C. for 2 hours and afterwards it was diluted 2-fold with 0.05 M Tris-HCl pH 7.5. Subsequently, the reaction mixtures were incubated at 25° C. for 18 hours. The obtained proteolytic mixtures were analyzed by RP-HPLC-MS with full mass scan (Q Exactive Plus). Briefly, Acquity UPLC BEH C18 column (Cat. No. 186003555, Waters) was used and a gradient of 0-40.2% of 0.02% TFA in ACN was applied over 116.5 min. Mobile phase A was 0.02% TFA in water. Extracted Ion Chromatograms (EIC) for the following three signature peptides were generated:
1) A form peptide 224-249(H)/224-249(H)
2) A/B form peptide 212-214(L)/127-138(H)/224-249(H)/224-249(H)
3) B form peptide 212-214(L)/212-214(L)/127-138(H)/127-138(H)/224-249(H)/224-249(H)

Size Exclusion Chromatography (SEC)

TOSOH TSKgel SuperSW mAb HR 7.8 mm ID×300 mm, 4 µm column was set at 30° C. Mobile phase consisted of 200 mM sodium phosphate and 50 mM sodium chloride at pH 7.0. Test samples were diluted to 3.5-5 mg/mL with the mobile phase and injected with 12 µL injection volume. Isocratic elution at a flow rate of 0.7 mL/minute was used to run the samples. Run time was set to 25 minutes. Detection was by UV at 280 nm.

SEC-Multi-Angle Light Scattering (SEC VIALS)

The chromatographic conditions are similar to those employed for SEC, except that 20 µL injection volume was used per sample. Light scattering and refractive index detections were additionally employed to UV at 280 nm. Bovine Serum Albumin (BSA) standard was used to normalize and align the MALS system before data processing. Molar mass results were collected for each detected peak along with % area results from the UV signal.

Non-Reduced Capillary Gel Electrophoresis (CGE-NR)

Samples were diluted with SDS-MW sample buffer, 250 mM IAM and internal standard solution. The final concentration of diluted samples was 5-10 mg/mL. Samples were analyzed with a Biacore instrument.

Dynamic Light Scattering (DLS)

Samples were diluted with formulation buffer to predetermined concentrations and centrifuged to settle any suspended matter. The supernatant was aliquoted into a 384 well plate with 30 µL into each well and further centrifuged to remove air bubbles. Each well was analyzed by 10 acquisitions, each of 5 seconds acquisition time. For each material type, triplicate sample preparation and testing was performed. The Z-average hydrodynamic radius and polydispersity index (PDI) were reported.

Micro Flow Imaging (MFI)

Test samples were prepared in triplicates by diluting 4 times using sterile filtered Millipore water, and loaded in a 96 well plate for analysis by MFI equipped with Bot1 autosampler. The data was analyzed using an aspect ratio filter of <0.85 to avoid counts of silicon oil droplets or air bubbles.

Viscosity

The v-ROC initium viscometer was used for viscosity measurement at 22° C. 1004 of each sample was pipetted into glass vials, sealed and placed in sample holder. The instrument performance was verified with an aqueous viscosity standard, both pre and post sample runs. Each viscosity measurement included preset recipe of sample loading, measurement and cleaning methods. In every run, the sample viscosity was measured in ten repeated steps. As the channel flow was established in the first 2 steps of a measurement, data from the last eight steps were averaged and reported, to avoid any artifact in instrument measurements.

Break Loose and Glide Force (BLGF)

The BLGF of pre-filled syringes was measured with Instron instrument. Plunger rod was screw tightened on to rubber stopper and a 53.0 mm/min displacement rate was employed to expel syringe contents. The sample was collected in glass vials and labelled appropriately for other analyses. Duplicate measurements were made for each material type.

Differential Scanning Calorimetery (DSC)

Microcal VP-Capillary DSC was used for thermal stability evaluation of materials by calorimetric method. All samples were diluted using formulation buffer to 1 mg/mL nominal protein concentration. Formulation buffer and test sample were transferred into reference and sample wells, respectively, and injection volume was set at 400 µL. Temperature was ramped at 0.7° C./min. All samples were analyzed in triplicates. A molecular weight of 148.146 KDa was used for data analysis, which was performed by the manufacturer's software (Origin).

Isothermal Chemical Denaturation (ICD)

HUNK instrument was used to determine ΔG and ΔΔG trend by ICD technique. Each experiment was performed in triplicates on fremanezumab DS and both isoform materials. Formulation buffer was initially prepared at 2× concentration and was used to prepare final buffer solution and 6M GuHCl solution, which was used as the denaturation solution. pH of the buffer and denaturant solutions were maintained at 5.5±0.1. Multiple protein samples with a concentration range of 4 through 100 mg/mL were prepared by diluting the DS material with the formulation buffer. Buffer and denaturant solutions were filled appropriately in the respective 96 well plates and protein unfolding was monitored by fluorescence. Molecular denaturation of fremanezumab involved multiple unfolding transitions before it was completely denatured. Averaged F values specific to each material type was used in data analysis. A ΔG threshold value of 0.6 K. Cal/mol was used to account for any method variability and define the aggregation pathway for all the unfolding transitions.

Characterization of the Test Samples

Figure 6:
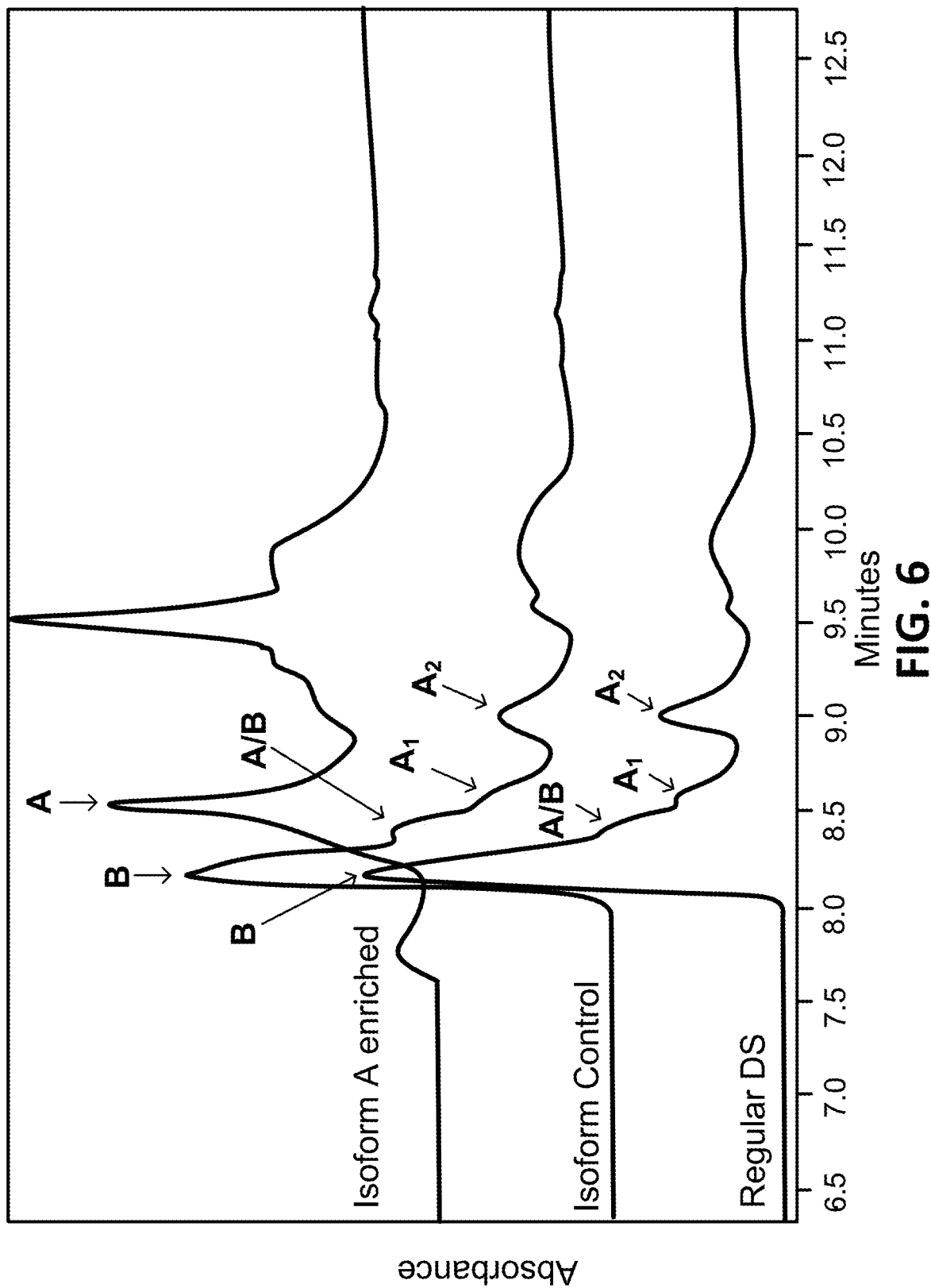
FIG. 6 is an RP-HPLC chromatogram showing profiles of fremanezumab drug substance (DS), the isoform control, and the isoform-A enriched materials.

The isoform-A enriched material was characterized together with the isoform control and fremanezumab DS by RP-HPLC and peptide mapping to confirm their isoform distribution. FIG. 6 shows chromatograms of the isoform-A enriched material, the isoform control, and the fremanezumab DS. The high isoform B content in the isoform control and the fremanezumab DS, and enrichment of isoform A in the isoform-A enriched material was evident from their RP-HPLC chromatographic profiles. Table 1 shows quantitative distribution of the isoforms in each of the final materials.

TABLE 1

Quantitative Distribution of Isoforms as Determined by RP-HPLC*

| Sample | % Isoform B | % Isoform A/B | % Isoform A (A1 + A2) |
|---|---|---|---|
| Fremanezumab DS | 59.6 | 14.1 | 23.9 |
| Isoform Control | 53.5 | 19.5 | 25.0 |
| Isoform-A Enriched Material | ND | 8.4 | 79.0 |

*The values in Table 1 were obtained by an intact RP-HPLC method using a different column and chromatography conditions than the RP-HPLC method described in Example 1 (wherein the antibodies are cleaved prior to RP-HPLC). This method is better suited for resolution of isoform A species whereas the FabRICATOR RP-HPLC method of Example 1 is better suited for resolution of isoform B. Nevertheless the data from the intact RP-HPLC is valid as it was a controlled study with samples tested side-by-side. The intact RP-HPLC was utilized to better monitor the enrichment of isoform A species.

Figure 7A:
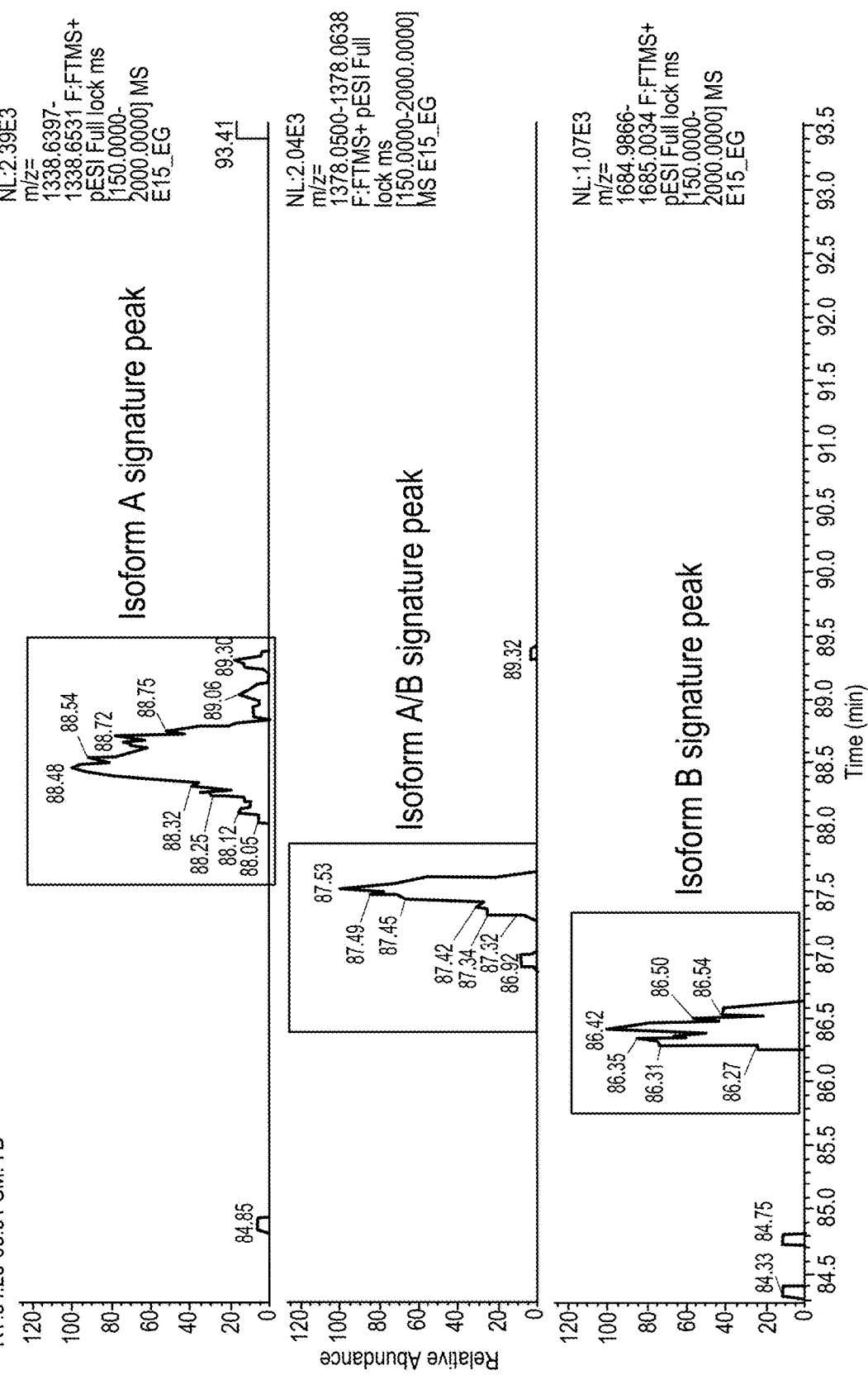
FIGS. 7A-7C show peptide mapping results for the test materials.
Figure 7B:
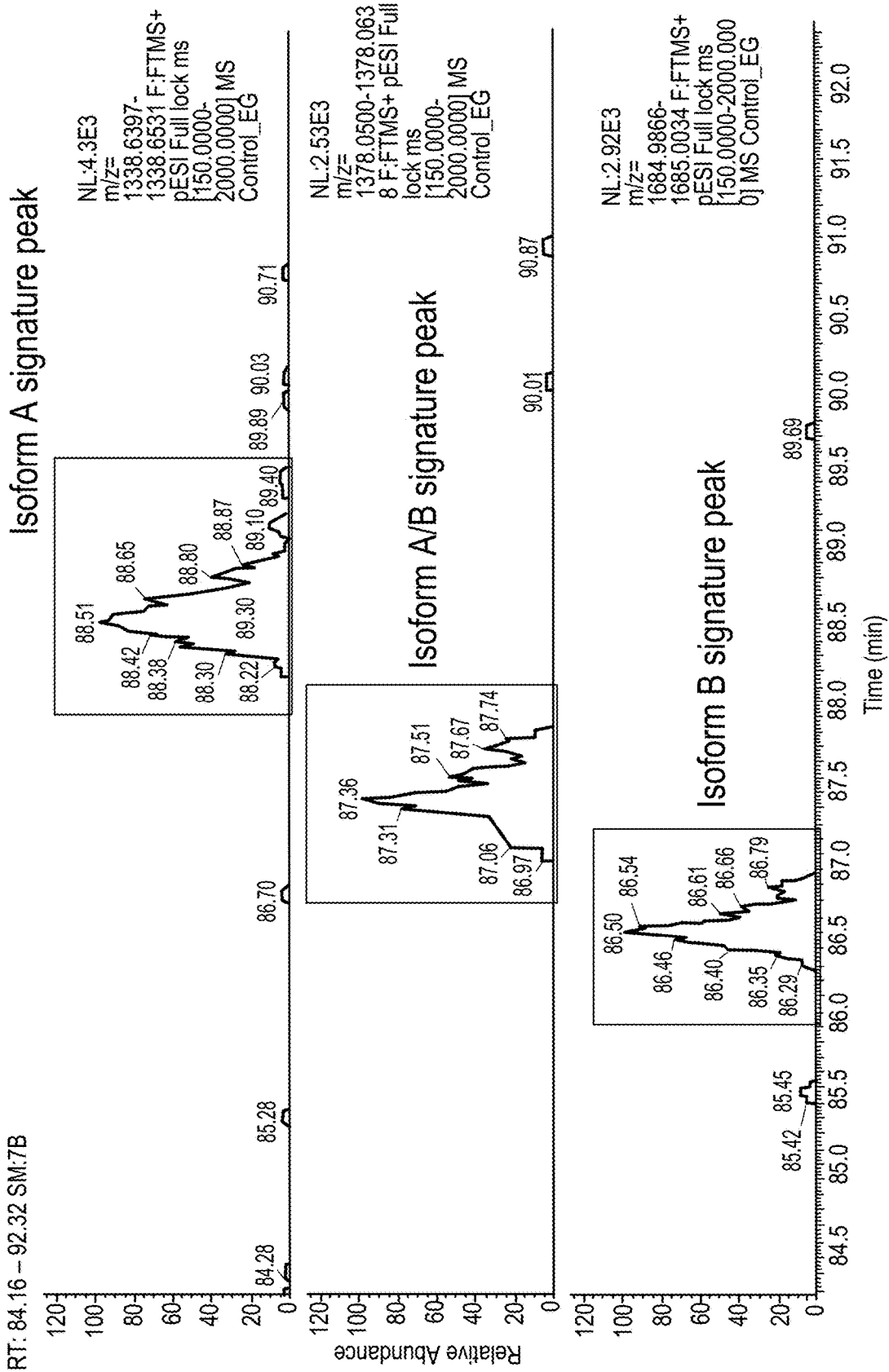
Figure 7C:
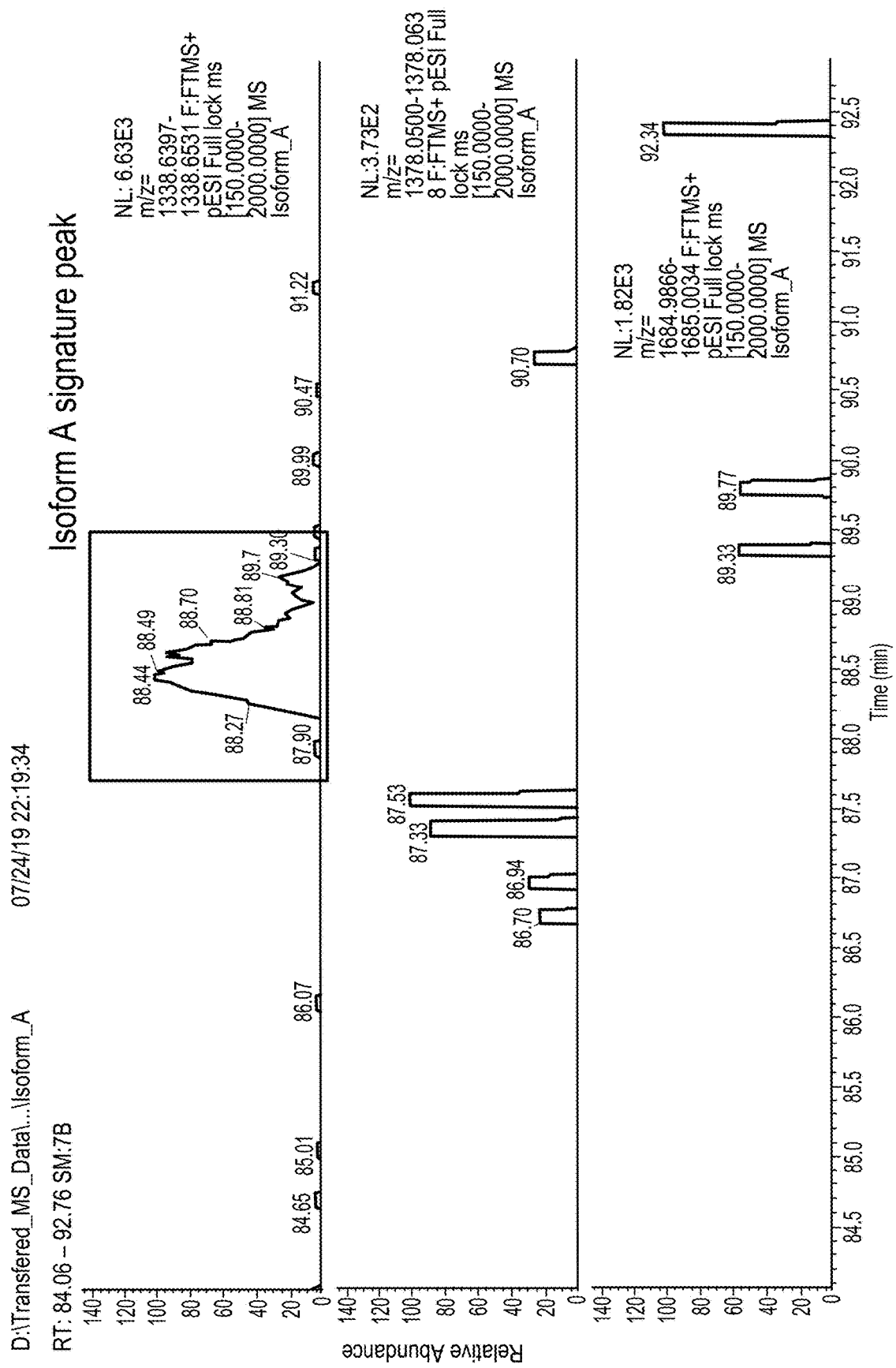

The RP chromatograms of the proteolytic mixtures were examined for the signature peaks of the digested peptides. The retention time for A, A/B and B isoform peptides were 88.4, 87.4 and 86.4 minutes, respectively. As shown in FIGS. 7A-7C, all the characteristic peptide peaks were observed in the fremanezumab DS and the isoform control, whereas only peptide A and A/B signature peaks were observed in isoform-A enriched material. The results further compliment the isoform quantitation levels as shown in Table 1.

The fremanezumab DS, isoform control, and enriched isoform-A material were further concentrated to around 165 mg/mL, matching the upper specification limit of the commercial DP for protein concentration (150±15 mg/mL). Approximately 5 mL of each material was prepared and the concentrations achieved are shown in Table 2. These high concentrated test materials were used in the studies described below.

TABLE 2

Protein Concentration of High Concentrated Materials

| Material | Initial concentration (mg/mL) | Final concentration (mg/mL) |
|---|---|---|
| Fremanezumab DS | 150.6 | 166.7 |
| Isoform Control | 37.9 | 165.8 |
| Isoform-A Enriched | 42.1 | 163.3 |

Evaluation of the Test Materials for Aggregation

Aggregation in the fremanezumab DS, isoform control, and isoform-A enriched materials was analyzed by size exclusion chromatography (SEC), SEC with multi-angle light scattering (MALS), non-reduced capillary gel electrophoresis (CGE) and sub-visible particle analysis by microflow imaging (MFI). Further, the materials were subjected to agitation and freeze-thaw processes in the final container closure configuration of the commercial product (1.5 mL material filled in to 2.25 mL Ompi EZ Fill syringe) before they were aliquoted for analysis of aggregation by the same methods. Agitation was carried out at 300 rpm at 2-8° C. for 72 hours, and freeze-thaw was carried out for 3 cycles, each consisted of 5 hours freezing and 2 hours thawing at minimum.

SEC

Figures 8A, 8B, 8C:
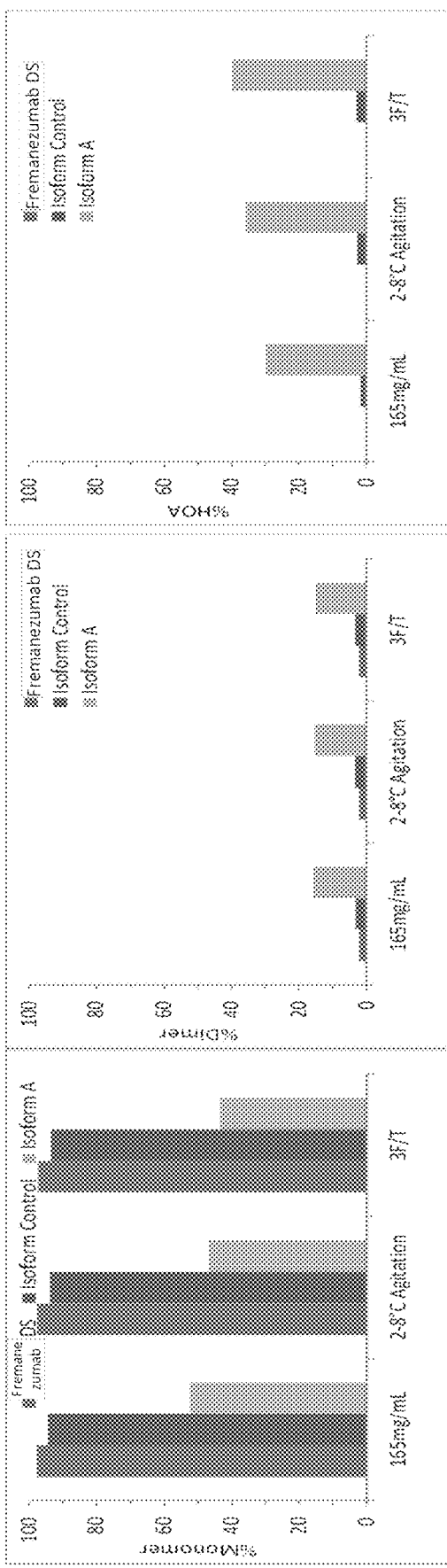
FIGS. 8A-8C show size variants in the fremanezumab DS, isoform control and isoform-A enriched materials at a concentration of 165 mg/mL, after agitation, or after freeze-thaw, as analyzed by SEC.

The soluble size variants in fremanezumab DS, isoform control and isoform-A enriched materials as measured by SEC are shown in Table 3. As shown in FIGS. 8A-8C, the fremanezumab DS and isoform control had similar monomer profile with a slight drop in monomer purity in the isoform control. The isoform-A enriched material had decreased monomer purity to less than 50%, corresponding to higher dimer and HOA levels. This difference in size purity was further increased after agitation or freeze-thaw processes, where an increase in the percentage of HOA was observed in isoform-A enriched material (FIG. 8C).

TABLE 3

Size Variants Levels Monitored with SEC Method in Fremanezumab Isoform study

| Material type | Condition | HOA | Dimer | Main peak | LMW species |
|---|---|---|---|---|---|
| Fremanezumab DS | 165 mg/mL | 0.1 | 2.1 | 97.8 | <LOQ |
| | 2-8° C. Agitation | 0.1 | 2.1 | 97.6 | 0.1 |
| | 3F/T | 0.1 | 2.2 | 97.3 | <LOQ |
| Isoform Control | 165 mg/mL | 1.7 | 3.2 | 94.5 | <LOQ |
| | 2-8° C. Agitation | 2.6 | 3.3 | 93.8 | <LOQ |
| | 3F/T | 3.0 | 3.2 | 93.5 | <LOQ |

TABLE 3-continued

Size Variants Levels Monitored with SEC Method in Fremanezumab Isoform study

| Material type | Condition | HOA | Dimer | Main peak | LMW species |
|---|---|---|---|---|---|
| Isoform-A Enriched | 165 mg/mL | 29.8 | 15.7 | 52.5 | 0.2 |
| | 2-8° C. Agitation | 35.8 | 15.4 | 47.0 | <LOQ |
| | 3F/T | 39.8 | 15.0 | 43.6 | 0.1 |

SEC-MALS

Figure 9A:
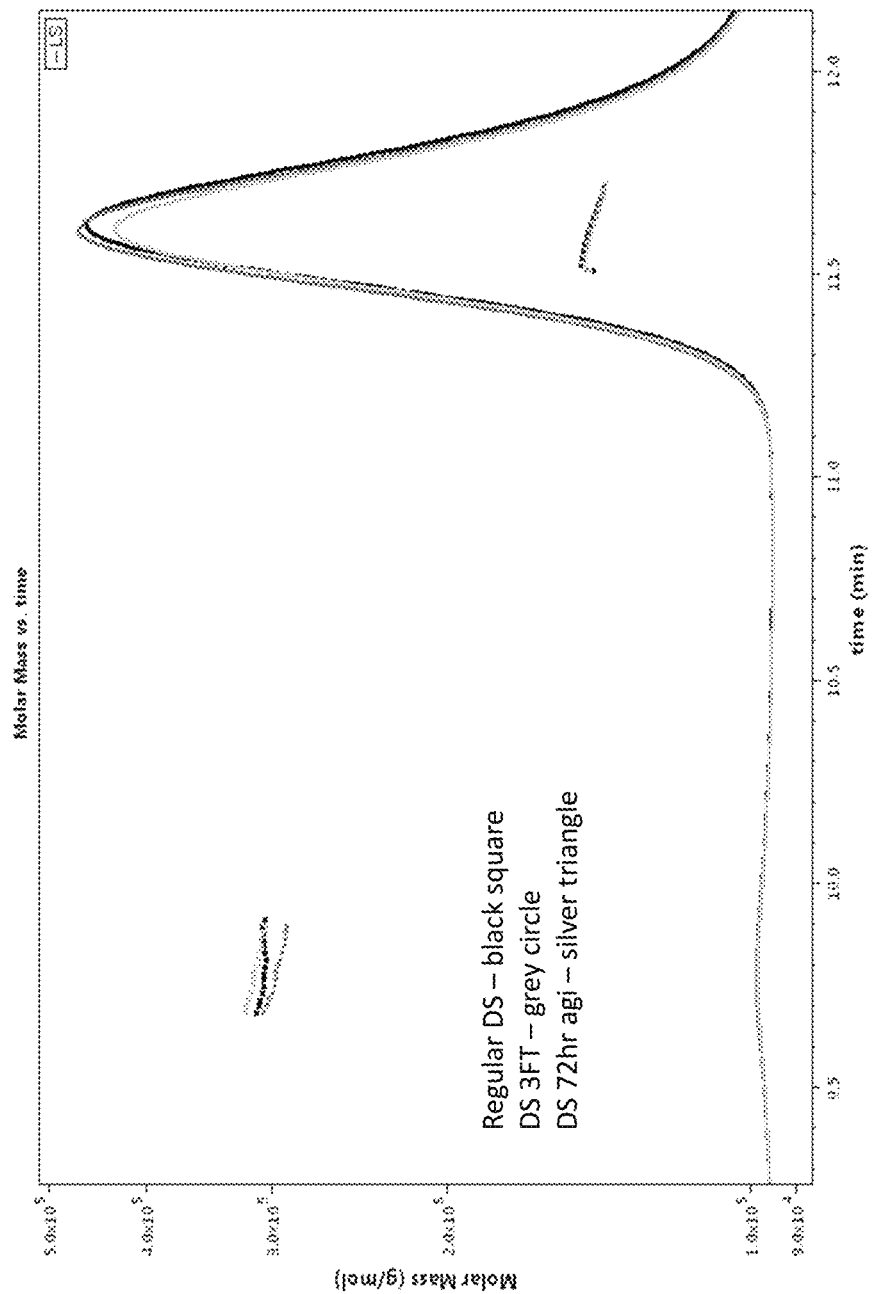
FIGS. 9A-9C show molar mass of the size variants in the isoform materials as analyzed by SEC-MALS.
Figure 9B:
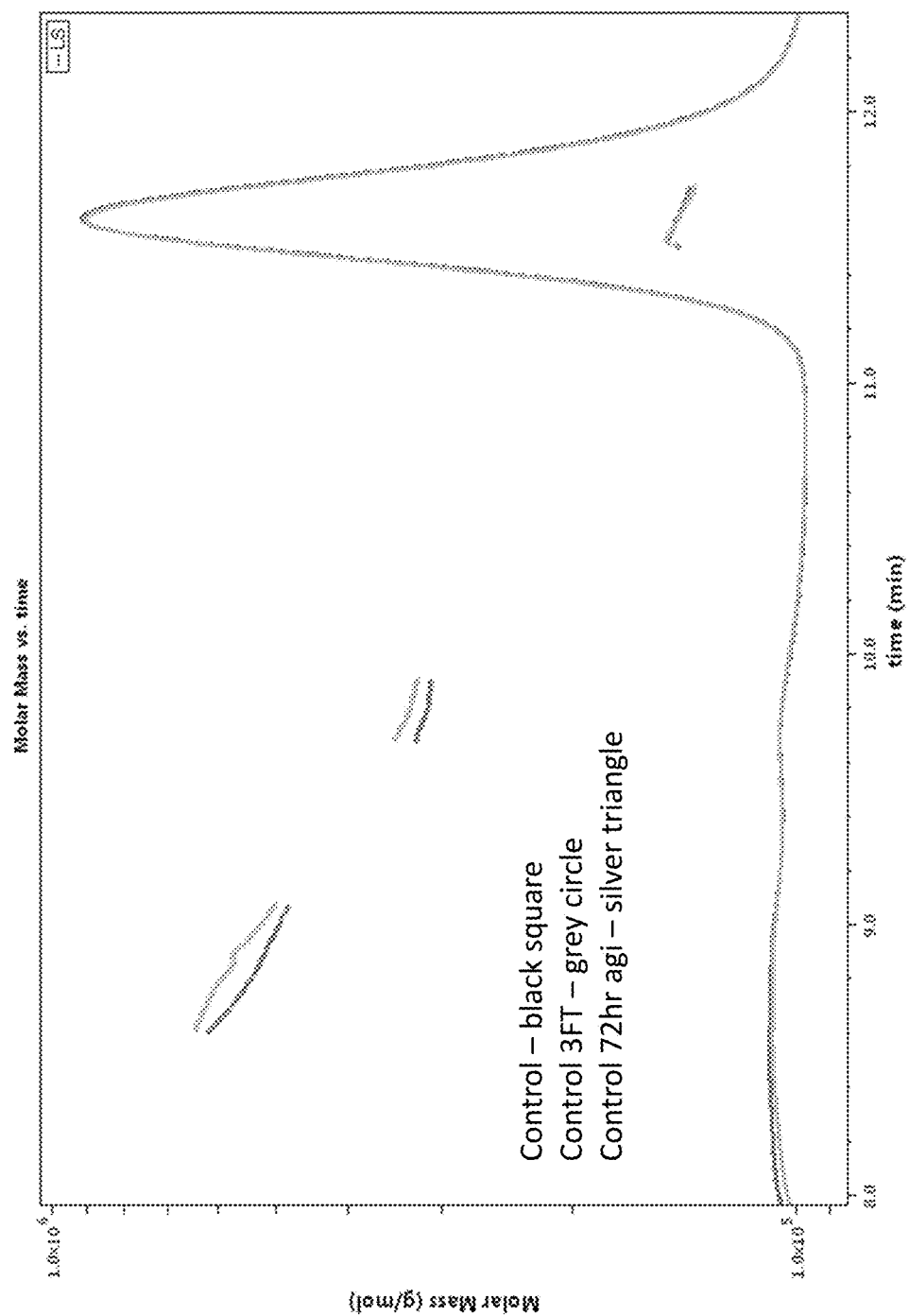
Figure 9C:
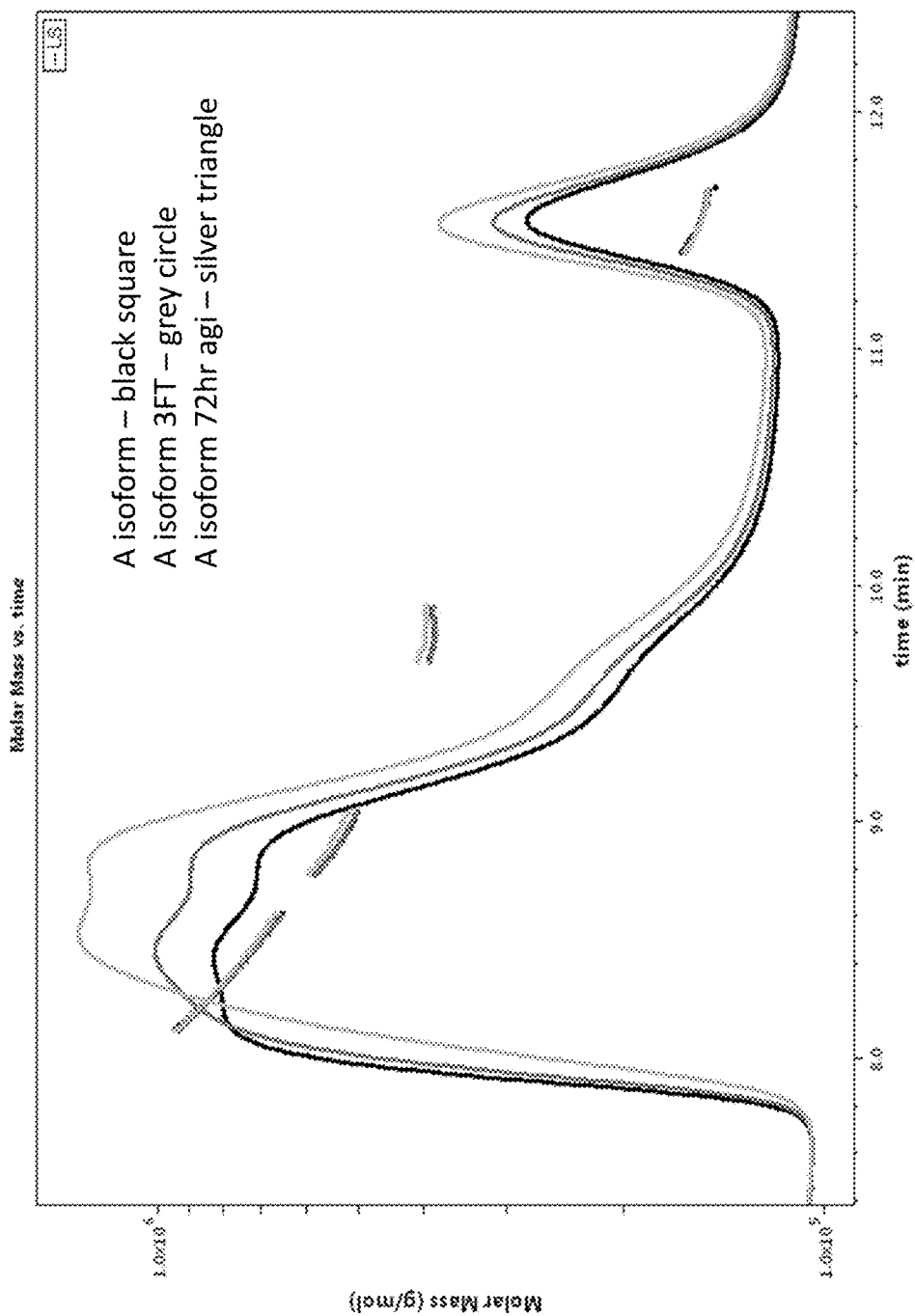
Figure 10:
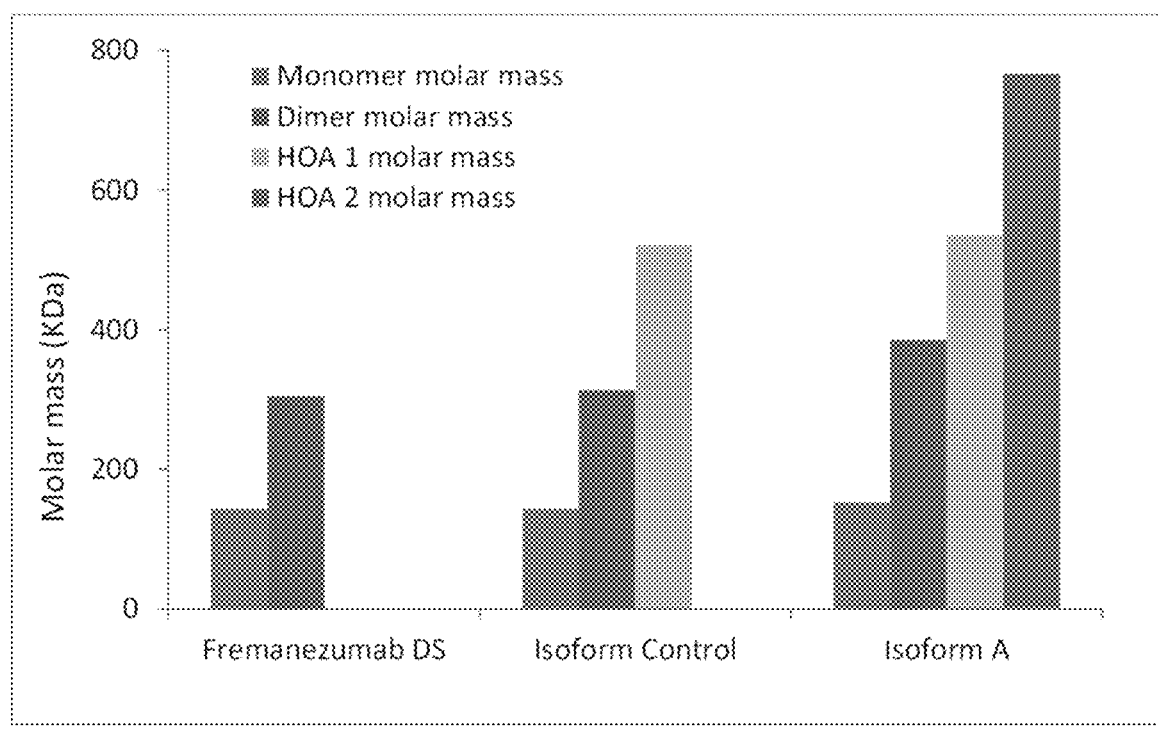
FIG. 10 is a diagram comparing molar mass of monomers, dimers, HOA1 and HOA2 in the fremanezumab DS, the isoform control, and the isoform-A enriched materials.

Since HOA mainly contributed to the differences in aggregation status of the materials, especially after agitation and freeze-thaw, the materials were further characterized by SEC-MALS to understand the molar mass of aggregates. As shown in Table 4 and FIGS. 9A-9C, all the study materials had two common peaks each with a molar mass of ~143 kDa and ~300 kDa, corresponding to monomer and dimer species, respectively. A third peak with a molar mass of 520-580 kDa was observed in the isoform control, which corresponds to a higher order aggregate of unknown composition. However, this species was observed at very low level (around 3%) and there was no further change upon agitation and freeze-thaw processes. Thus, size purity of the isoform control was similar to that of the fremanezumab DS, with ≥95% monomer and about 2% dimer. In contrast, the isoform-A enriched material revealed a very different size heterogeneity, including an additional fourth peak of ~760 kDa molar mass. The level of the monomer peak was around 40-50% with a molar mass of 154 kDa, and the dimer peak was detected as between 7-10% with a molar mass closer to 400 kDa. The HOA peaks were co-eluting, but at least two different species could be detected with molar masses around 530-580 kDa and 760 kDa, with a level of around 20% and 30%, respectively. The composition of these HOA peaks was unknown. However, similar to the fremanezumab DS and isoform control, no significant changes in size heterogeneity was observed after agitation and freeze-thaw for the isoform-A enriched material. FIG. 10 is a diagram comparing the molar mass of monomers, dimers, HOA1 and HOA2 in the fremanezumab DS, the isoform control, and the isoform-A enriched materials. Higher molar mass of aggregated species were detected in the isoform-A enriched material.

CGE-NR Analysis

Results from the CGE-NR analysis are shown in Table 5. The observations were consistent with those from the SEC and SEC-MALS studies. Specifically, the isoform control material closely resembled the fremanezumab DS with high intact protein content, whereas the isoform-A enriched material showed a very different size heterogeneity, mainly with increase in the % HMW.

TABLE 5

Size Variants as analyzed using CGE-NR

| Sample | Condition | Purity (%) (125 kDa + IgG) | IgG (%) | HHL (%) or 125 kDa peak | Fragment (%) | HMW (%) |
|---|---|---|---|---|---|---|
| Frem. DS | 165 mg/mL | 99.1 | 95.7 | 3.4 | 0.7 | 0.2 |
| | 2-8° C. Agitation | 99.1 | 96.3 | 2.8 | 0.8 | 0.1 |
| | 3F/T | 99.3 | 97.1 | 2.2 | 0.7 | 0.1 |
| Isoform Control | 165 mg/mL | 98.9 | 96.0 | 2.9 | 1.0 | 0.2 |
| | 2-8° C. Agitation | 99.0 | 96.1 | 2.9 | 0.9 | 0.1 |
| | 3F/T | 98.9 | 96.9 | 2.0 | 1.0 | 0.1 |
| IsoformA | 165 mg/mL | 52.1 | 48.5 | 3.7 | 9.1 | 38.8 |
| | 2-8° C. Agitation | 51.6 | 47.4 | 4.2 | 8.8 | 39.6 |
| | 3F/T | 53.5 | 49.4 | 4.1 | 9.2 | 37.4 |

Dynamic Light Scattering (DLS)

Figure 11B:
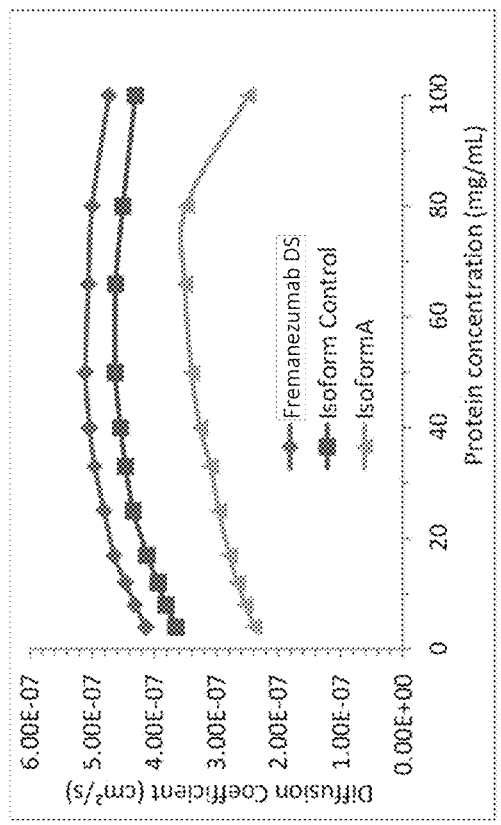
FIGS. 11A and 11B show results from DLS analysis on the test samples.
Figure 11A:
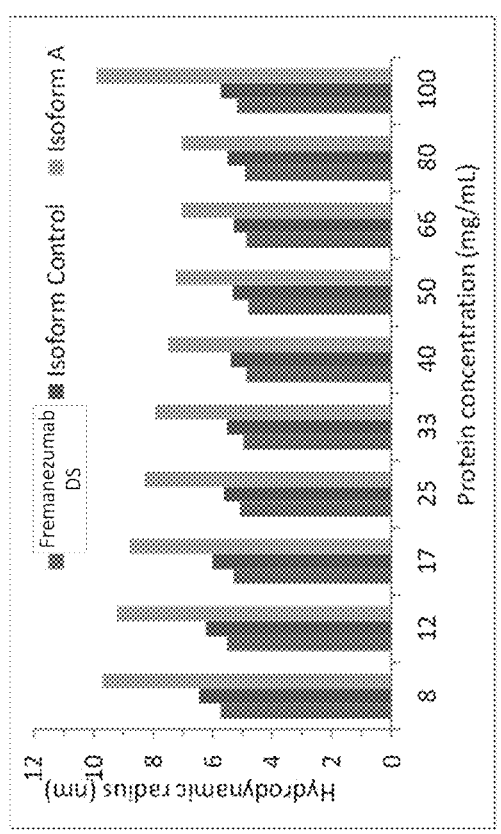

Size distribution of the aggregates in the nano or submicron size range was evaluated by DLS. Results of Z-average size and PDI, along with the diffusion coefficients are shown in Table 6. As shown in FIG. 11A, the hydrodynamic radius of the fremanezumab DS and isoform control were very similar, while the hydrodynamic radius of isoform-A enriched material was higher at all concentrations tested. The diffusion coefficient values of isoform-A enriched material was significantly lower as compared to those of fremanezumab DS or the isoform control, indicating its greater molecular mass (FIG. 11B).

TABLE 1

Molar Mass Evaluation of Size Variants as analyzed using SEC-MALS

| Sample | Condition | Peak 1 - Monomer | | Peak 2 - Dimer | | Peak 3- HOA1 | | Peak 4 - HOA2 | |
|---|---|---|---|---|---|---|---|---|---|
| | | Mw (kDa) | % Area | Mw (kDa) | % Area | Mw (kDa) | % Area | Mw (kDa) | % Area |
| Frem. DS | 165 mg/mL | 143.7 | 98.6 | 305.7 | 1.4 | ND | ND | ND | ND |
| | 2-8° C. Agitation | 143.3 | 98.7 | 311.4 | 1.3 | ND | ND | ND | ND |
| | 3F/T | 143.1 | 98.7 | 295.3 | 1.3 | ND | ND | ND | ND |
| Isoform Control | 165 mg/mL | 144.0 | 94.9 | 313.7 | 1.9 | 521.1 | 3.2 | ND | ND |
| | 2-8° C. Agitation | 143.5 | 95.4 | 332.9 | 1.8 | 576.1 | 2.8 | ND | ND |
| | 3F/T | 143.3 | 95.2 | 314 | 1.8 | 534.3 | 3.0 | ND | ND |
| IsoformA | 165 mg/mL | 153.2 | 39.5 | 385.8 | 6.8 | 535.2 | 21.8 | 766.4 | 32.0 |
| | 2-8° C. Agitation | 153.8 | 40.6 | 399.7 | 7.3 | 554.3 | 22.5 | 769.7 | 29.7 |
| | 3F/T | 153.3 | 39.1 | 384.4 | 7.1 | 535.6 | 22.0 | 760.6 | 31.9 |

TABLE 6

Z-average Radius and $K_D$ Results

| Protein concentration (mg/mL) | Fremanezumab DS | | | Isoform Control | | | Isoform A | | |
|---|---|---|---|---|---|---|---|---|---|
| | Hydrodynamic radius (nm) | % PD | Diffusion Coefficient (cm²/s) | Hydrodynamic radius (nm) | % PD | Diffusion Coefficient (cm²/s) | Hydrodynamic radius (nm) | % PD | Diffusion Coefficient (cm²/s) |
| 4 | 5.9 | 13.8 | 4.1347E−07 | 6.7 | 21.4 | 3.6557E−07 | 10.3 | 20.6 | 2.393E−07 |
| 8 | 5.7 | 8.8 | 4.311E−07 | 6.5 | 15.1 | 3.816E−07 | 9.7 | 16.9 | 2.53633E−07 |
| 12 | 5.5 | 7.7 | 4.461E−07 | 6.2 | 13.7 | 3.941E−07 | 9.2 | 13.7 | 2.66567E−07 |
| 17 | 5.3 | 6.3 | 4.6493E−07 | 6.0 | 11.7 | 4.1163E−07 | 8.8 | 14.6 | 2.79633E−07 |
| 25 | 5.1 | 6.7 | 4.809E−07 | 5.6 | 11.4 | 4.34E−07 | 8.3 | 17.8 | 2.96467E−07 |
| 33 | 5.0 | 6.3 | 4.9583E−07 | 5.5 | 12.0 | 4.4657E−07 | 7.9 | 19.5 | 3.098E−07 |
| 40 | 4.9 | 8.6 | 5.0417E−07 | 5.4 | 17.2 | 4.542E−07 | 7.5 | 23.4 | 3.26667E−07 |
| 50 | 4.8 | 7.3 | 5.105E−07 | 5.3 | 17.2 | 4.628E−07 | 7.2 | 28.1 | 3.40267E−07 |

Micro Flow Imaging (MFI)

Figure 12A:
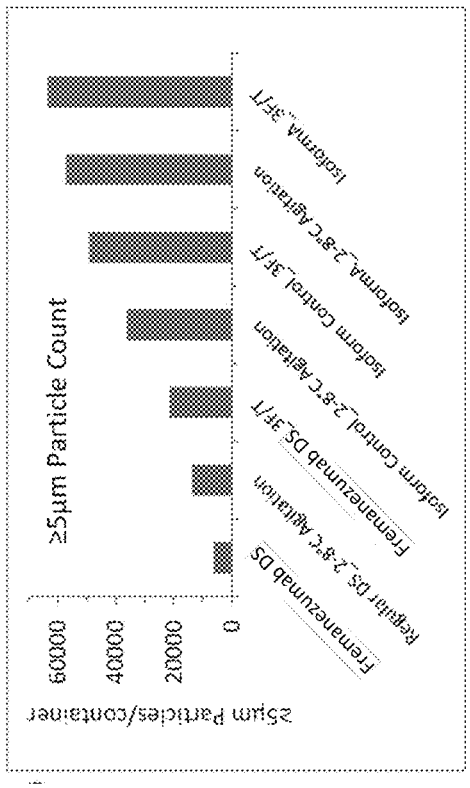
FIGS. 12A-12D show sub-visible particle counts in the test samples as analyzed by micro-flow imaging.
Figure 12B:
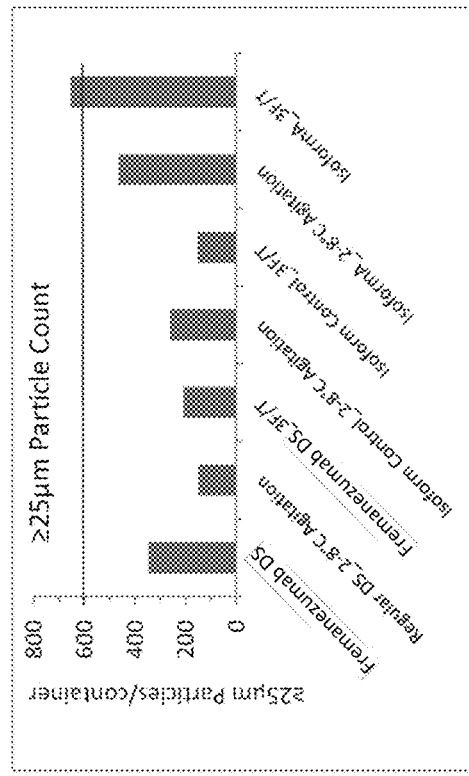
Figure 12C:
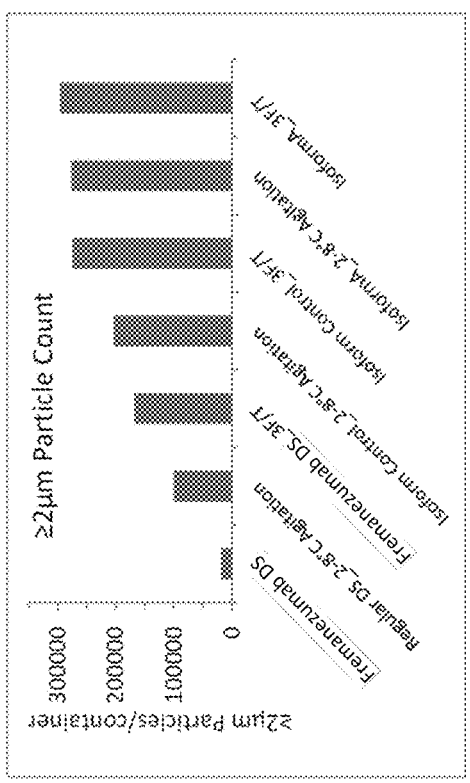
Figure 12D:
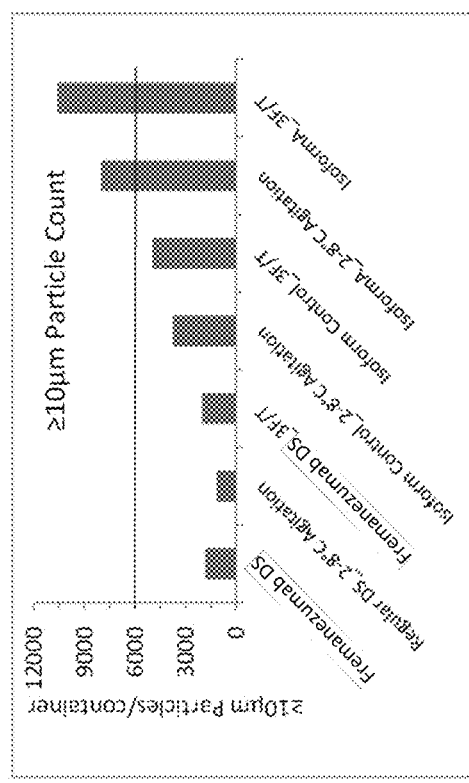

The test samples were further analyzed by MFI for aggregates or particles in the sub-visible size range. Results are shown in Table 7. Overall, as plotted in FIGS. 12A-12D, particulate counts in the isoform-A enriched material were higher than the fremanezumab DS and the isoform control materials, especially after agitation and freeze-thaw processes, which are known to cause particle formation. It is to be noted that, though MFI is a more sensitive method than light obscuration, particles at ≥10 μm and ≥25 μm size ranges in the isoform-A enriched material exceeded their USP limits (not more than 6000 and 600 particles/container for ≥10 μm and ≥25 μm particles, respectively), whereas they remained below these limits for the fremanezumab DS and the isoform control materials (Table 7, and FIGS. 12C and 12D).

ent protein concentrations was measured to evaluate the differences in their rheological profile. Break Loose and Glide Force (BLGF) of the syringes filled with the isoform materials at a 1.5 mL fill volume were also measured to confirm the impact of viscosity differences.

Viscosity

Results from the viscosity analysis for the fremanezumab DS, isoform control, and isoform-A enriched materials at varied protein concentration are shown in Table 8. The fremanezumab DS and isoform control material had very similar viscosity at all of the protein concentrations measured, while isoform-A enriched material had significantly higher viscosity when protein concentration was above 100

TABLE 7

Sub-Visible Particulate Count in Fremanezumab Isoform Study Samples

| Sample | Condition | Particles/PFS | | | | | | | |
|---|---|---|---|---|---|---|---|---|---|
| | | ≥2 μm | Std.dev | ≥5 μm | Std.dev | ≥10 μm | Std.dev | ≥25 μm | Std.dev |
| Fremanezumab DS | 165 mg/mL | 18843 | 813 | 6186 | 577 | 1833 | 160 | 344 | 69 |
| | 2-8° C. Agitation | 100279 | 3316 | 13696 | 470 | 1130 | 153 | 147 | 83 |
| | 3F/T | 168259 | 7223 | 21524 | 1161 | 2010 | 327 | 206 | 56 |
| Isoform Control | 2-8° C. Agitation | 203920 | 8175 | 36128 | 1223 | 3731 | 271 | 261 | 21 |
| | 3F/T | 275792 | 1682 | 49159 | 633 | 4930 | 396 | 152 | 63 |
| Isoform-A Enriched | 2-8° C. Agitation | 276751 | 17748 | 57208 | 3396 | 8006 | 190 | 467 | 21 |
| | 3F/T | 296272 | 14267 | 63483 | 4513 | 10600 | 907 | 654 | 62 |

Evaluation of Physical Properties

Figure 13:
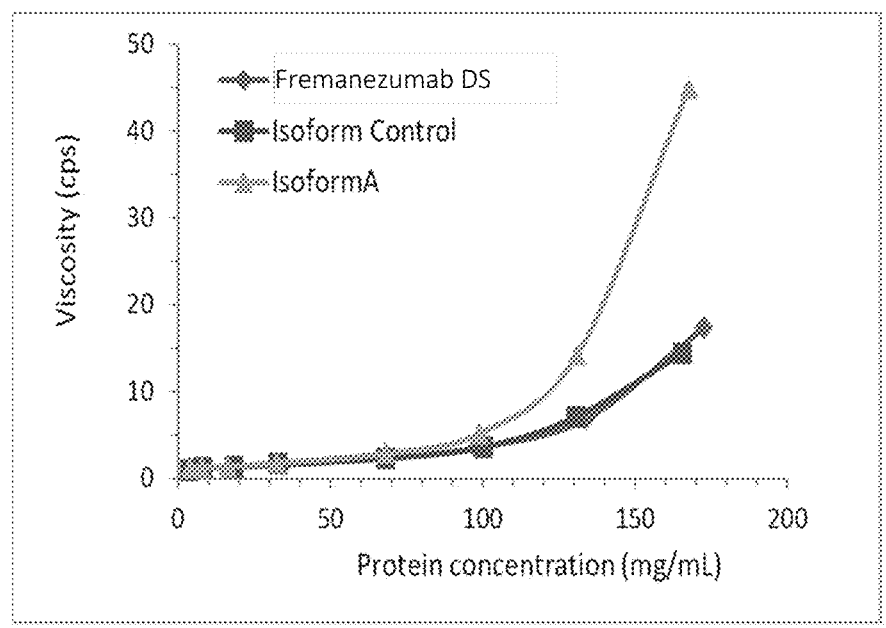
FIG. 13 shows viscosity profiles of the test samples at varying protein concentrations.

The increased hydrodynamic radius in isoform-A enriched material as determined by DLS could impact viscosity, which could further influence syringeability of a PFS. Therefore, viscosity of the isoform materials at differmg/mL (Table 8 and FIG. 13). Within the commercial specifications of the protein concentration, the viscosity of isoform-A enriched material was >2 fold at 135 mg/mL and >2.5 fold at 165 mg/mL, compared to the fremanezumab DS or isoform control material.

TABLE 8

Results from viscosity analysis for the test samples

| Target Protein concentration (mg/mL) | Fremanezumab DS | | Isoform Control | | IsoformA | |
|---|---|---|---|---|---|---|
| | Protein concentration (mg/mL) | Viscosity (Cps) | Protein concentration (mg/mL) | Viscosity (Cps) | Protein concentration (mg/mL) | Viscosity (Cps) |
| 4.5 | 3.8 | 1.2 | 3.7 | 0.9 | 3.8 | 1.2 |
| 8.5 | 8.0 | 1.3 | 8.1 | 1.2 | 7.6 | 1.3 |

TABLE 8-continued

Results from viscosity analysis for the test samples

| Target | Fremanezumab DS | | Isoform Control | | IsoformA | |
|---|---|---|---|---|---|---|
| Protein concentration (mg/mL) | Protein concentration (mg/mL) | Viscosity (Cps) | Protein concentration (mg/mL) | Viscosity (Cps) | Protein concentration (mg/mL) | Viscosity (Cps) |
| 17 | 17.8 | 1.4 | 18.2 | 1.3 | 16.2 | 1.4 |
| 33 | 34.5 | 1.6 | 32.7 | 1.7 | 32.5 | 1.8 |
| 66 | 68.0 | 2.4 | 68.2 | 2.3 | 68.1 | 2.9 |
| 100 | 98.0 | 3.5 | 100.4 | 3.6 | 98.9 | 5.2 |
| 135 | 134.0 | 6.9 | 130.6 | 7.1 | 131.1 | 14.2 |
| 165 | 172.6 | 17.4 | 165.6 | 14.4 | 167.7 | 44.9 |

Break Loose and Glide Force (BLGF)

Figure 14:
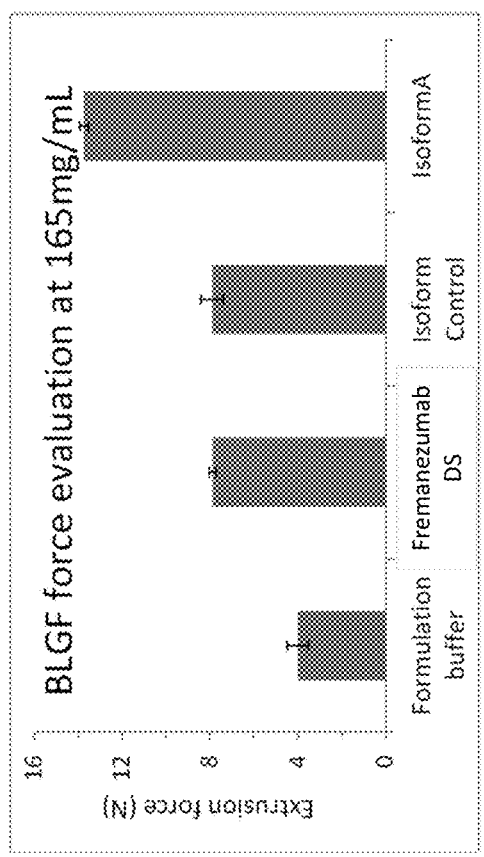
FIG. 14 shows results from the Break loose and glide force analysis for the formulation buffer, fremanezumab DS, isoform control and isoform-A enriched materials.

The BLGF results measured with the Instron instrument are shown in Table 9 and plotted in FIG. 14. BLGF of the syringes filled with the test materials at a 1.5 mL fill volume and a concentration of 165 mg/mL were measured. For any given syringe, the break loose force and the glide force were measured to be the same. Therefore, the results are presented as a single number. About 1.8 fold higher BLGF was recorded for the syringes filled with the isoform-A enriched material compared to those filled with the fremanezumab DS or the isoform control.

TABLE 9

PFS BLGF Results

| | Break Loose Glide Force (N) | | |
|---|---|---|---|
| Material type | Fremanezumab DS | Isoform Control | IsoformA |
| N1 | 7.8 | 8.2 | 13.9 |
| N2 | 7.7 | 7.5 | 13.6 |
| N3 | 8 | N/A | N/A |
| Average (N) | 7.9 | 7.9 | 13.7 |
| Standard deviation | 0.2 | 0.5 | 0.2 |

Evaluation of Thermodynamic Stability

Thermodynamic stability of the isoform materials was evaluated in pursuit of the fundamental conformational differences of the isoforms that could cause increased instability by aggregation. Differential scanning calorimetry (DSC) and isothermal chemical denaturation (ICD) techniques were employed for this purpose.

Differential Scanning Calorimetry (DSC)

Figure 15:
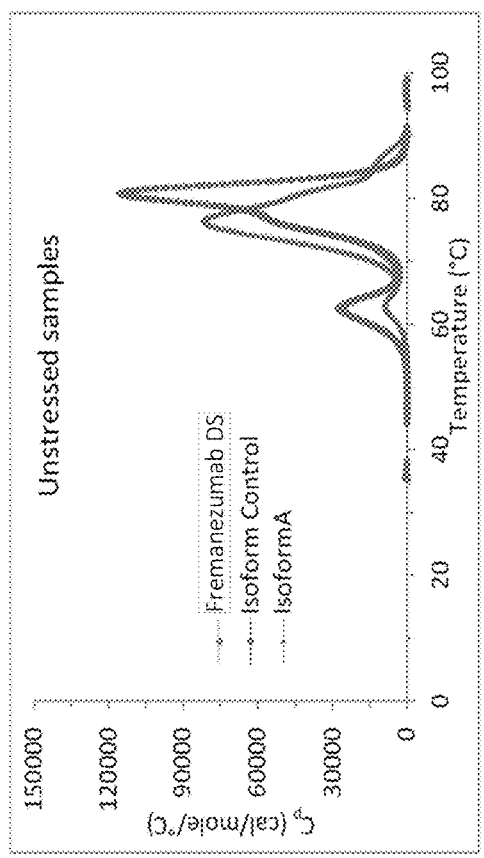
FIG. 15 shows differential scanning calorimetry (DSC) thermograms of the test samples.
Figure 16A:
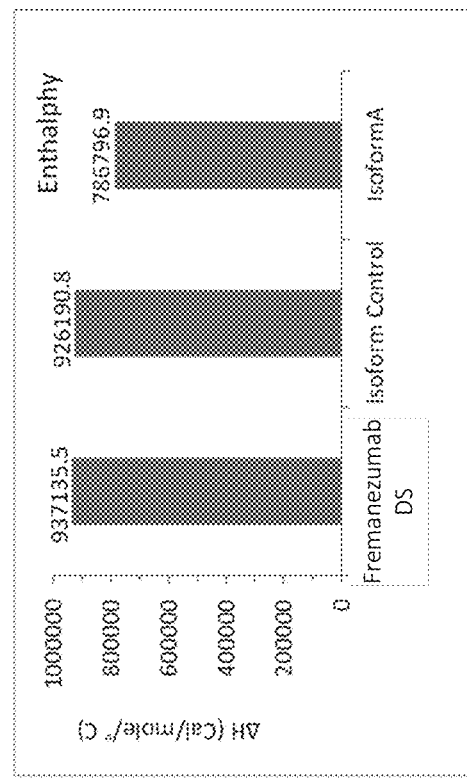
FIGS. 16A and 16B show thermodynamic parameters of the test samples as analyzed by differential scanning calorimetry (DSC).
Figure 16B:
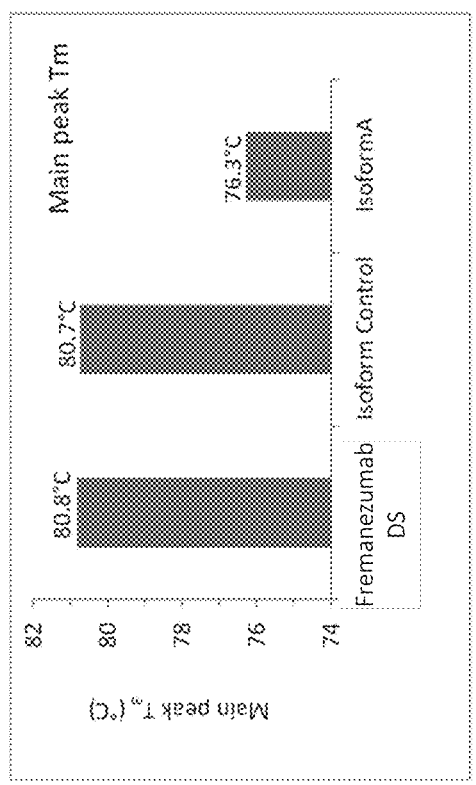

As shown in FIG. 15, thermograms of the fremanezumab DS and isoform control samples were nearly identical. However, isoform-A enriched material resulted in lower melting temperature as well as reduced total enthalpy as quantitatively compared in FIGS. 16A and 16B, indicating that it has lower thermal stability than the fremanezumab DS or the isoform control. Thermograms of each material type remained unchanged after agitation and freeze/thaw stress conditions (data not shown).

The following experiment was performed to evaluate the thermal properties of fremanezumab compositions with varying isoform A: isoform B ratios. In order to achieve the desired ratios, purified isoform materials were initially generated by fractionating the fremanezumab DS. Fractionation of the fremanezumab drug substance was performed with IEC in a pH gradient mode. The fremanezumab drug substance was injected at a 150 mg/mL concentration and multiple 5 mL fractions of isoform A, A/B and B were collected. The fractions were concentrated, followed by buffer exchange into the formulation buffer (Amicon Ultra 30K MWCO tubes were used). The purified isoform fractions were further mixed at certain ratios to prepare native fraction mixtures. Protein concentration of the prepared fractions and fraction mixtures were determined with soloVPE at 280 nm and the isoform composition was measured with RP-LC. The SEC and RP-LC results are shown in Tables 10 and 11 respectively.

TABLE 20

Protein concentration of native fraction materials

| Material type | Measured protein concentration (mg/mL) |
|---|---|
| Isoform A | 32.7 |
| Isoform A/B | 39.9 |
| Isoform B | 54.0 |

TABLE 11

Isoform Composition Measured with RP-LC for Native Fractions and Fraction Mixtures

| Sample ID | Isoform B | IsoformA/B | IsoformA | Isoform A + A/B |
|---|---|---|---|---|
| Native fraction1_Fr1 | 26.7 | 73.3 | | 73.3 |
| Native fraction2_Fr2 | 29.3 | 63.2 | 7.5 | 70.7 |
| Native fraction3_Fr3 | 82.4 | 10.1 | 7.5 | 17.6 |
| 30:70 Fr1:Fr3_Mixture1 | 73.8 | | 26.2 | 26.2 |
| 50:50 Fr1:Fr3_Mixture 2 | 58.6 | | 41.4 | 41.4 |
| 70:30 Fr1:Fr3_Mixture 3 | 47.8 | 38.6 | 13.7 | 52.2 |

The native fractions and their mixtures were subjected to DSC analysis using the Microcal VP-Capillary DSC instrument to evaluate their thermal properties. All samples were diluted with the formulation buffer to about 1 mg/mL concentration. A 0.7° C./min heating rate, equivalent to 42° C./hr, was used in this study. The Mab molecular weight of 148.146 KDa was used for data analysis purposes.

Figures 17A, 17B:
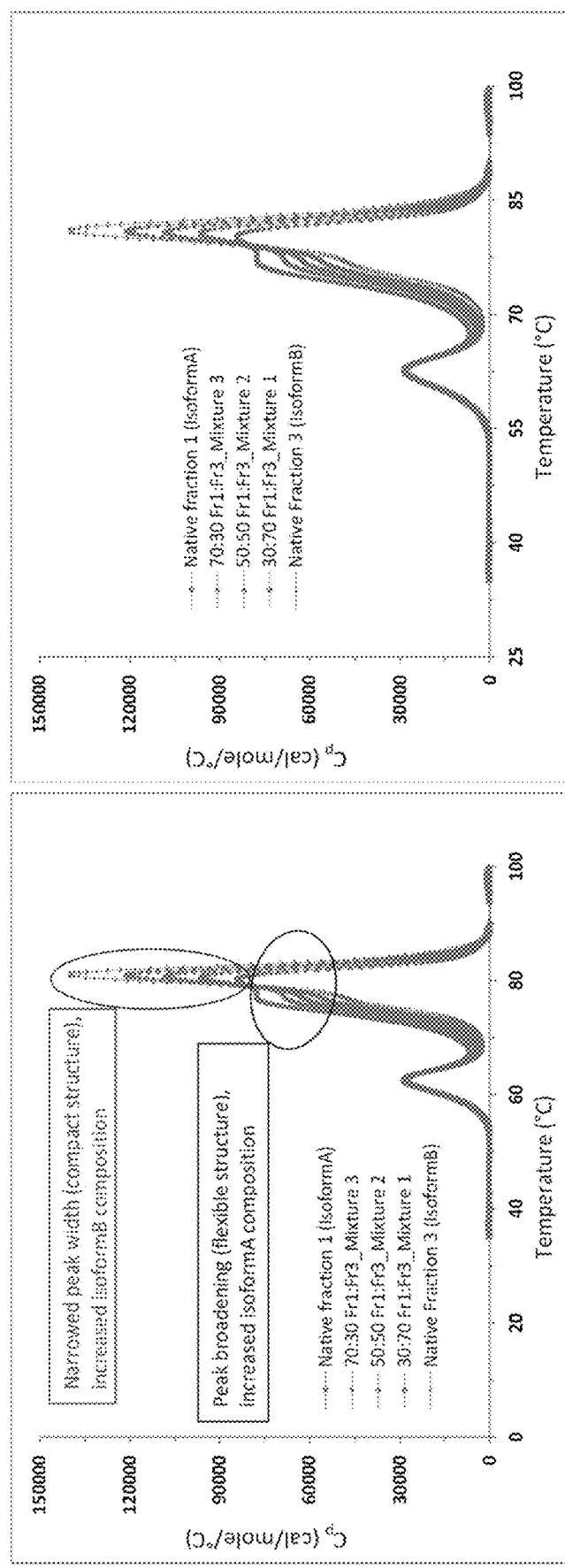
FIGS. 17A-17D show DSC analysis of native fractions and fraction mixtures.
Figure 17D:
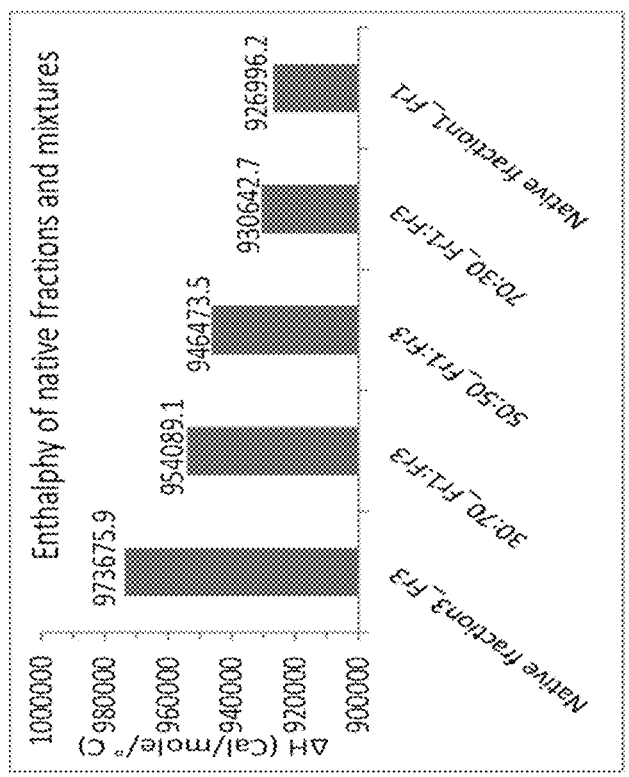
Figure 17C:
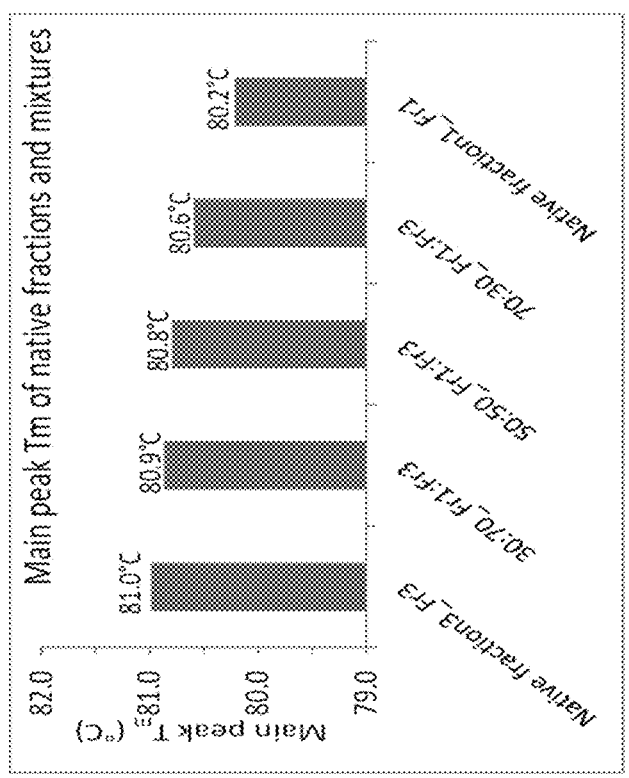

Native fraction 1, native fraction 3, and mixtures of fractions 1 and 3 at a ratio of 70:30, 50:50, or 30:70 were subjected to DSC analysis. FIGS. 17A and 17B show DSC thermograms of each native fraction and fraction mixtures. As shown in FIGS. 17A and 17B, with the increase in the isoform A content, the DSC thermogram broadens with reduced height. This could be due to the flexible structure of isoform A and is accompanied by a reduction in enthalpy and Tm. These results suggest that the energy required to unfold native fraction 1 is lower than native fraction 3. FIG. 17C shows the main peak melting temperatures of the native fractions and fraction mixtures. FIG. 17D shows the enthalpy of native fractions and fraction mixtures.

Results from the DSC analyses described above suggest that increased isoform A content in fremanezumab compositions leads to lower thermal stability.

Isothermal Chemical Denaturation (ICD)

Figure 18A:
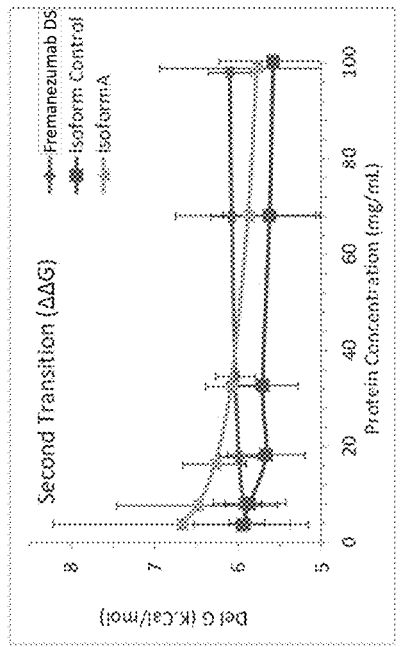
FIGS. 18A-18C show unfolding transitions for the test samples as determined by isothermal chemical denaturation technique.
Figure 18B:
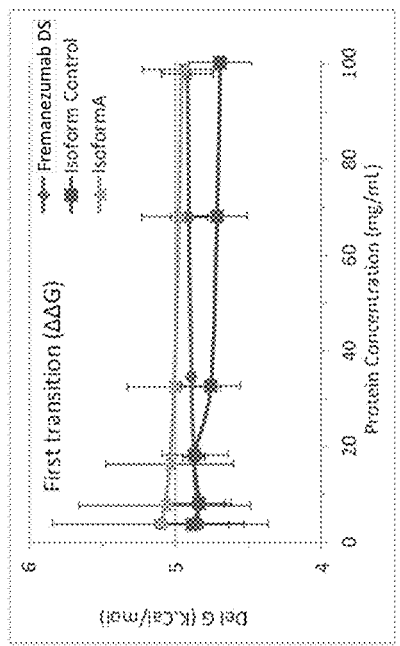
Figure 18C:
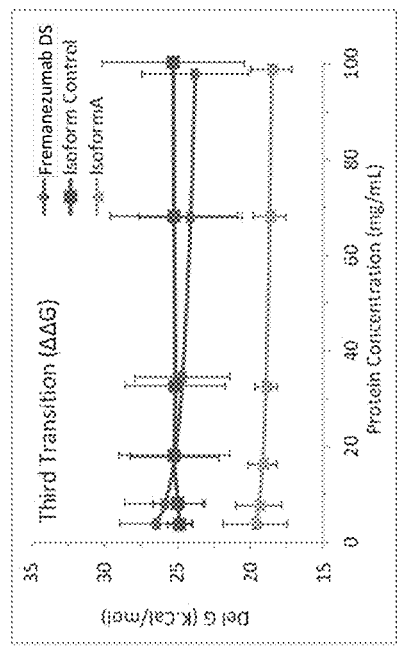

The ICD experiments revealed three transitions of unfolding in all the fremanezumab materials. The free energy of unfolding (ΔG) for each transition at various protein concentrations for the fremanezumab DS, isoform control and isoform-A enriched materials are shown in FIGS. 18A-18C. No significant differences were observed for the first and the second transitions among the materials. However, the ΔG profiles of the third transition showed lower free energy of unfolding for the isoform-A enriched material compared to the fremanezumab DS and the isoform control throughout the protein concentration range, indicating its lower thermodynamic stability than others (FIG. 18C). ΔG of the fremanezumab DS and isoform control remained at comparable levels. Further, no clear trending of ΔG over protein concentration was observed for any of the transitions for all materials, indicating potential similar pathways of aggregation in the isoform materials.

Figures 19A, 19B, 19C:
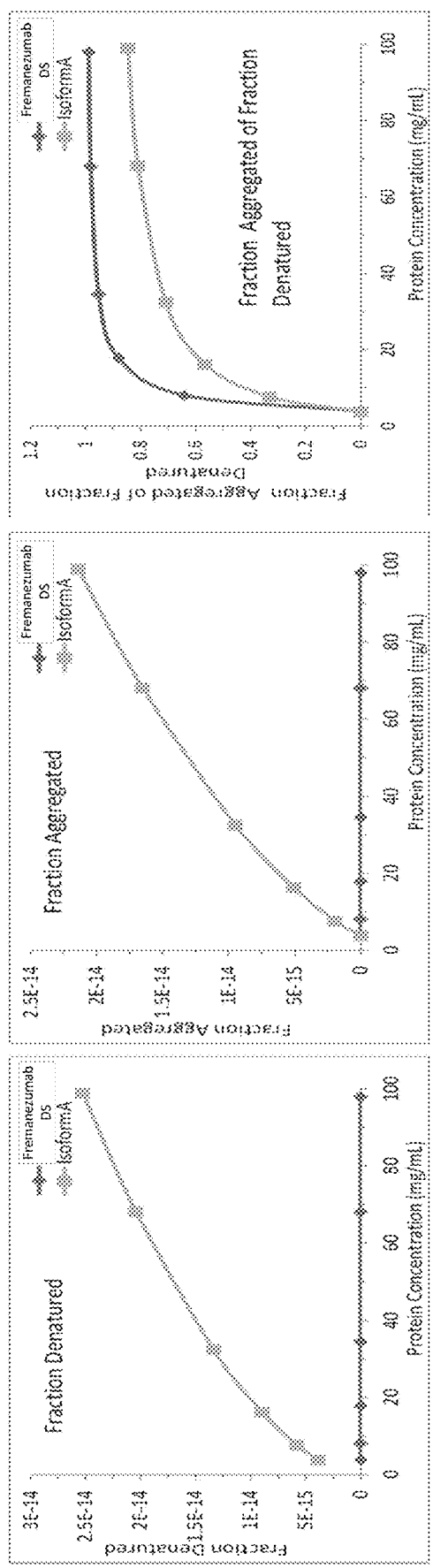
FIGS. 19A-19C are profiles showing the aggregation propensity of the test samples as evaluated by isothermal chemical denaturation technique.

Further analysis of the data to determine % fraction denatured, % fraction aggregated and % fraction of the denatured population that is aggregated, as shown in FIGS. 19A-19C, revealed higher % fractions of denatured and aggregated species in isoform-A enriched material compared to the fremanezumab DS. However, fraction of the denatured species aggregated was more in the fremanezumab DS compared to the isoform-A enriched material.

Discussion

The disulfide isoform A in fremanezumab drug substance (DS) was chemically enriched and characterized by RP-HPLC and peptide mapping. An isoform control material was also generated. The isoform control material was then employed in every study performed to evaluate differences in the test materials, and all test methods confirmed similarity between the isoform control and the fremanezumab DS.

The fremanezumab DS, isoform control, and isoform-A enriched materials were first evaluated for differences in their aggregation status. The evaluation of potential differences in the aggregation propensity included subjecting the materials to agitation and freeze-thaw prior to analysis. Multiple methods were then used to measure aggregation at different size ranges. These methods primarily included SEC, DLS and MFI, which can measure aggregates at the molecular, nano and micron size ranges, respectively. Since aggregation at the molecular level represent early events of molecular interactions, lower size range is expected to better differentiate the test materials with regard to aggregation. Therefore, orthogonal methods were employed to obtain additional information of the aggregates in the molecular size range to complement the results obtained by SEC. Accordingly, SEC MALS was used to understand approximate size of the higher order aggregates in terms of monomeric units and CGE was used to determine nature of these aggregates.

SEC, SEC-MALS and CGE-NR consistently revealed that isoform-A enriched material has higher aggregation than materials containing a high content of isoform-B (fremanezumab DS and the isoform control), mainly in the form of increased higher order aggregates. Agitation and freeze-thaw processes did not make any further difference on the aggregates of molecular size range (soluble aggregates). In contrast, agitation and freeze-thaw processes showed higher particle counts in the isoform-A enriched material after agitation and freeze/thaw compared to the isoform control, with the difference being increasingly apparent at larger particle size (2 µm<5 µm<10 µm<25 µm). This result suggested that the higher order aggregates may have agglomerated into sub-visible particles that should have escaped from detection by SEC due to its resolution limits (<100 nm). The role of thermodynamic stability on the formation of the higher order aggregates was investigated. Results from DSC and ICD analysis showed lower thermodynamic stability of the isoform-A enriched material based on lower total enthalpy and lower free energy of unfolding (ΔG) of third transition. The onset of unfolding was higher for the isoform-A enriched material.

The effect of agitation and freeze-thaw could not be evaluated on the sub-micron aggregates as DLS was used to test the unstressed samples only. However, DLS showed larger hydrodynamic radius in the isoform-A enriched material as compared to the fremanezumab DS or the isoform control. The larger hydrodynamic radius seem to have manifested in the higher viscosity measured for the isoform-A enriched material at higher protein concentrations since it represents one of the key factors that can influence the viscosity of protein formulations. Although viscosity can also be influenced by protein-protein interactions, the observation of increased viscosity was consistent with larger hydrodynamic radius shown in the isoform A enriched material. Further impact of the increased viscosity on the functionality of the PFS drug product was shown by the higher break loose and glide force for syringes filled with the isoform-A enriched material as compared to syringes filled with the fremanezumab DS or the isoform control.

The results showed that chemically enriched isoform-A material of fremanezumab showed significant increase in higher order aggregates, hydrodynamic radius, sub-visible particles after agitation and freeze-thaw, and viscosity, as compared to the fremanezumab drug substance which contains a high isoform-B content. The increased aggregation of isoform-A enriched material may be explained by the reduced thermodynamic stability demonstrated by lowered total enthalpy and free energy of unfolding. Isoform-A enriched material showed lower thermal stability and increased aggregation propensity leading to soluble aggregate formation, which may further yield higher counts of sub-visible particles when subjected to pharmaceutically relevant stress conditions such as agitation and freeze-thaw. Increased viscosity of isoform-A enriched material is consistent with the increased hydrodynamic size, which was further shown to increase the break loose and glide forces measured for the syringes filled with the isoform-A enriched material. These results indicated the importance of the high content of isoform-B in the fremanezumab drug substance, which meets the quality attributes of the commercial drug product, including size heterogeneity, sub-visible particle counts, and syringe functionality, etc.

Antibody Sequences
G1 heavy chain variable region amino acid sequence (SEQ ID NO: 1)
EVQLVESGGGLVQPGGSLRLSCAASGFTFSNYWISWVRQAPGKGLEWVAEIRSESD

ASATHYAEAVKGRFTISRDNAKNSLYLQMNSLRAEDTAVYYCLAYFDYGLAIQNY

WGQGTLVTVSS

-continued

G1 light chain variable region amino acid sequence
(SEQ ID NO: 2)
EIVLTQSPATLSLSPGERATLSCKASKRVTTYVSWYQQKPGQAPRLLIYGASNRYLGI

PARFSGSGSGTDFTLTISSLEPEDFAVYYCSQSYNYPYTFGQGTKLEIK

G1 heavy chain full antibody amino acid sequence (including modified IgG2 as described herein)
(SEQ ID NO: 3)
EVQLVESGGGLVQPGGSLRLSCAASGFTFSNYWISWVRQAPGKGLEWVAEIRSESDA

SATHYAEAVKGRFTISRDNAKNSLYLQMNSLRAEDTAVYYCLAYFDYGLAIQNYWG

QGTLVTVSSASTKGPSVFPLAPCSRSTSESTAALGCLVKDYFPEPVTVSWNSGALTSG

VHTFPAVLQSSGLYSLSSVVTVPSSNFGTQTYTCNVDHKPSNTKVDKTVERKCCVEC

PPCPAPPVAGPSVFLFPPKPKDTLMISRTPEVTCVVVDVSHEDPEVQFNWYVDGVEV

HNAKTKPREEQFNSTFRVVSVLTVVHQDWLNGKEYKCKVSNKGLPSSIEKTISKTKG

QPREPQVYTLPPSREEMTKNQVSLTCLVKGFYPSDIAVEWESNGQPENNYKTTPPML

DSDGSFFLYSKLTVDKSRWQQGNVFSCSVMHEALHNHYTQKSLSLSPGK

G1 light chain full antibody amino acid sequence
(SEQ ID NO: 4)
EIVLTQSPATLSLSPGERATLSCKASKRVTTYVSWYQQKPGQAPRLLIYGASNRYLGI

PARFSGSGSGTDFTLTISSLEPEDFAVYYCSQSYNYPYTFGQGTKLEIKRTVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC

G1 heavy chain variable region nucleotide sequence
(SEQ ID NO: 5)
GAAGTTCAGCTGGTTGAATCCGGTGGTGGTCTGGTTCAGCCAGGTGGTTCCCTGC

GTCTGTCCTGCGCTGCTTCCGGTTTCACCTTCTCCAACTACTGGATCTCCTGGGTT

CGTCAGGCTCCTGGTAAAGGTCTGGAATGGGTTGCTGAAATCCGTTCCGAATCCG

ACGCGTCCGCTACCCATTACGCTGAAGCTGTTAAAGGTCGTTTCACCATCTCCCGT

GACAACGCTAAGAACTCCCTGTACCTGCAGATGAACTCCCTGCGTGCTGAAGACA

CCGCTGTTTACTACTGCCTGGCTTACTTTGACTACGGTCTGGCTATCCAGAACTAC

TGGGGTCAGGGTACCCTGGTTACCGTTTCCTCC

G1 light chain variable region nucleotide sequence
(SEQ ID NO: 6)
GAAATCGTTCTGACCCAGTCCCCGGCTACCCTGTCCCTGTCCCCAGGTGAACGTG

CTACCCTGTCCTGCAAAGCTTCCAAACGGGTTACCACCTACGTTTCCTGGTACCA

GCAGAAACCCGGTCAGGCTCCTCGTCTGCTGATCTACGGTGCTTCCAACCGTTAC

CTCGGTATCCCAGCTCGTTTCTCCGGTTCCGGTTCCGGTACCGACTTCACCCTGAC

CATCTCCTCCCTGGAACCCGAAGACTTCGCTGTTTACTACTGCAGTCAGTCCTAC

AACTACCCCTACACCTTCGGTCAGGGTACCAAACTGGAAATCAAA

G1 CDR H1 (extended CDR shown; Kabat CDR in bold; Chothia CDR is underlined)
(SEQ ID NO: 7)
<u>GFTFS</u>NYWIS

G1 CDR H2 (extended CDR shown; Kabat CDR in bold; Chothia CDR is underlined)
(SEQ ID NO: 8)
<u>EIRSESDASATHYAEAVKG</u>

G1 CDR H3 (Kabat CDR in bold; Chothia CDR is underlined)
(SEQ ID NO: 9)
<u>YFDYGLAIQNY</u>

G1 CDR L1 (Kabat CDR in bold; Chothia CDR is underlined)
(SEQ ID NO: 10)
KASKRVTTYVS

G1 CDR L2 (Kabat CDR in bold; Chothia CDR is underlined)
(SEQ ID NO: 11)
GASNRYL

G1 CDR L3 (Kabat CDR in bold; Chothia CDR is underlined)
(SEQ ID NO: 12)
SQSYNYPYT

G1 heavy chain full antibody nucleotide sequence (including modified IgG2 as described herein)
(SEQ ID NO: 13)
GAAGTTCAGCTGGTTGAATCCGGTGGTGGTCTGGTTCAGCCAGGTGGTTCCCTGC

GTCTGTCCTGCGCTGCTTCCGGTTTCACCTTCTCCAACTACTGGATCTCCTGGGTT

CGTCAGGCTCCTGGTAAAGGTCTGGAATGGGTTGCTGAAATCCGTTCCGAATCCG

ACGCGTCCGCTACCCATTACGCTGAAGCTGTTAAAGGTCGTTTCACCATCTCCCG

TGACAACGCTAAGAACTCCCTGTACCTGCAGATGAACTCCCTGCGTGCTGAAGAC

ACCGCTGTTTACTACTGCCTGGCTTACTTTGACTACGGTCTGGCTATCCAGAACTA

CTGGGGTCAGGGTACCCTGGTTACCGTTTCCTCCGCCTCCACCAAGGGCCCATCT

GTCTTCCCACTGGCCCCATGCTCCCGCAGCACCTCCGAGAGCACAGCCGCCCTGG

GCTGCCTGGTCAAGGACTACTTCCCAGAACCTGTGACCGTGTCCTGGAACTCTGG

CGCTCTGACCAGCGGCGTGCACACCTTCCCAGCTGTCCTGCAGTCCTCAGGTCTC

TACTCCCTCAGCAGCGTGGTGACCGTGCCATCCAGCAACTTCGGCACCCAGACCT

ACACCTGCAACGTAGATCACAAGCCAAGCAACACCAAGGTCGACAAGACCGTGG

AGAGAAAGTGTTGTGTGGAGTGTCCACCTTGTCCAGCCCCTCCAGTGGCCGGACC

ATCCGTGTTCCTGTTCCCTCCAAAGCCAAAGGACACCCTGATGATCTCCAGAACC

CCAGAGGTGACCTGTGTGGTGGTGGACGTGTCCCACGAGGACCCAGAGGTGCAG

TTCAACTGGTATGTGGACGGAGTGGAGGTGCACAACGCCAAGACCAAGCCAAGA

GAGGAGCAGTTCAACTCCACCTTCAGAGTGGTGAGCGTGCTGACCGTGGTGCACC

AGGACTGGCTGAACGGAAAGGAGTATAAGTGTAAGGTGTCCAACAAGGGACTGC

CATCCAGCATCGAGAAGACCATCTCCAAGACCAAGGGACAGCCAAGAGAGCCAC

AGGTGTATACCCTGCCCCCATCCAGAGAGGAGATGACCAAGAACCAGGTGTCCC

TGACCTGTCTGGTGAAGGGATTCTATCCATCCGACATCGCCGTGGAGTGGGAGTC

CAACGGACAGCCAGAGAACAACTATAAGACCACCCCTCCAATGCTGGACTCCGA

CGGATCCTTCTTCCTGTATTCCAAGCTGACCGTGGACAAGTCCAGATGGCAGCAG

GGAAACGTGTTCTCTTGTTCCGTGATGCACGAGGCCCTGCACAACCACTATACCC

AGAAGAGCCTGTCCCTGTCTCCAGGAAAGTAA

G1 light chain full antibody nucleotide sequence
(SEQ ID NO: 14)
GAAATCGTTCTGACCCAGTCCCCGGCTACCCTGTCCCTGTCCCCAGGTGAACGTG

CTACCCTGTCCTGCAAAGCTTCCAAACGGGTTACCACCTACGTTTCCTGGTACCA

GCAGAAACCCGGTCAGGCTCCTCGTCTGCTGATCTACGGTGCTTCCAACCGTTAC

CTCGGTATCCCAGCTCGTTTCTCCGGTTCCGGTTCCGGTACCGACTTCACCCTGAC

CATCTCCTCCCTGGAACCCGAAGACTTCGCTGTTTACTACTGCAGTCAGTCCTAC

AACTACCCCTACACCTTCGGTCAGGGTACCAAACTGGAAATCAAACGCACTGTG

GCTGCACCATCTGTCTTCATCTTCCCTCCATCTGATGAGCAGTTGAAATCCGGAA

-continued

CTGCCTCTGTTGTGTGCCTGCTGAATAACTTCTATCCGCGCGAGGCCAAAGTACA

GTGGAAGGTGGATAACGCCCTCCAATCCGGTAACTCCCAGGAGAGTGTCACAGA

GCAGGACAGCAAGGACAGCACCTACAGCCTCAGCAGCACCCTGACCCTGAGCAA

AGCAGACTACGAGAAACACAAAGTCTACGCCTGCGAAGTCACCCATCAGGGCCT

GAGTTCTCCAGTCACAAAGAGCTTCAACCGCGGTGAGTGCTAA

IgG2Δa CH2 amino acid sequence
(SEQ ID NO: 15)
APPVAGPSVFLFPPKPKDTLMISRTPEVTCVVVDVSHEDPEVQFNWYVDGVEVHNA

KTKPREEQFNSTFRVVSVLTVVHQDWLNGKEYKCKVSNKGLPSSIEKTISKTK

---

What is claimed is:

1. A pharmaceutical composition comprising a plurality of IgG2 anti-CGRP antagonist antibody molecules, wherein at least about 70% of the antibody molecules in the plurality are of the IgG2-B disulfide isoform, and wherein the antibody molecules in the plurality comprise both a heavy chain variable domain amino acid sequence comprising the amino acid sequence of SEQ ID NO: 1 and a light chain variable domain amino acid sequence comprising the amino acid sequence of SEQ ID NO: 2.

2. The pharmaceutical composition of claim 1, wherein the antibody molecules in the plurality comprise a kappa light chain constant region.

3. The pharmaceutical composition of claim 1, wherein the antibody molecules in the plurality comprise a heavy chain comprising a CH2 domain having the amino acid sequence of SEQ ID NO: 15.

4. The pharmaceutical composition of claim 1, wherein the antibody molecules in the plurality comprise a heavy chain comprising the amino acid sequence of SEQ ID NO: 3 and a light chain comprising the amino acid sequence of SEQ ID NO: 4.

5. The pharmaceutical composition of claim 1, wherein between about 15% and about 25% of the antibody molecules in the plurality are of the IgG2-AB disulfide isoform.

6. The pharmaceutical composition of claim 1, wherein between about 3% and about 7% of the antibody molecules in the plurality are of the IgG2-A disulfide isoform.

7. The pharmaceutical composition of claim 1, wherein at least about 5% of the antibody molecules in the plurality are of the IgG2-A disulfide isoform.

8. The pharmaceutical composition of claim 1, wherein at least about 20% of the antibody molecules in the plurality are of the IgG2-AB disulfide isoform.

9. A pharmaceutical composition comprising a plurality of IgG2 monoclonal antibody molecules,
wherein between about 70% and about 80% of the antibody molecules in the plurality are of the IgG2-B disulfide isoform;
wherein between about 3% and about 7% of the antibody molecules in the plurality are of the IgG2-A disulfide isoform;
wherein between about 15% and about 25% of the antibody molecules in the plurality are of the IgG2-AB disulfide isoform; and
wherein the antibody molecules in the plurality comprise a heavy chain variable domain amino acid sequence comprising the amino acid sequence of SEQ ID NO: 1 and a light chain variable domain amino acid sequence comprising the amino acid sequence of SEQ ID NO: 2.

10. The pharmaceutical composition of claim 9, wherein the antibody molecules in the plurality comprise a kappa light chain constant region.

11. The pharmaceutical composition of claim 9, wherein the antibody molecules in the plurality comprise a heavy chain comprising a CH2 domain having the amino acid sequence of SEQ ID NO: 15.

12. The pharmaceutical composition of claim 9, wherein the antibody molecules in the plurality comprise both a heavy chain comprising the amino acid sequence of SEQ ID NO: 3 and a light chain comprising the amino acid sequence of SEQ ID NO: 4.

13. The pharmaceutical composition of claim 1, wherein about 72% of the antibody molecules in the plurality are of the disulfide isoform B, wherein about 22% of the antibody molecules in the plurality are of the IgG2-AB disulfide isoform, and wherein about 6% of the antibody molecules in the plurality are of the IgG2-A disulfide isoform.

14. The pharmaceutical composition of claim 1, wherein the amount of the disulfide isoform present in the plurality is as determined using reverse-phase high-performance liquid chromatography (RP-HPLC).

15. The pharmaceutical composition of claim 1, wherein the composition is liquid and wherein the plurality of IgG2 antibody molecules are present in the composition at a concentration of least about 120 mg/mL.

16. The pharmaceutical composition of claim 1, wherein the composition is liquid and wherein the plurality of IgG2 antibody molecules are present in the composition at a concentration of at least about 150 mg/mL.

17. The pharmaceutical composition of claim 1, further comprising a sugar or a sugar alcohol.

18. The pharmaceutical composition of claim 17, wherein the sugar or sugar alcohol is selected from the group consisting of sorbitol, sucrose, trehalose, and mannitol.

19. The pharmaceutical composition of claim 1, further comprising a chelating agent.

20. The pharmaceutical composition of claim 19, wherein the chelating agent is ethylenediaminetetraacetic acid (EDTA) or diethylenetriaminepentaacetic acid (DTPA).

21. The pharmaceutical composition of claim 1, further comprising a surfactant.

22. The pharmaceutical composition of claim 21, wherein the surfactant is polysorbate 20, polysorbate 60, polysorbate 80, or a combination thereof.

23. The pharmaceutical composition of claim 1, further comprising a buffering agent.

24. The pharmaceutical composition of claim 23, wherein the buffering agent comprises histidine, arginine, glycine, asparagine, or a combination thereof.

25. The pharmaceutical composition of claim 1, wherein the composition comprises a pH of between about 5.0 and about 6.0.

26. The pharmaceutical composition of claim 25, wherein the composition comprises a pH of about 5.5.

27. The pharmaceutical composition of claim 1, wherein the plurality of IgG2 antibody molecules are present in the composition at a concentration of at least about 150 mg/mL, wherein the composition is a liquid composition, and wherein the composition comprises about 3.5 mM L-histidine, about 12.5 mM L-histidine hydrochloride monohydrate, about 193 mM sucrose, about 0.37 mM EDTA, and about 0.15 mM polysorbate 80, at about pH 5.5.

28. The pharmaceutical composition of claim 1, wherein the composition comprises a conductivity of from about 1.3 mS/cm to about 1.5 mS/cm.

29. The pharmaceutical composition of claim 1, wherein ≥95% of the antibody molecules in the plurality are monomeric as determined by size exclusion high-performance liquid chromatography (SE-HPLC).

30. The pharmaceutical composition of claim 1, wherein ≤5% of the antibody molecules in the plurality are dimeric as determined by SE-HPLC.

31. The pharmaceutical composition of claim 30, wherein ≤3.5% of the antibody molecules in the plurality are dimeric as determined by SE-HPLC.

32. The pharmaceutical composition of claim 1, wherein the composition is stable after storage at 2-8° C. for at least 3 months.

33. The pharmaceutical composition of claim 32, wherein the composition is stable after storage at 2-8° C. for at least 6 months.

34. The pharmaceutical composition of claim 32, wherein the antibody molecules in the plurality retain at least about 80% of their antigen-binding activity after storage, as compared to the antigen-binding activity of the antibody molecules in the plurality prior to storage.

35. The pharmaceutical composition of claim 1, wherein the composition is stored in a container selected from the group consisting of a vial, a cartridge, a syringe, and an autoinjector device.

36. The pharmaceutical composition of claim 1, wherein the composition is suitable for subcutaneous or intravenous administration to a subject.

37. The pharmaceutical composition of claim 35, wherein the container comprises less than about 2 mL of the pharmaceutical composition.

38. The pharmaceutical composition of claim 37, wherein the container comprises 1.5 mL of the pharmaceutical composition.

39. A liquid pharmaceutical composition comprising about 225 mg fremanezumab, about 0.204 mg disodium ethylenediaminetetraacetic acid dihydrate (EDTA), about 0.815 mg L-histidine, about 3.93 mg L-histidine hydrochloride monohydrate, about 0.3 mg polysorbate-80, about 99 mg sucrose, and water for injection, at a pH of about 5.5,
wherein at least about 70% of the fremanezumab in the liquid pharmaceutical composition is of the IgG2-B disulfide isoform; and
wherein the liquid pharmaceutical composition has a volume of about 1.5 mL.

40. A pre-filled syringe comprising about 1.5 mL of a liquid pharmaceutical composition, wherein the liquid pharmaceutical composition comprises about 225 mg fremanezumab, about 0.204 mg disodium ethylenediaminetetraacetic acid dihydrate (EDTA), about 0.815 mg L-histidine, about 3.93 mg L-histidine hydrochloride monohydrate, about 0.3 mg polysorbate-80, about 99 mg sucrose, and water for injection, at a pH of about 5.5,
wherein at least about 70% of the fremanezumab in the liquid pharmaceutical composition is of the IgG2-B disulfide isoform.

41. A pre-filled autoinjector comprising about 1.5 mL of a liquid pharmaceutical composition, wherein the liquid pharmaceutical composition comprises about 225 mg fremanezumab, about 0.204 mg disodium ethylenediaminetetraacetic acid dihydrate (EDTA), about 0.815 mg L-histidine, about 3.93 mg L-histidine hydrochloride monohydrate, about 0.3 mg polysorbate-80, about 99 mg sucrose, and water for injection, at a pH of about 5.5,
wherein at least about 70% of the fremanezumab in the liquid pharmaceutical composition is of the IgG2-B disulfide isoform.

42. A method of treating headache in a subject in need thereof, comprising administering to the subject a therapeutically effective amount of a pharmaceutical composition comprising a plurality of IgG2 anti-CGRP antagonist antibody molecules, wherein at least about 70% of the antibody molecules in the plurality are of the IgG2-B disulfide isoform, and wherein the antibody molecules in the plurality comprise both a heavy chain variable domain amino acid sequence comprising the amino acid sequence of SEQ ID NO: 1 and a light chain variable domain amino acid sequence comprising the amino acid sequence of SEQ ID NO: 2.

43. The method of claim 42, wherein the headache is migraine headache.

44. The method of claim 43, wherein the migraine headache is chronic migraine headache or episodic migraine headache.

45. The method of claim 42, wherein the headache is cluster headache.

46. The method of claim 45, wherein the cluster headache is chronic cluster headache or episodic cluster headache.

47. The method of claim 42, wherein the headache is post-traumatic headache, post-ictal headache, or medication overuse headache.

48. A method of treating pain in a subject in need thereof, comprising administering to the subject a therapeutically effective amount of a pharmaceutical composition comprising a plurality of IgG2 anti-CGRP antagonist antibody molecules, wherein at least about 70% of the antibody molecules in the plurality are of the IgG2-B disulfide isoform, and wherein the antibody molecules in the plurality comprise both a heavy chain variable domain amino acid sequence comprising the amino acid sequence of SEQ ID NO: 1 and a light chain variable domain amino acid sequence comprising the amino acid sequence of SEQ ID NO: 2.

49. The method of claim 48, wherein the pain is chronic pain.

50. The method of claim 49, wherein the chronic pain is associated with fibromyalgia.

51. The method of claim 48, wherein the pain is visceral pain.

52. The method of claim 51, wherein the visceral pain is (a) associated with or results from interstitial cystitis, or (b) is associated with or results from bladder pain syndrome.

* * * * *

UNITED STATES PATENT AND TRADEMARK OFFICE
CERTIFICATE OF CORRECTION

PATENT NO. : 10,899,826 B1  
APPLICATION NO. : 16/569462  
DATED : January 26, 2021  
INVENTOR(S) : Jason Bock and John Kim Page 1 of 1

It is certified that error appears in the above-identified patent and that said Letters Patent is hereby corrected as shown below:

In the Claims

Column 65, Line 35, Claim 5, delete "IgG2-AB" and insert -- IgG2-A/B --, therefor.

Column 65, Line 44, Claim 8, delete "IgG2-AB" and insert -- IgG2-A/B --, therefor.

Column 65, Line 54, Claim 9, delete "IgG2-AB" and insert -- IgG2-A/B --, therefor.

Column 66, Line 18, Claim 13, delete "IgG2-AB" and insert -- IgG2-A/B --, therefor.

Column 66, Line 28, Claim 15, delete "least" and insert -- at least --, therefor.

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 15

<210> SEQ ID NO 1
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Ile Ser Trp Val Arg Gln Ala Pro Gly Lys Gly Leu Glu Trp Val
        35                  40                  45

Ala Glu Ile Arg Ser Glu Ser Asp Ala Ser Ala Thr His Tyr Ala Glu
    50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
            85                  90                  95

Tyr Cys Leu Ala Tyr Phe Asp Tyr Gly Leu Ala Ile Gln Asn Tyr Trp
            100                 105                 110

Gly Gln Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

```
Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys
            100                 105

<210> SEQ ID NO 3
<211> LENGTH: 448
<212> TYPE: PRT
<213> ORGANISM: Artificial Sequence
<220> FEATURE:
<223> OTHER INFORMATION: Synthetic polypeptide

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
                20                  25                  30

Trp Ile Ser Trp Val Arg Gln Ala Pro Gly Lys Gly Leu Glu Trp Val
            35                  40                  45

Ala Glu Ile Arg Ser Glu Ser Asp Ala Ser Ala Thr His Tyr Ala Glu
        50                  55                  60

Ala Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Leu Ala Tyr Phe Asp Tyr Gly Leu Ala Ile Gln Asn Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Cys Ser Arg Ser Thr Ser Glu Ser Thr
        130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Asn Phe Gly Thr Gln Thr Tyr Thr Cys Asn Val Asp
            195                 200                 205

His Lys Pro Ser Asn Thr Lys Val Asp Lys Thr Val Glu Arg Lys Cys
        210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335
```

-continued

```
Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 4
<211> LENGTH: 214
<212> TYPE: PRT
<213> ORGANISM: Artificial Sequence
<220> FEATURE:
<223> OTHER INFORMATION: Synthetic polypeptide

<400> SEQUENCE: 4

```
Glu Ile Val Leu Thr Gln Ser Pro Ala Thr Leu Ser Leu Ser Pro Gly
1               5                   10                  15

Glu Arg Ala Thr Leu Ser Cys Lys Ala Ser Lys Arg Val Thr Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Leu Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Ser Gln Ser Tyr Asn Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 366
<212> TYPE: DNA
<213> ORGANISM: Artificial Sequence

```
<220> FEATURE:
<223> OTHER INFORMATION: Synthetic polynucleotide

<400> SEQUENCE: 5
gaagttcagc tggttgaatc cggtggtggt ctggttcagc caggtggttc cctgcgtctg      60
tcctgcgctg cttccggttt caccttctcc aactactgga tctcctgggt tcgtcaggct     120
cctggtaaag gtctggaatg ggttgctgaa atccgttccg aatccgacgc gtccgctacc     180
cattacgctg aagctgttaa aggtcgtttc accatctccc gtgacaacgc taagaactcc     240
ctgtacctgc agatgaactc cctgcgtgct gaagacaccg ctgttactta ctgcctggct     300
tactttgact acggtctggc tatccagaac tactggggtc agggtaccct ggttaccgtt     360
tcctcc                                                                366

<210> SEQ ID NO 6
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 6
gaaatcgttc tgacccagtc cccggctacc ctgtccctgt ccccaggtga acgtgctacc      60
ctgtcctgca agcttccaa acgggttacc acctacgttt cctggtacca gcagaaaccc     120
ggtcaggctc ctcgtctgct gatctacggt gcttccaacc gttacctcgg tatcccagct     180
cgtttctccg gttccggttc cggtaccgac ttcaccctga ccatctcctc cctggaaccc     240
gaagacttcg ctgtttacta ctgcagtcag tcctacaact accctacac cttcggtcag     300 ggtaccaaac tggaaatcaa a                                               321

<210> SEQ ID NO 7
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 7

Gly Phe Thr Phe Ser Asn Tyr Trp Ile Ser
1               5                   10

<210> SEQ ID NO 8
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 8

Glu Ile Arg Ser Glu Ser Asp Ala Ser Ala Thr His Tyr Ala Glu Ala
1               5                   10                  15
Val Lys Gly

<210> SEQ ID NO 9
<211> LENGTH: 11
<212> TYPE: PRT
<213> ORGANISM: Artificial Sequence
<220> FEATURE:
<223> OTHER INFORMATION: Synthetic polypeptide
```

<400> SEQUENCE: 9

Tyr Phe Asp Tyr Gly Leu Ala Ile Gln Asn Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 10

Lys Ala Ser Lys Arg Val Thr Thr Tyr Val Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 11

Gly Ala Ser Asn Arg Tyr Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Ser Gln Ser Tyr Asn Tyr Pro Tyr Thr
1               5

<210> SEQ ID NO 13
<211> LENGTH: 1347
<212> TYPE: DNA
<213> ORGANISM: Artificial Sequence
<220> FEATURE:
<223> OTHER INFORMATION: Synthetic polynucleotide

<400> SEQUENCE: 13

| | | | | | |
|---|---|---|---|---|---|
| gaagttcagc | tggttgaatc | cggtggtggt | ctggttcagc | caggtggttc | cctgcgtctg | 60 |
| tcctgcgctg | cttccggttt | caccttctcc | aactactgga | tctcctgggt | tcgtcaggct | 120 |
| cctggtaaag | gtctggaatg | ggttgctgaa | atccgttccg | aatccgacgc | gtccgctacc | 180 |
| cattacgctg | aagctgttaa | aggtcgtttc | accatctccc | gtgacaacgc | taagaactcc | 240 |
| ctgtacctgc | agatgaactc | cctgcgtgct | gaagacaccg | ctgtttacta | ctgcctggct | 300 |
| tactttgact | acggtctggc | tatccagaac | tactggggtc | agggtaccct | ggttaccgtt | 360 |
| tcctccgcct | ccaccaaggg | cccatctgtc | ttcccactgg | ccccatgctc | cgcagcacc  | 420 |
| tccgagagca | cagccgccct | gggctgcctg | gtcaaggact | acttcccaga | acctgtgacc | 480 |
| gtgtcctgga | actctggcgc | tctgaccagc | ggcgtgcaca | ccttcccagc | tgtcctgcag | 540 |
| tcctcaggtc | tctactccct | cagcagcgtg | gtgaccgtgc | catccagcaa | cttcggcacc | 600 |
| cagacctaca | cctgcaacgt | agatcacaag | ccaagcaaca | ccaaggtcga | caagaccgtg | 660 |
| gagagaaagt | gttgtgtgga | gtgtccacct | tgtccagccc | ctccagtggc | cggaccatcc | 720 |
| gtgttcctgt | tccctccaaa | gccaaaggac | accctgatga | tctccagaac | cccagaggtg | 780 |

```
acctgtgtgg tggtggacgt gtcccacgag gacccagagg tgcagttcaa ctggtatgtg    840
gacggagtgg aggtgcacaa cgccaagacc aagccaagag aggagcagtt caactccacc    900
ttcagagtgg tgagcgtgct gaccgtggtg caccaggact ggctgaacgg aaaggagtat    960
aagtgtaagg tgtccaacaa gggactgcca tccagcatcg agaagaccat ctccaagacc   1020
aagggacagc caagagagcc acaggtgtat accctgcccc catccagaga ggagatgacc   1080
aagaaccagg tgtccctgac ctgtctggtg aagggattct atcccatccga catcgccgtg   1140 gagtgggagt ccaacggaca gccagagaac aactataaga ccacccctcc aatgctggac   1200
tccgacggat ccttcttcct gtattccaag ctgaccgtgg acaagtccag atggcagcag   1260
ggaaacgtgt tctcttgttc cgtgatgcac gaggccctgc acaaccacta cccagaag    1320 agcctgtccc tgtctccagg aaagtaa                                       1347

<210> SEQ ID NO 14
<211> LENGTH: 645
<212> TYPE: DNA
<213> ORGANISM: Artificial Sequence
<220> FEATURE:
<223> OTHER INFORMATION: Synthetic polynucleotide

<400> SEQUENCE: 14
gaaatcgttc tgacccagtc cccggctacc ctgtccctgt ccccaggtga acgtgctacc     60
ctgtcctgca agcttccaa acgggttacc acctacgttt cctggtacca gcagaaaccc    120
ggtcaggctc ctcgtctgct gatctacggt gcttccaacc gttacctcgg tatcccagct    180
cgtttctccg gttccggttc cggtaccgac ttcaccctga ccatctcctc cctggaaccc    240
gaagacttcg ctgtttacta ctgcagtcag tcctacaact accctacac cttcggtcag    300 ggtaccaaac tggaaatcaa acgcactgtg gctgcaccat ctgtcttcat cttccctcca    360
tctgatgagc agttgaaatc cggaactgcc tctgttgtgt gcctgctgaa taacttctat    420
ccgcgcgagg ccaaagtaca gtggaaggtg gataacgccc tccaatccgg taactcccag    480
gagagtgtca cagagcagga cagcaaggac agcacctaca gcctcagcag caccctgacc    540
ctgagcaaag cagactacga gaaacacaaa gtctacgcct gcgaagtcac ccatcagggc    600
ctgagttctc cagtcacaaa gagcttcaac cgcggtgagt gctaa                   645

<210> SEQ ID NO 15
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 15

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80
```

```
Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Thr Lys
                100                 105
```